(12) United States Patent
Salahieh et al.

(10) Patent No.: US 7,959,672 B2
(45) Date of Patent: Jun. 14, 2011

(54) REPLACEMENT VALVE AND ANCHOR

(75) Inventors: Amr Salahieh, Saratoga, CA (US);
Brian D. Brandt, Santa Clara, CA (US);
Dwight P. Morejohn, Davis, CA (US);
Ulrich R. Haug, Campbell, CA (US);
Jean-Pierre Dueri, Stockton, CA (US);
Hans F. Valencia, Berkeley, CA (US);
Robert A. Geshlider, San Francisco, CA (US)

(73) Assignee: Sadra Medical, Saratoga, CA (US)

( * ) Notice: Subject to any disclaimer, the term of this patent is extended or adjusted under 35 U.S.C. 154(b) by 962 days.

(21) Appl. No.: 10/911,059

(22) Filed: Aug. 3, 2004

(65) Prior Publication Data
US 2005/0137695 A1 Jun. 23, 2005

Related U.S. Application Data

(63) Continuation of application No. 10/746,872, filed on Dec. 23, 2003.

(51) Int. Cl.
*A61F 2/24* (2006.01)
(52) U.S. Cl. ............... 623/2.17; 623/1.24; 623/1.26; 623/2.1; 623/2.14
(58) Field of Classification Search ............... 623/1.26, 623/2.11, 2.14
See application file for complete search history.

(56) References Cited

U.S. PATENT DOCUMENTS

| | | | |
|---|---|---|---|
| 3,334,629 A | 8/1967 | Cohn | |
| 3,409,013 A | 11/1968 | Berry | |
| 3,540,431 A | 11/1970 | Mobin-Uddin | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,056,854 A | 11/1977 | Boretos et al. | |
| 4,106,129 A | 8/1978 | Carpentier et al. | |
| 4,233,690 A | 11/1980 | Akins | |

(Continued)

FOREIGN PATENT DOCUMENTS

CN 1338951 A 3/2002

(Continued)

OTHER PUBLICATIONS

Salahieh, A. et al. U.S. Appl. No. 10/746,280 entitled "Repositionable heart valve and method", filed Dec. 23, 2003.

(Continued)

*Primary Examiner* — Corrine M McDermott
*Assistant Examiner* — Christopher D Prone
(74) *Attorney, Agent, or Firm* — Vidas, Arrett & Steinkraus

(57) ABSTRACT

Apparatus for endovascularly replacing a patient's heart valve, including: a replacement valve adapted to be delivered endovascularly to a vicinity of the heart valve; an expandable anchor adapted to be delivered endovascularly to the vicinity of the heart valve; and a lock mechanism configured to maintain a minimum amount of anchor expansion. The invention also includes a method for endovascularly replacing a patient's heart valve. In some embodiments the method includes the steps of: endovascularly delivering a replacement valve and an expandable anchor to a vicinity of the heart valve; expanding the anchor to a deployed configuration; and locking the anchor in the deployed configuration.

23 Claims, 49 Drawing Sheets

U.S. PATENT DOCUMENTS

| | | |
|---|---|---|
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,580,568 A | 4/1986 | Gianturco |
| 4,602,911 A | 7/1986 | Ahmadi et al. |
| 4,610,688 A | 9/1986 | Silvestrini et al. |
| 4,617,932 A | 10/1986 | Kornberg |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,217,483 A | 6/1993 | Tower |
| 5,258,042 A | 11/1993 | Mehta |
| 5,332,402 A | 7/1994 | Teitelbaum et al. |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A * | 8/1995 | Schmitt ........................ 623/1.49 |
| 5,476,506 A | 12/1995 | Lunn |
| 5,476,510 A | 12/1995 | Eberhardt et al. |
| 5,480,423 A | 1/1996 | Ravenscroft et al. |
| 5,507,767 A | 4/1996 | Maeda et al. |
| 5,534,007 A | 7/1996 | St. Germain et al. |
| 5,545,133 A | 8/1996 | Burns et al. |
| 5,545,211 A | 8/1996 | An et al. |
| 5,549,665 A | 8/1996 | Vesely et al. |
| 5,554,185 A | 9/1996 | Block et al. |
| 5,571,215 A | 11/1996 | Sterman et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson, IV et al. |
| 5,720,391 A | 2/1998 | Dohm et al. |
| 5,733,325 A | 3/1998 | Robinson et al. |
| 5,735,842 A | 4/1998 | Krueger et al. |
| 5,769,812 A | 6/1998 | Stevens et al. |
| 5,800,456 A | 9/1998 | Maeda et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,860,996 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,104 A | 4/2000 | Jang |
| 6,093,203 A | 7/2000 | Uflacker |
| 6,123,723 A | 9/2000 | Konya et al. |
| 6,142,987 A | 11/2000 | Tsugita |
| 6,143,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,179,859 B1 | 1/2001 | Bates |
| 6,187,016 B1 | 2/2001 | Hedges et al. |
| 6,197,053 B1 * | 3/2001 | Cosgrove et al. ............ 623/2.11 |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |

| | | |
|---|---|---|
| 6,416,510 B1 | 7/2002 | Altman et al. |
| 6,425,916 B1 * | 7/2002 | Garrison et al. ............ 623/2.11 |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,764,503 B1 | 7/2004 | Ishimaru |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,229 B1 | 9/2004 | Berreklouw |
| 6,790,237 B2 | 9/2004 | Stinson |
| 6,814,746 B2 | 11/2004 | Thompson et al. |
| 6,821,297 B2 | 11/2004 | Snyders |
| 6,837,901 B2 | 1/2005 | Rabkin et al. |
| 6,843,802 B1 | 1/2005 | Villalobos et al. |
| 6,863,668 B2 | 3/2005 | Gillespie et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,905,743 B1 | 6/2005 | Chen et al. |
| 6,911,036 B2 | 6/2005 | Douk et al. |
| 6,936,058 B2 | 8/2005 | Forde et al. |
| 6,936,067 B2 | 8/2005 | Buchanan |
| 6,953,332 B1 | 10/2005 | Kurk et al. |
| 6,964,673 B2 | 11/2005 | Tsugita et al. |
| 6,969,395 B2 | 11/2005 | Eskuri |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 7,011,681 B2 | 3/2006 | Veseley |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,374,560 B2 | 5/2008 | Ressemann et al. |
| 7,632,298 B2 | 12/2009 | Hijlkema et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 * | 11/2001 | Moore ......................... 623/1.16 |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032480 A1 | 3/2002 | Spence et al. |
| 2002/0032481 A1 * | 3/2002 | Gabbay ...................... 623/2.11 |
| 2002/0052651 A1 | 5/2002 | Myers et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 | 3/2003 | Yang et al. |
| 2003/0055495 A1 * | 3/2003 | Pease et al. .................. 623/2.11 |
| 2003/0060844 A1 | 3/2003 | Borillo et al. |
| 2003/0070944 A1 | 4/2003 | Nigam |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |

| | | |
|---|---|---|
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0088045 A1 | 5/2004 | Cox |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0098112 A1 | 5/2004 | DiMatteo et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0254636 A1 | 12/2004 | Flagle et al. |
| 2005/0033402 A1 | 2/2005 | Cully et al. |
| 2005/0043711 A1 | 2/2005 | Corcoran et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137701 A1 | 6/2005 | Salahieh et al. |
| 2005/0165352 A1 | 7/2005 | Henry et al. |
| 2005/0165477 A1 | 7/2005 | Anduiza et al. |
| 2005/0197694 A1 | 9/2005 | Pai et al. |
| 2005/0197695 A1 | 9/2005 | Stacchino et al. |
| 2005/0203614 A1 | 9/2005 | Forster |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0155312 A1 | 7/2006 | Levine et al. |
| 2006/0259134 A1 | 11/2006 | Schwammenthal et al. |
| 2007/0016286 A1 | 1/2007 | Herrmann et al. |
| 2008/0269878 A1 | 10/2008 | Iobbi |
| 2008/0288054 A1 | 11/2008 | Pulnev et al. |
| 2009/0054969 A1 | 2/2009 | Salahieh et al. |
| 2009/0076598 A1 | 3/2009 | Salahieh et al. |
| 2009/0264997 A1 | 10/2009 | Haug et al. |
| 2010/0219092 A1 | 9/2010 | Salahieh et al. |

FOREIGN PATENT DOCUMENTS

| | | |
|---|---|---|
| EP | 0409929 B1 | 4/1997 |
| EP | 1000590 A1 | 5/2000 |
| EP | 1057459 | 12/2000 |
| EP | 1057460 | 12/2000 |
| EP | 0937439 B1 | 9/2003 |
| EP | 1340473 | 9/2003 |
| EP | 1356793 | 10/2003 |
| EP | 1042045 B1 | 5/2004 |
| EP | 0819013 | 6/2004 |
| EP | 1589902 | 8/2004 |
| EP | 1605871 | 9/2004 |
| EP | 1229864 B1 | 4/2005 |
| EP | 1582178 A2 | 5/2005 |
| EP | 1430853 A3 | 6/2005 |
| EP | 1059894 B1 | 7/2005 |
| EP | 1551274 A2 | 7/2005 |
| EP | 1551336 A1 | 7/2005 |
| EP | 1078610 B1 | 8/2005 |
| EP | 1562515 A1 | 8/2005 |
| EP | 1576937 A2 | 9/2005 |
| EP | 1582179 A2 | 10/2005 |
| EP | 1469797 | 11/2005 |
| EP | 1600121 A1 | 11/2005 |
| EP | 1156757 B1 | 12/2005 |
| EP | 1616531 | 1/2006 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 96/24306 A1 | 8/1996 |
| WO | WO 98/36790 | 8/1998 |
| WO | WO 98/50103 A1 | 11/1998 |
| WO | WO 98/57599 A2 | 12/1998 |
| WO | WO 99/44542 A2 | 9/1999 |
| WO | WO 00/09059 | 2/2000 |
| WO | WO 00/44308 | 8/2000 |
| WO | WO 00/44313 | 8/2000 |
| WO | WO 00/49970 A1 | 8/2000 |
| WO | WO 00/67661 | 11/2000 |
| WO | WO 01/05331 | 1/2001 |
| WO | WO 01/08596 A1 | 2/2001 |
| WO | WO 01/10320 A1 | 2/2001 |
| WO | WO 01/10343 A1 | 2/2001 |
| WO | WO 01/35870 | 5/2001 |
| WO | WO 01/64137 | 9/2001 |
| WO | WO 02/36048 | 5/2002 |
| WO | WO 02/41789 A2 | 5/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | WO03/030776 A2 | 4/2003 |
| WO | WO 03/015851 | 11/2003 |
| WO | WO03/094797 | 11/2003 |
| WO | WO 2004/019811 | 3/2004 |
| WO | WO 2004/023980 | 3/2004 |
| WO | WO 2004/041126 | 5/2004 |
| WO | WO 2004/047681 | 6/2004 |
| WO | WO 2005/084595 | 9/2005 |
| WO | WO 2005/087140 A1 | 9/2005 |

OTHER PUBLICATIONS

Salahieh, A. et al. U.S. Appl. No. 10/893,131 entitled "Methods and apparatus for endovascularly replacing a patient's heart valve", filed Jul. 15, 2004.

Salahieh, A. et al. U.S. Appl. No. 10/893,151, entitled "Methods and apparatus for endovascularly replacing a patient's heart valve", filed Jul. 15, 2004.

Salahieh, A. et al. U.S. Appl. No. 10/893,143, entitled "Methods and apparatus for endovascularly replacing a patient's heart valve", filed Jul. 15, 2004.

Salahieh, A. et al. U.S. Appl. No. 10/893,142, entitled "Methods and apparatus for endovascularly replacing a patient's heart valve", filed Jul. 15, 2004.
Salahieh, A. et al. U.S. Appl. No. 10/920,736, entitled "Apparatus and methods for protecting against embolization during endovascular heart replacement", filed Aug. 17, 2004.
Salahieh, A. et al., U.S. Appl. No. 10/746,240, entitled "Heart valve anchor and method", filed Dec. 23, 2003.
Salahieh, A. et al., U.S. Appl. No. 10/972,287, entitled "Leaflet engagement elements and methods for use thereof", filed Oct. 21, 2004.
Salahieh, A. et al., U.S. Appl. No. 10/971,535, entitled "Leaflet engagement elements and methods for use thereof", filed Oct. 21, 2004.
Salahieh, A. et al., U.S. Appl. No. 10/746,120, entitled "Externally expandable heart valve anchor and method", filed Dec. 23, 2003.
Salahieh, A. et al., U.S. Appl. No. 10/982,388, entitled "Methods and apparatus for endovascularly replacing a heart valve", filed Nov. 5, 2004.
Salahieh, A. et al., U.S. Appl. No. 10/746,285, entitled "Retrievable heart valve anchor and method", filed Dec. 23, 2003.
Salahieh, A. et al., U.S. Appl. No. 10/982,692, entitled "Retrievable heart valve anchor and method", filed Nov. 5, 2004.
Salahieh, A. et al., U.S. Appl. No. 10/746,887, entitled "Low profile heart valve and delivery system", filed Dec. 23, 2003.
Salahieh, A. et al., U.S. Appl. No. 10/746,872, entitled "Locking heart valve anchor", filed Dec. 23, 2003.
Salahieh, A. et al., U.S. Appl. No. 10/746,942, entitled "Two-piece heart valve and anchor", filed Dec. 23, 2003.
Salahieh, A. et al., U.S. Appl. No. 10/870,340, entitled "Everting heart valve", filed Jun. 16, 2004.
Boudjemline, Y. et al., "Percutaneious implantation of a biological valve in the aorta to treat aortic valve insufficiency—a sheep study", Med Sci.Monit. (2002) vol. 8, No. 4, pp. BR113-116.
Fawzi, et al., U:S. Appl. No. 11/155,309, entitled "Apparatus and methods for intravascular embolic protection," filed Jun. 16, 2005.
Salahieh, et al., U.S. Appl. No. 11/232,441, entitled "Methods and apparatus for endovascular heart valve replacement comprising tissue grasping elements," filed Sep. 20, 2005.
Salahieh, et al., U.S. Appl. No. 11/232,444, entitled "Methods and apparatus for endovascular heart valve replacement comprising tissue grasping elements," filed Sep. 20, 2005.
Salahieh, et al., U.S. Appl. No. 11/274,889, entitled "Medical implant deployment tool," filed Nov. 14, 2005.
Salahieh, et al., U.S. Appl. No. 11/314,183, entitled "Medical Device Delivery," filed Dec. 20, 2005.
Salahieh, et al., U.S. Appl. No. 11/314,969, entitled "Methods And Apparatus For Performing Valvuloplasty," filed Dec. 20, 2005.
Salahieh, et al., U.S. Appl. No. 11/275,912, entitled "Medical Implant Delivery and Deployment Tool," filed Feb. 2, 2006.
Salahieh, et al., U.S. Appl. No. 11/275,913, entitled "Two-Part Package for Medical Implant," filed Feb. 2, 2006.
Salahieh, et al., U.S. App. No. 11/531,980, "Externally expandable heart valve anchor and method," filed Sep. 14, 2006.
Salahieh, et al., U.S. App. No. 11/532,019, "Methods and apparatus for endovascularly replacing heart valve," filed Sep. 14, 2006.
Haug, et al; U.S. Appl. No. 11/716,123, entitled "Methods and apparatus for endovasculary replacing a heart valve," filed Mar. 9, 2007.
Salahieh, et al; U.S. Appl. No. 11/706,549, entitled "Systems and Methods for Delivering a Medical Implant," filed Feb. 14, 2007.
Salahieh, et al; U.S. Appl. No. 11/732,906 entitled "Assessing the location and performance of replacement heart valves," filed Apr. 4, 2007.
Andersen, H.R. et al., "Transluminal implantation of artificial heart valves. Description of a new expandable aortic valve and initial results with implantation by catheter technique in closed chest pigs". Euro. Heart J. (1992) 13:704-708.
Atwood, A. et al., "Insertion of Heart Valves by Catheterization". Project Supervised by Prof. Y. Muftu of Northeaster University (2001-2002) 36-40.
Bodnar, E. et al., Replacement Cardiac Valves, Pergamon Publishing Corporation, New York, (1991), 307-322.
Boudjemline, Y. et al., "Percutaneous implantation of a valve in the descending aorta in lambs". Euro. Heart J. (2002) 23:13, 1045-1049.

Boudjemline, Y. et al., "Percutaneous Pulmonary Valve Replacement in a Large Right Ventricular Outflow Tract". J. of Am. College of Cardio. (2004) 43:6, 1082-1087.
Boudjemline, Y. et al., "Percutaneous valve insertion: A new approach?" J. of Thoracic and Cardio. Surg. (2003) 125:3, 741-743.
Boudjemline, Y. et al., "Steps Toward Percutaneous Aortic Valve Replacement." Circulation (2002) 775-778.
Cribier, A. et al., "Early Experience with Percutaneous Transcatheter Implantation of Heart Valve Prosthesis for the Treatment of End-Stage Inoperable Patients with Calcific Aortic Stenosis". J. or Am. Coll. of Cardio. (2004) 43:4, 698-703.
Cribier, A., et al., "Percutaneous Transcatheter Implantation of an Aortic Valve Prosthesis for Calcific Aortic Stenosis: First Human Case Description," Circulation (2002) 3006-3008.
Cribier, A., et al., "Percutaneous Transcatheter Implantation of an Aortic Valve Prosthesis for Calcific Aortic Stenosis: First Human Case". Percutaneous Valve Technologies, Inc. (2002).
Ferrari, M. et al., "Percutaneous transvascular aortic valve replacement with self expanding stent-valve device". Poster from the presentation given at SMIT 2000, $12^{th}$ International Conference (Sep. 5, 2000).
Hijazi, Z.M., "Transcatheter Valve Replacement: A New Era of Percutaneous Cardiac Intervention Begins". J. of Am. College of Cardio. (2004) 43:6, 1088-1089.
Huber, C.H. et al., "Do valved stents compromise coronary flow?" European Journal of Cardio-thoracic Surgery, (2004) 25:754-759.
Knudsen, L. L. et al., "Catheter-implanted prosthetic heart valves". Int'l J. of Art. Organs, (1993) 16:5, 253-263.
Kort, S. et al., "Minimally invasive aortic valve replacement: Echocardiographic and clinical results". Am. Heart J. (2001) 142:3, 476-481.
Love, C. et al., The Autogenous Tissue Heart Valve: Current Status, Journal of Caridac Surgery, (1991) 6:4, 499-507.
Lutter, G. et al., "Percutaneous aortic valve replacement: An experimental study. I. Studies on implantation," J. of Thoracic and Cardio. Surg. (2002) 123:4, 768-776.
Moulopoulos, S. D. et al., "Catheter-Mounted Aortic Valves," Annals of Thoracic Surg. (1971) 11:5, 423-430.
Paniagua, D. et al., "Percutaneous heart valve in the chronic in vitro testing model". Circulation (2002), 106:e51-e52, American heart Association, Inc.
Paniagua, D. et al., Heart Watch (2004), Spring, 2004 Edition, Texas Heart Institute.
Pavcnik, D. et al., "Percutaneous bioprosthetic venous valve: A long-term study in sheep". J. of Vascular Surg. (2002) 35:3, 598-603.
Phillips, S. J. at al., "A Temporary Catheter-Tip Aortic Valve: Hemodynamic Effects on Experimental Acute Aortic Insufficiency". Annals of Thoracic Surg. (1976) 21:2, 134-136.
Sochman, J. et al., "Percutaneous Transcatheter Aortic Disc Valve Prosthesis Implantation: A Feasibility Study". Cardiovasc. Intervent. Radiol. (2000) 23, 384-388.
Stuart, M., "In Heart Valves, A Brave, New Non-Surgical World". Start-Up (2004) 9-17.
Vahanian, A. et al., "Percutaneous Approaches to Valvular Disease". Circulation (2004) 109, 1572-1579.
Van Herwerden, L. A. et al., "Percutaneous valve implantation: back to the future?" Euro. Heart J. (2002) 23:18, 1415-1416.
Zhou, J. Q. et al., "Self-expandable valved stent of large size: off-bypass implantation in pulmonary position". Eur. J. Cardiothorac. (2003) 24, 212-216.
Haug et al.; U.S. Appl. No. 12/028,452 entitled "Methods and apparatus for endovascularly replacing a patient's heart valve," filed Feb. 8, 2008.
Salahieh, et al., U.S. Appl. No. 12/132,304 entitled "Low profile heart valve and delivery system," filed Jun. 3, 2008.
Paul et al.; U.S. Appl. No. 12/578,463 entitled "Medical Devices and Delivery Systems for Delivering Medical Devices," filed Oct. 13, 2009.
Paul et al.; U.S. Appl. No. 12/578,447 entitled "Medical Devices and Delivery Systems for Delivering Medical Devices," filed Oct. 13, 2009.
Salahieh et al.; U.S. Appl. No. 12/777,161 entitled "Two-Part Package for Medical Implant," filed May 10, 2010.

* cited by examiner

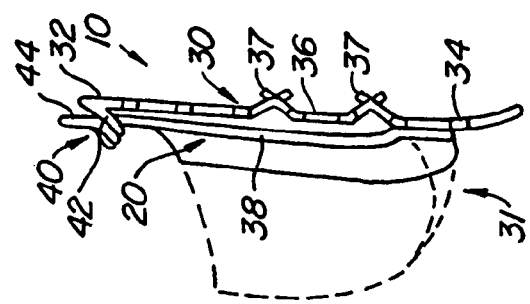
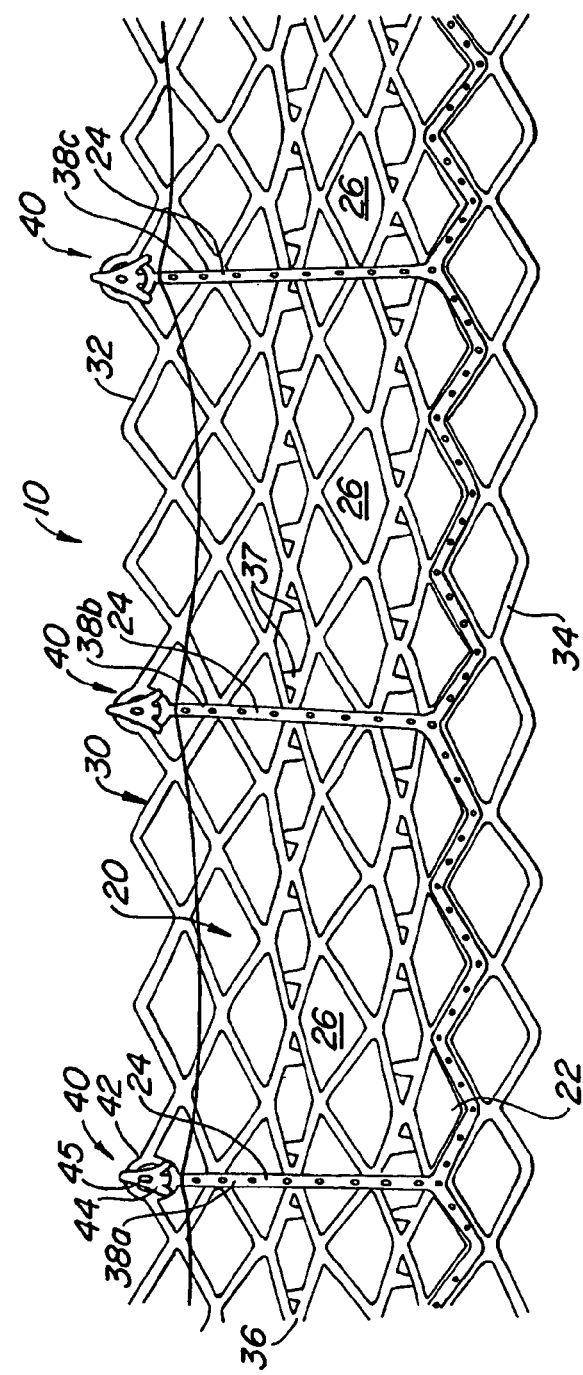

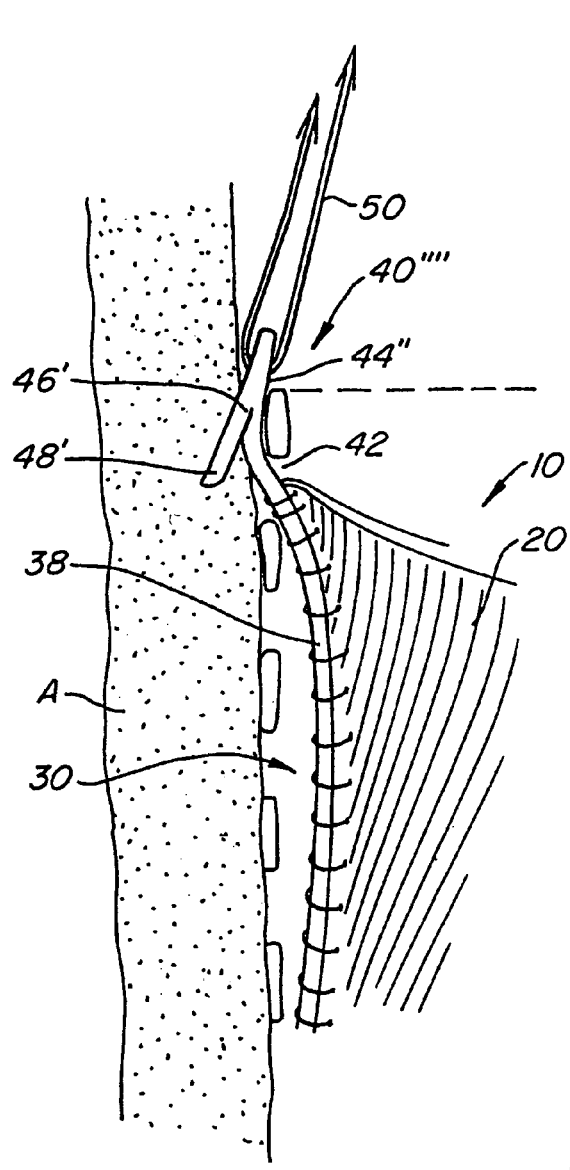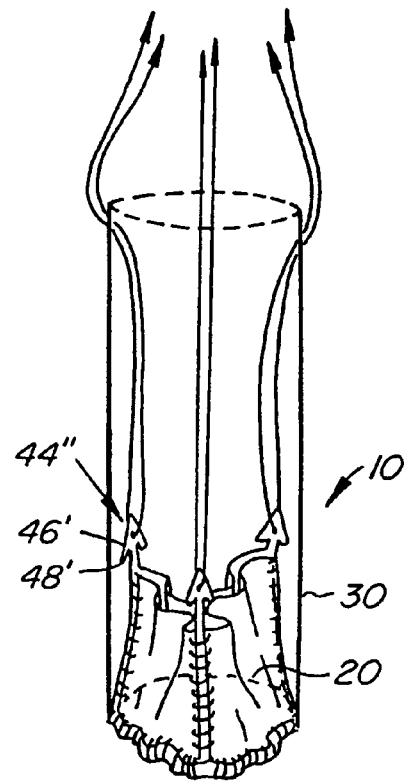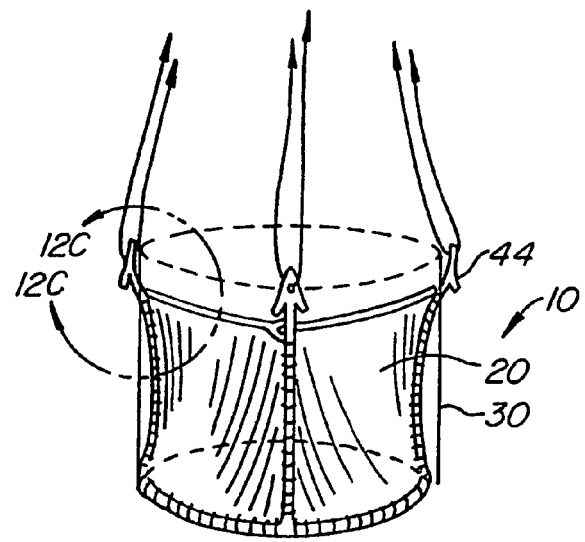
FIG. 12C
FIG. 12A
FIG. 12B

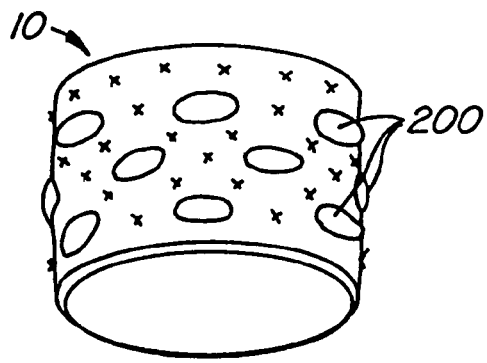
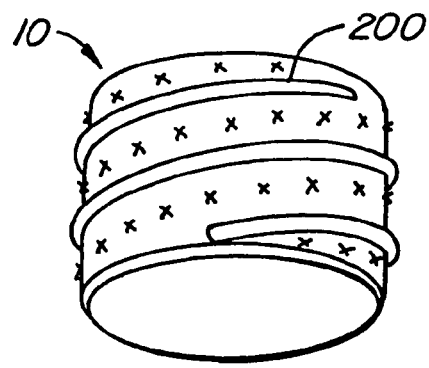
FIG. 15D　　　　　　FIG. 15E
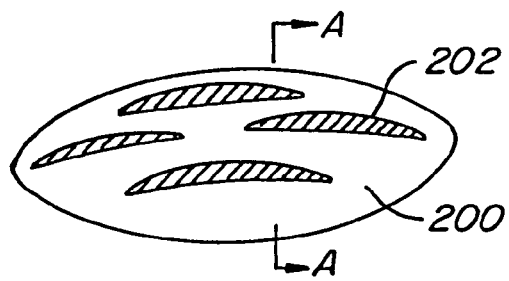
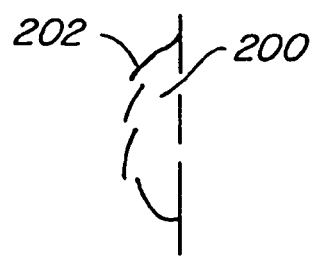
FIG. 16A　　　A-A
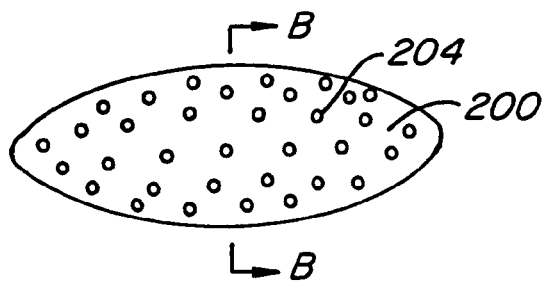
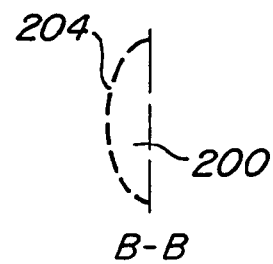
FIG. 16B　　　B-B
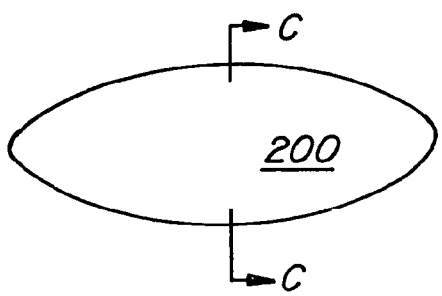
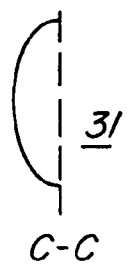
FIG. 16C　　　C-C

REPLACEMENT VALVE AND ANCHOR

CROSS-REFERENCE

This application is a continuation application of Ser. No. 10/746,872, filed Dec. 23, 2003, which is incorporated herein by reference in its entirety and to which application we claim priority under 35 USC §120.

BACKGROUND OF THE INVENTION

The present invention relates to methods and apparatus for endovascularly replacing a heart valve. More particularly, the present invention relates to methods and apparatus for endovascularly replacing a heart valve with a replacement valve using an expandable and retrievable anchor.

Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to synthetic rings that are secured to the patient's heart.

Valve replacement surgery is a highly invasive operation with significant concomitant risk. Risks include bleeding, infection, stroke, heart attack, arrhythmia, renal failure, adverse reactions to the anesthesia medications, as well as sudden death. 2-5% of patients die during surgery.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in minimally invasive surgery and interventional cardiology have encouraged some investigators to pursue percutaneous replacement of the aortic heart valve. Percutaneous Valve Technologies ("PVT") of Fort Lee, N.J., has developed a balloon-expandable stent integrated with a bioprosthetic valve. The stent/valve device is deployed across the native diseased valve to permanently hold the valve open, thereby alleviating a need to excise the native valve and to position the bioprosthetic valve in place of the native valve. PVT's device is designed for delivery in a cardiac catheterization laboratory under local anesthesia using fluoroscopic guidance, thereby avoiding general anesthesia and open-heart surgery. The device was first implanted in a patient in April of 2002.

PVT's device suffers from several drawbacks. Deployment of PVT's stent is not reversible, and the stent is not retrievable. This is a critical drawback because improper positioning too far up towards the aorta risks blocking the coronary ostia of the patient. Furthermore, a misplaced stent/valve in the other direction (away from the aorta, closer to the ventricle) will impinge on the mitral apparatus and eventually wear through the leaflet as the leaflet continuously rubs against the edge of the stent/valve.

Another drawback of the PVT device is its relatively large cross-sectional delivery profile. The PVT system's stent/valve combination is mounted onto a delivery balloon, making retrograde delivery through the aorta challenging. An antegrade transseptal approach may therefore be needed, requiring puncture of the septum and routing through the mitral valve, which significantly increases complexity and risk of the procedure. Very few cardiologists are currently trained in performing a transseptal puncture, which is a challenging procedure by itself.

Other prior art replacement heart valves use self-expanding stents as anchors. In the endovascular aortic valve replacement procedure, accurate placement of aortic valves relative to coronary ostia and the mitral valve is critical. Standard self-expanding systems have very poor accuracy in deployment, however. Often the proximal end of the stent is not released from the delivery system until accurate placement is verified by fluoroscopy, and the stent typically jumps once released. It is therefore often impossible to know where the ends of the stent will be with respect to the native valve, the coronary ostia and the mitral valve.

Also, visualization of the way the new valve is functioning prior to final deployment is very desirable. Visualization prior to final and irreversible deployment cannot be done with standard self-expanding systems, however, and the replacement valve is often not fully functional before final deployment.

Another drawback of prior art self-expanding replacement heart valve systems is their lack of radial strength. In order for self-expanding systems to be easily delivered through a delivery sheath, the metal needs to flex and bend inside the delivery catheter without being plastically deformed. In arterial stents, this is not a challenge, and there are many commercial arterial stent systems that apply adequate radial force against the vessel wall and yet can collapse to a small enough of a diameter to fit inside a delivery catheter without plastically deforming. However when the stent has a valve fastened inside it, as is the case in aortic valve replacement, the anchoring of the stent to vessel walls is significantly challenged during diastole. The force to hold back arterial pressure and prevent blood from going back inside the ventricle during diastole will be directly transferred to the stent/vessel wall interface. Therefore the amount of radial force required to keep the self expanding stent/valve in contact with the vessel wall and not sliding will be much higher than in stents that do not have valves inside of them. Moreover, a self-expanding stent without sufficient radial force will end up dilating and contracting with each heartbeat, thereby distorting the valve, affecting its function and possibly migrating and dislodging completely. Simply increasing strut thickness of the self-expanding stent is not a practical solution as it runs the risk of larger profile and/or plastic deformation of the self-expanding stent.

U.S. patent application Ser. No. 2002/0151970 to Garrison et al. describes a two-piece device for replacement of the aortic valve that is adapted for delivery through a patient's aorta. A stent is endovascularly placed across the native valve, then a replacement valve is positioned within the lumen of the stent. By separating the stent and the valve during delivery, a profile of the device's delivery system may be sufficiently reduced to allow aortic delivery without requiring a transseptal approach. Both the stent and a frame of the replacement valve may be balloon-expandable or self-expanding.

While providing for an aortic approach, devices described in the Garrison patent application suffer from several drawbacks. First, the stent portion of the device is delivered across the native valve as a single piece in a single step, which precludes dynamic repositioning of the stent during delivery. Stent foreshortening or migration during expansion may lead to improper alignment.

Additionally, Garrison's stent simply crushes the native valve leaflets against the heart wall and does not engage the leaflets in a manner that would provide positive registration of the device relative to the native position of the valve. This increases an immediate risk of blocking the coronary ostia, as well as a longer-term risk of migration of the device post-implantation. Further still, the stent comprises openings or gaps in which the replacement valve is seated post-delivery. Tissue may protrude through these gaps, thereby increasing a risk of improper seating of the valve within the stent.

In view of drawbacks associated with previously known techniques for endovascularly replacing a heart valve, it would be desirable to provide methods and apparatus that overcome those drawbacks.

SUMMARY OF THE INVENTION

One aspect of the invention provides an apparatus for endovascularly replacing a patient's heart valve, including: a replacement valve adapted to be delivered endovascularly to a vicinity of the heart valve; an expandable anchor adapted to be delivered endovascularly to the vicinity of the heart valve; and a lock mechanism configured to maintain a minimum amount of anchor expansion. The lock mechanism may include first and second mating interlocking elements. An actuator may be provided to apply an actuation force on the anchor.

Another aspect of the invention provides a method for endovascularly replacing a patient's heart valve. In some embodiments the method includes the steps of: endovascularly delivering a replacement valve and an expandable anchor to a vicinity of the heart valve; expanding the anchor to a deployed configuration; and locking the anchor in the deployed configuration.

Yet another aspect of the invention provides an apparatus for endovascularly replacing a patient's heart valve, including: an anchor comprising a lip region and a skirt region; a replacement valve coupled to the anchor; and a lock, wherein the lip region and skirt region are configured for percutaneous expansion to engage the patient's heart valve, and wherein the lock is configured to maintain such expansion.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-B are elevational views of a replacement heart valve and anchor according to one embodiment of the invention.

FIGS. 2A-B are sectional views of the anchor and valve of FIG. 1.

FIGS. 12A-C show a vessel wall engaging lock for use with replacement heart valves and anchors of this invention.

FIGS. 15A-E show alternative arrangements of seals on a replacement heart valve and anchor.

FIGS. 16A-C show alternative seal designs for use with replacement heart valves and anchors.

DETAILED DESCRIPTION OF THE INVENTION

Figure 1A:
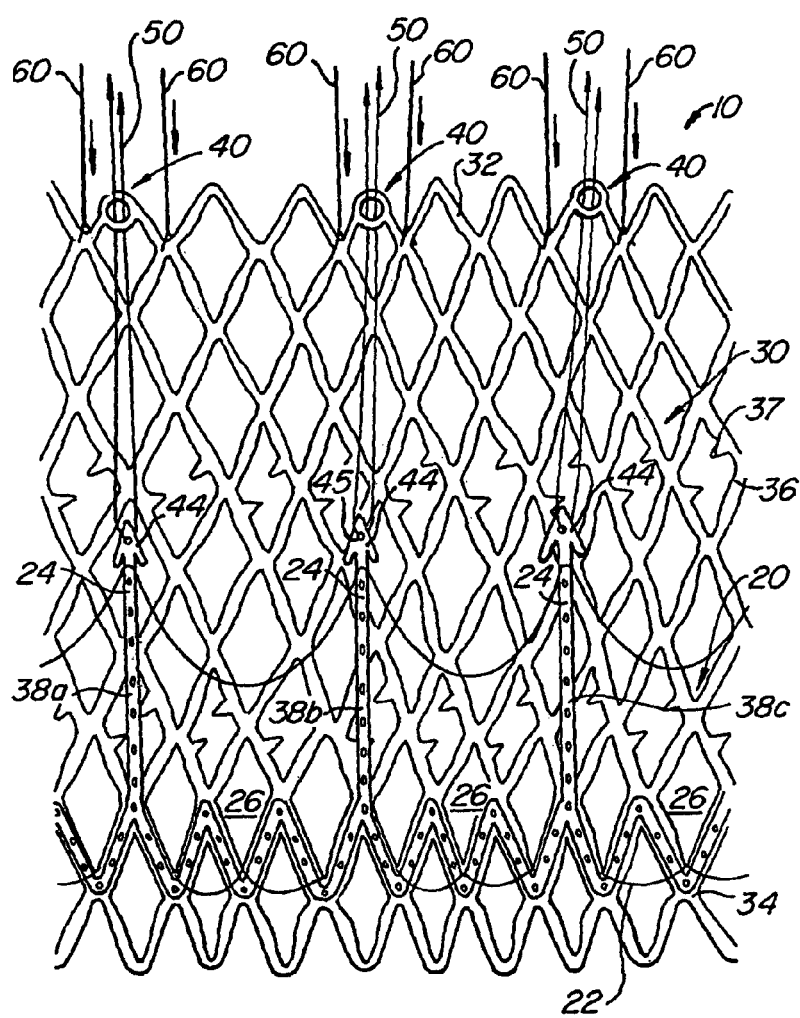

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

With reference now to FIGS. 1-4, a first embodiment of replacement heart valve apparatus in accordance with the present invention is described, including a method of actively foreshortening and expanding the apparatus from a delivery configuration and to a deployed configuration. Apparatus 10 comprises replacement valve 20 disposed within and coupled to anchor 30. FIG. 1 schematically illustrate individual cells of anchor 30 of apparatus 10, and should be viewed as if the cylindrical anchor has been cut open and laid flat. FIG. 2 schematically illustrate a detail portion of apparatus 10 in side-section.

Anchor 30 has a lip region 32, a skirt region 34 and a body region 36. First, second and third posts 38a, 38b and 38c, respectively, are coupled to skirt region 34 and extend within lumen 31 of anchor 30. Posts 38 preferably are spaced 120° apart from one another about the circumference of anchor 30.

Anchor 30 preferably is fabricated by using self-expanding patterns (laser cut or chemically milled), braids and materials, such as a stainless steel, nickel-titanium ("Nitinol") or cobalt chromium but alternatively may be fabricated using balloon-expandable patterns where the anchor is designed to plastically deform to it's final shape by means of balloon expansion. Replacement valve 20 is preferably from biologic tissues, e.g. porcine valve leaflets or bovine or equine pericardium tissues, alternatively it can be made from tissue engineered materials (such as extracellular matrix material from Small Intestinal Submucosa (SIS)) but alternatively may be prosthetic from an elastomeric polymer or silicone, Nitinol or stainless steel mesh or pattern (sputtered, chemically milled or laser cut). The leaflet may also be made of a composite of the elastomeric or silicone materials and metal alloys or other fibers such Kevlar or carbon. Annular base 22 of replacement valve 20 preferably is coupled to skirt region 34 of anchor 30, while commissures 24 of replacement valve leaflets 26 are coupled to posts 38.

Anchor 30 may be actuated using external non-hydraulic or non-pneumatic force to actively foreshorten in order to increase its radial strength. As shown below, the proximal and distal end regions of anchor 30 may be actuated independently. The anchor and valve may be placed and expanded in order to visualize their location with respect to the native valve and other anatomical features and to visualize operation of the valve. The anchor and valve may thereafter be repositioned and even retrieved into the delivery sheath or catheter. The apparatus may be delivered to the vicinity of the patient's aortic valve in a retrograde approach in a catheter having a diameter no more than 23 french, preferably no more than 21 french, more preferably no more than 19 french, or more preferably no more than 17 french. Upon deployment the anchor and replacement valve capture the native valve leaflets and positively lock to maintain configuration and position.

A deployment tool is used to actuate, reposition, lock and/or retrieve anchor 30. In order to avoid delivery of anchor 30 on a balloon for balloon expansion, a non-hydraulic or non-pneumatic anchor actuator is used. In this embodiment, the actuator is a deployment tool that includes distal region control wires 50, control rods or tubes 60 and proximal region control wires 62. Locks 40 include posts or arms 38 preferably with male interlocking elements 44 extending from skirt region 34 and mating female interlocking elements 42 in lip region 32. Male interlocking elements 44 have eyelets 45. Control wires 50 pass from a delivery system for apparatus 10 through female interlocking elements 42, through eyelets 45 of male interlocking elements 44, and back through female interlocking elements 42, such that a double strand of wire 50 passes through each female interlocking element 42 for manipulation by a medical practitioner external to the patient to actuate and control the anchor by changing the anchor's shape. Control wires 50 may comprise, for example, strands of suture.

Tubes 60 are reversibly coupled to apparatus 10 and may be used in conjunction with wires 50 to actuate anchor 30, e.g., to foreshorten and lock apparatus 10 in the fully deployed configuration. Tubes 60 also facilitate repositioning and retrieval of apparatus 10, as described hereinafter. For example, anchor 30 may be foreshortened and radially expanded by applying a distally directed force on tubes 60 while proximally retracting wires 50. As seen in FIG. 3, control wires 62 pass through interior lumens 61 of tubes 60. This ensures that tubes 60 are aligned properly with apparatus 10 during deployment and foreshortening. Control wires 62 can also actuate anchor 60; proximally directed forces on control wires 62 contacts the proximal lip region 32 of anchor 30. Wires 62 also act to couple and decouple tubes 60 from apparatus 10. Wires 62 may comprise, for example, strands of suture.

Figure 2A:
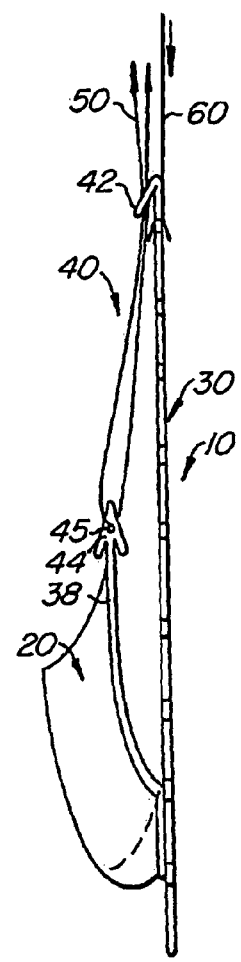

FIGS. 1A and 2A illustrate anchor 30 in a delivery configuration or in a partially deployed configuration (e.g., after dynamic self-expansion expansion from a constrained delivery configuration within a delivery sheath). Anchor 30 has a relatively long length and a relatively small width in the delivery or partially deployed configuration, as compared to the foreshortened and fully deployed configuration of FIGS. 1B and 2B.

In FIGS. 1A and 2A, replacement valve 20 is collapsed within lumen 31 of anchor 30. Retraction of wires 50 relative to tubes 60 foreshortens anchor 30, which increases the anchor's width while decreasing its length. Such foreshortening also properly seats replacement valve 20 within lumen 31 of anchor 30. Imposed foreshortening will enhance radial force applied by apparatus 10 to surrounding tissue over at least a portion of anchor 30. In some embodiments, the anchor exerts an outward force on surrounding tissue to engage the tissue in such way to prevent migration of anchor caused by force of blood against closed leaflet during diastole. This anchoring force is preferably 1 to 2 lbs, more preferably 2 to 4 lbs, or more preferably 4 to 10 lbs. In other embodiments, the anchoring force is preferably greater than 1 pound, more preferably greater than 2 pounds, or more preferably greater than 4 pounds. Enhanced radial force of the anchor is also important for enhanced crush resistance of the anchor against the surrounding tissue due to the healing response (fibrosis and contraction of annulus over a longer period of time) or to dynamic changes of pressure and flow at each heart beat In an alternative embodiment, the anchor pattern or braid is designed to have gaps or areas where the native tissue is allowed to protrude through the anchor slightly (not shown) and as the foreshortening is applied, the tissue is trapped in the anchor. This feature would provide additional means to prevent anchor migration and enhance long term stability of the device.

Deployment of apparatus 10 is fully reversible until lock 40 has been locked via mating of male interlocking elements 44 with female interlocking elements 42. Deployment is then completed by decoupling tubes 60 from lip section 32 of anchor 30 by retracting one end of each wire 62 relative to the other end of the wire, and by retracting one end of each wire 50 relative to the other end of the wire until each wire has been removed from eyelet 45 of its corresponding male interlocking element 44.

As best seen in FIG. 2B, body region 36 of anchor 30 optionally may comprise barb elements 37 that protrude from anchor 30 in the fully deployed configuration, for example, for engagement of a patient's native valve leaflets and to preclude migration of the apparatus.

Figure 3A:
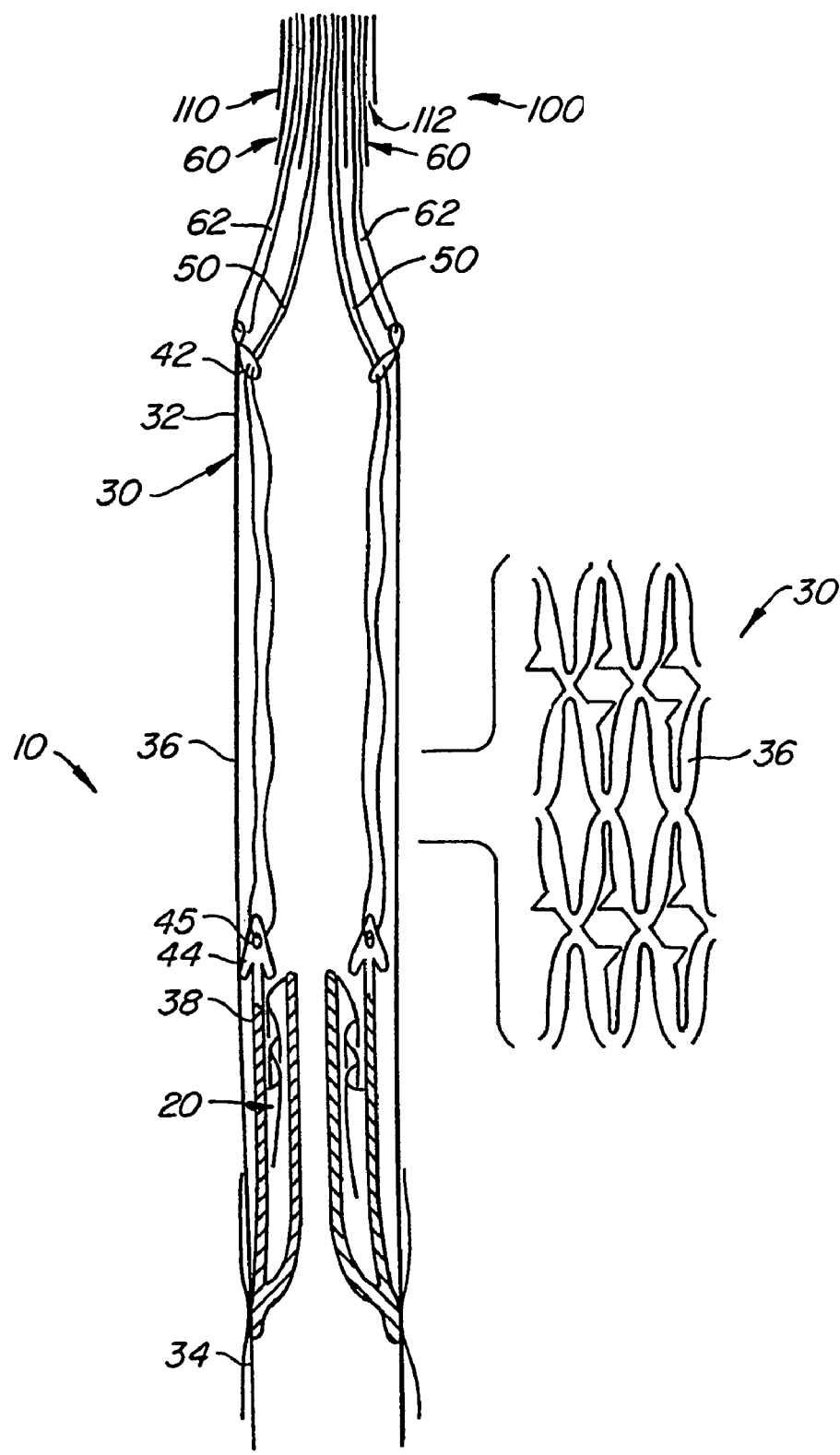
FIGS. 3A-B show delivery and deployment of a replacement heart valve and anchor, such as the anchor and valve of FIGS. 1 and 2.
Figure 3B:
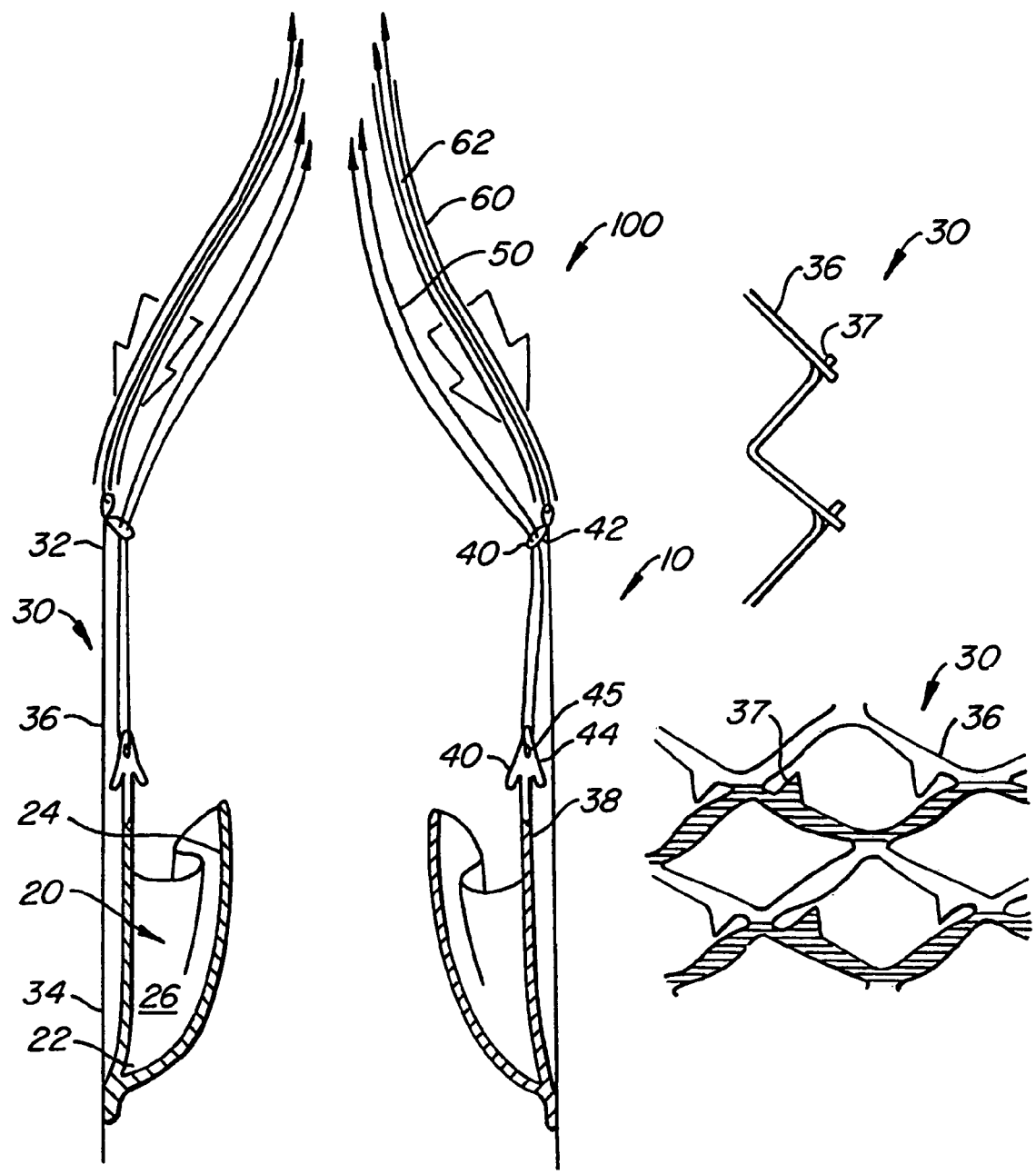

With reference now to FIG. 3, a delivery and deployment system for a self-expanding embodiment of apparatus 10 including a sheath 110 having a lumen 112. Self-expanding anchor 30 is collapsible to a delivery configuration within lumen 112 of sheath 110, such that apparatus 10 may be delivered via delivery system 100. As seen in FIG. 3A, apparatus 10 may be deployed from lumen 112 by retracting sheath 110 relative to apparatus 10, control wires 50 and tubes 60, which causes anchor 30 to dynamically self-expand to a partially deployed configuration. Control wires 50 then are retracted relative to apparatus 10 and tubes 60 to impose foreshortening upon anchor 30, as seen in FIG. 3B.

During foreshortening, tubes 60 push against lip region 32 of anchor 30, while wires 50 pull on posts 38 of the anchor. Wires 62 may be retracted along with wires 50 to enhance the distally-directed pushing force applied by tubes 60 to lip region 32. Continued retraction of wires 50 relative to tubes 60 would lock locks 40 and fully deploy apparatus 10 with replacement valve 20 properly seated within anchor 30, as in FIGS. 1B and 2B. Apparatus 10 comprises enhanced radial strength in the fully deployed configuration as compared to the partially deployed configuration of FIG. 3A. Once apparatus 10 has been fully deployed, wires 50 and 62 may be removed from apparatus 10, thereby separating delivery system 100 and tubes 60 from the apparatus.

Deployment of apparatus 10 is fully reversible until locks 40 have been actuated. For example, just prior to locking the position of the anchor and valve and the operation of the valve may be observed under fluoroscopy. If the position needs to be changed, by alternately relaxing and reapplying the proximally directed forces exerted by control wires 50 and/or control wires 62 and the distally directed forces exerted by tubes 60, expansion and contraction of the lip and skirt regions of anchor 30 may be independently controlled so that the anchor and valve can be moved to, e.g., avoid blocking the coronary ostia or impinging on the mitral valve. Apparatus 10 may also be completely retrieved within lumen 112 of sheath 110 by simultaneously proximally retracting wires 50 and tubes 60/wires 62 relative to sheath 110. Apparatus 10 then may be removed from the patient or repositioned for subsequent redeployment.

Referring now to FIG. 4, step-by-step deployment of apparatus 10 via delivery system 100 is described. In FIG. 4A, sheath 110 is retracted relative to apparatus 10, wires 50 and tubes 60, thereby causing self-expandable anchor 30 to dynamically self-expand apparatus 10 from the collapsed delivery configuration within lumen 112 of sheath 110 to the partially deployed configuration. Apparatus 10 may then be dynamically repositioned via tubes 60 to properly orient the apparatus, e.g. relative to a patient's native valve leaflets.

Figure 4A:
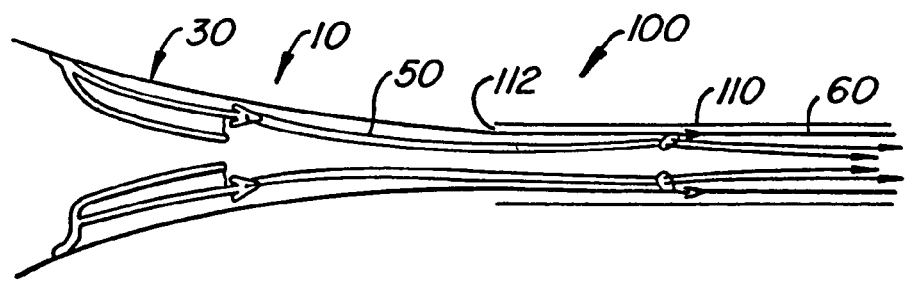
FIGS. 4A-F also show delivery and deployment of a replacement heart valve and anchor, such as the anchor and valve of FIGS. 1 and 2.
Figure 4B:
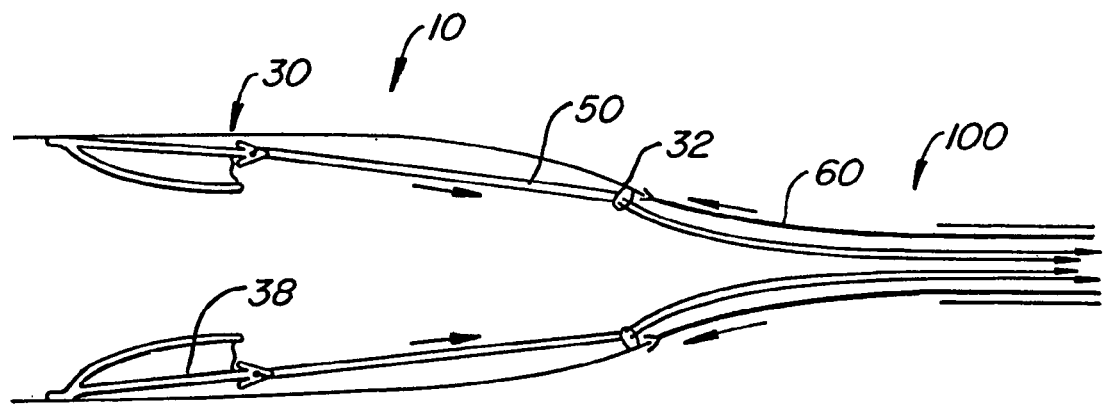
Figure 4C:
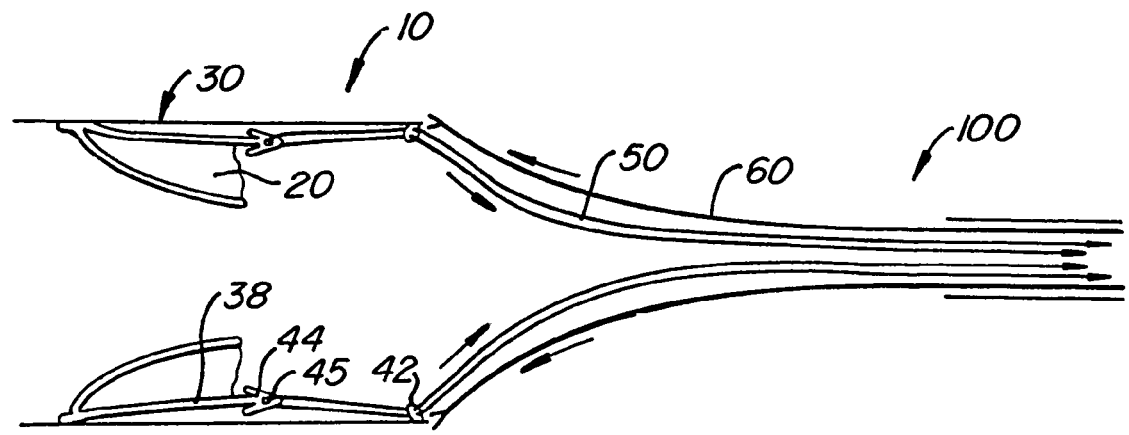

In FIG. 4B, control wires 50 are retracted while tubes 60 are advanced, thereby urging lip region 32 of anchor 30 in a distal direction while urging posts 38 of the anchor in a proximal direction. This foreshortens apparatus 10, as seen in FIG. 4C. Deployment of apparatus 10 is fully reversible even after foreshortening has been initiated and has advanced to the point illustrated in FIG. 4C.

Figure 4D:
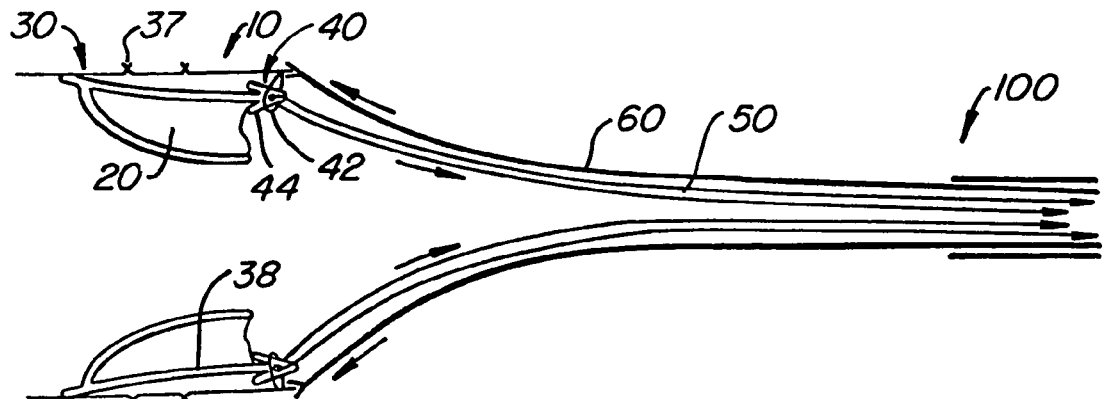
Figure 4E:
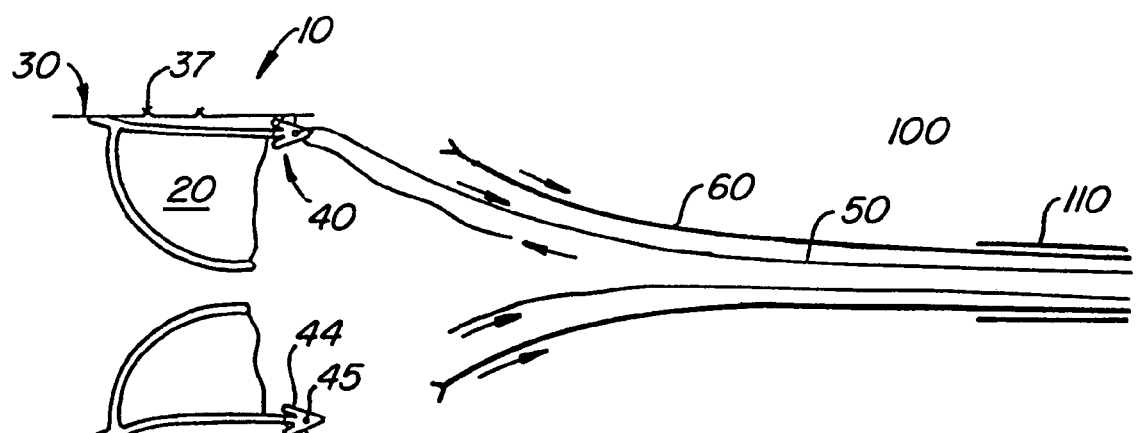
Figure 4F:
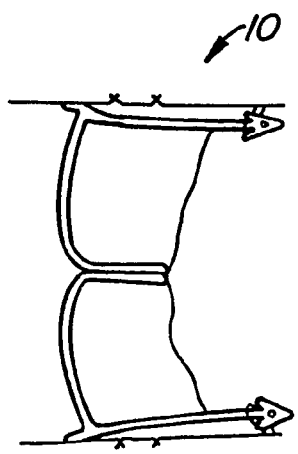

In FIG. 4D, continued foreshortening causes male interlocking elements 44 of locks 40 to engage female interlocking elements 42. The male elements mate with the female elements, thereby locking apparatus 10 in the foreshortened configuration, as seen in FIG. 4E. Wires 50 are then pulled through eyelets 45 of male elements 44 to remove the wires from apparatus 10, and wires 62 are pulled through the proximal end of anchor 30 to uncouple tubes 60 from the apparatus, thereby separating delivery system 100 from apparatus 10. Fully deployed apparatus 10 is shown in FIG. 4F.

Referring to FIG. 5, a method of endovascularly replacing a patient's diseased aortic valve with apparatus 10 and delivery system 100 is described. As seen in FIG. 5A, sheath 110 of delivery system 100, having apparatus 10 disposed therein, is endovascularly advanced over guide wire G, preferably in a retrograde fashion (although an antegrade or hybrid approach alternatively may be used), through a patient's aorta A to the patient's diseased aortic valve AV. A nosecone 102 precedes sheath 110 in a known manner. In FIG. 5B, sheath 110 is positioned such that its distal region is disposed within left ventricle LV of the patient's heart H.

Figure 5A:
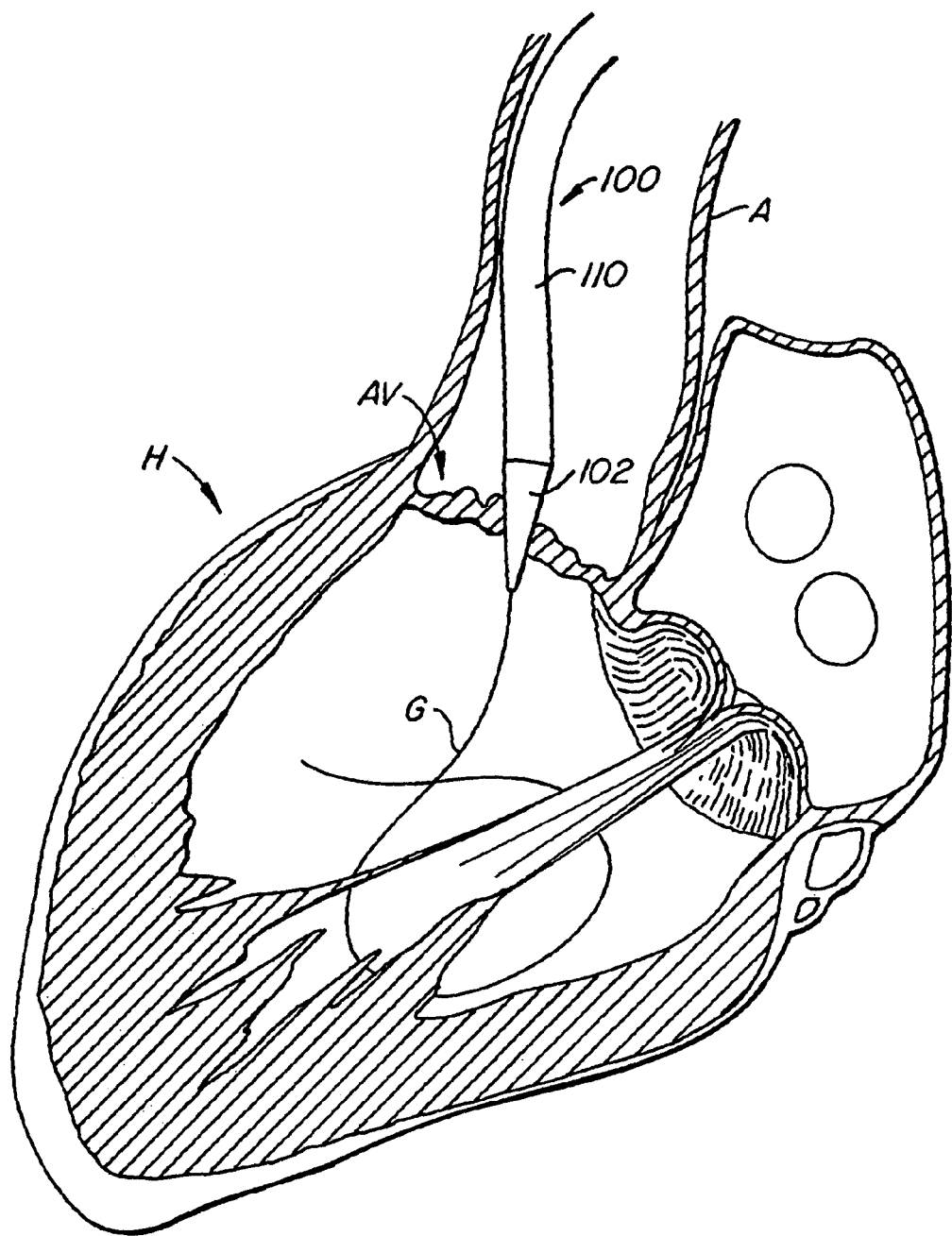
FIGS. 5A-F show the use of a replacement heart valve and anchor to replace an aortic valve.
Figure 5B:
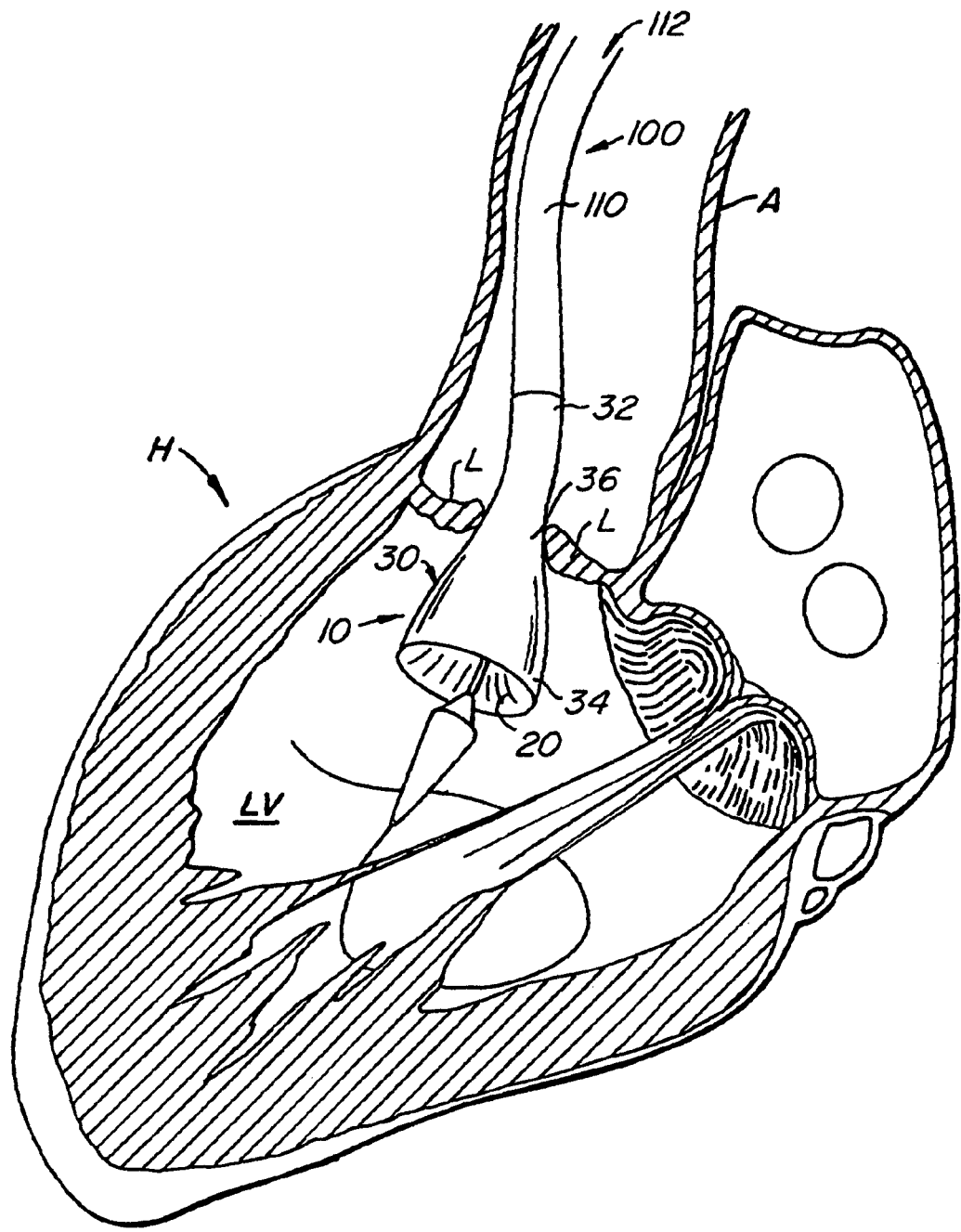
Figure 5C:
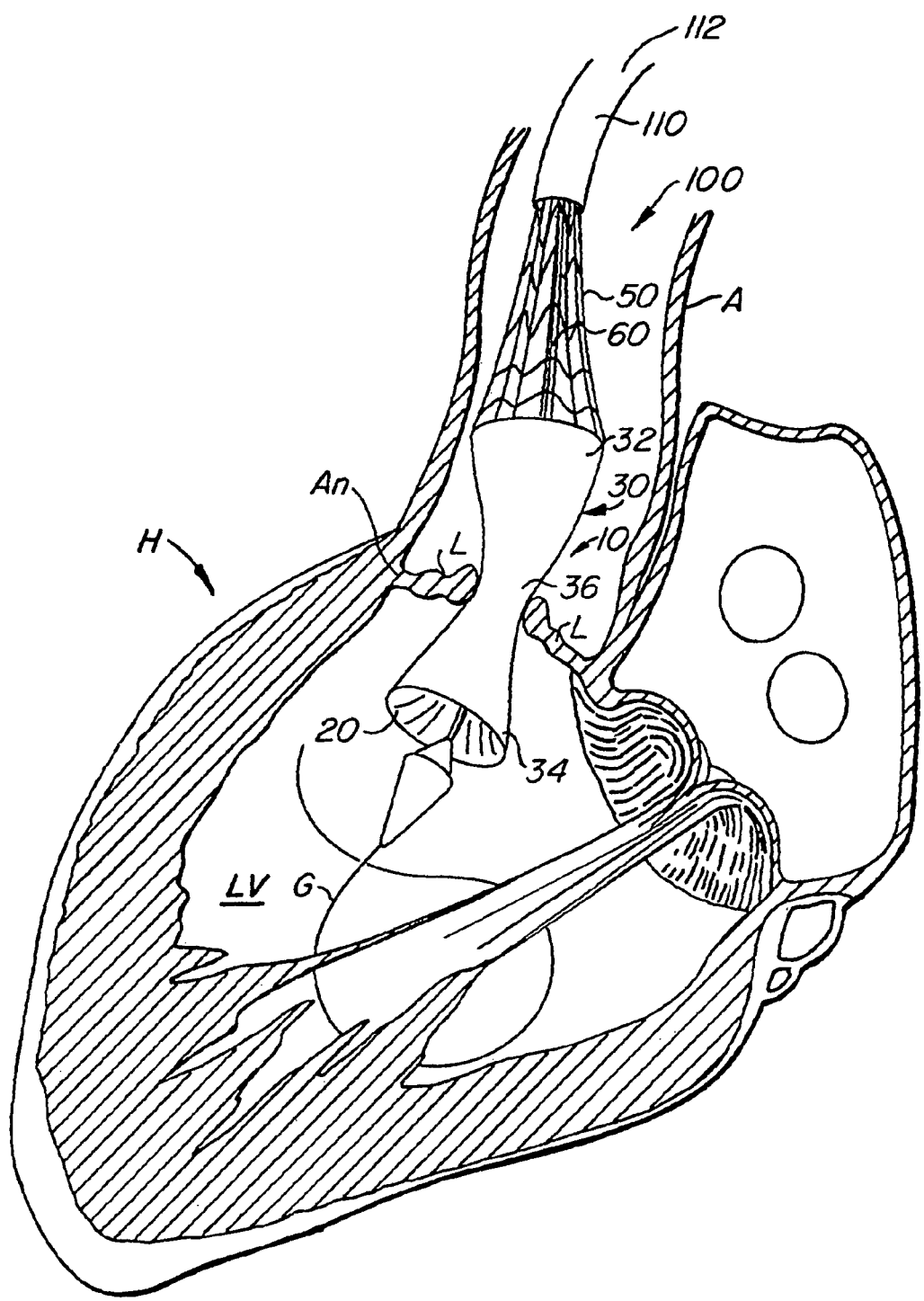

Apparatus 10 is deployed from lumen 112 of sheath 110, for example, under fluoroscopic guidance, such that anchor 30 of apparatus 10 dynamically self-expands to a partially deployed configuration, as in FIG. 5C. Advantageously, apparatus 10 may be retracted within lumen 112 of sheath 110 via wires 50—even after anchor 30 has dynamically expanded to the partially deployed configuration, for example, to abort the procedure or to reposition apparatus 10 or delivery system 100. As yet another advantage, apparatus 10 may be dynamically repositioned, e.g. via sheath 110 and/or tubes 60, in order to properly align the apparatus relative to anatomical landmarks, such as the patient's coronary ostia or the patient's native valve leaflets L. When properly aligned, skirt region 34 of anchor 30 preferably is disposed distal of the leaflets, while body region 36 is disposed across the leaflets and lip region 32 is disposed proximal of the leaflets.

Figure 5D:
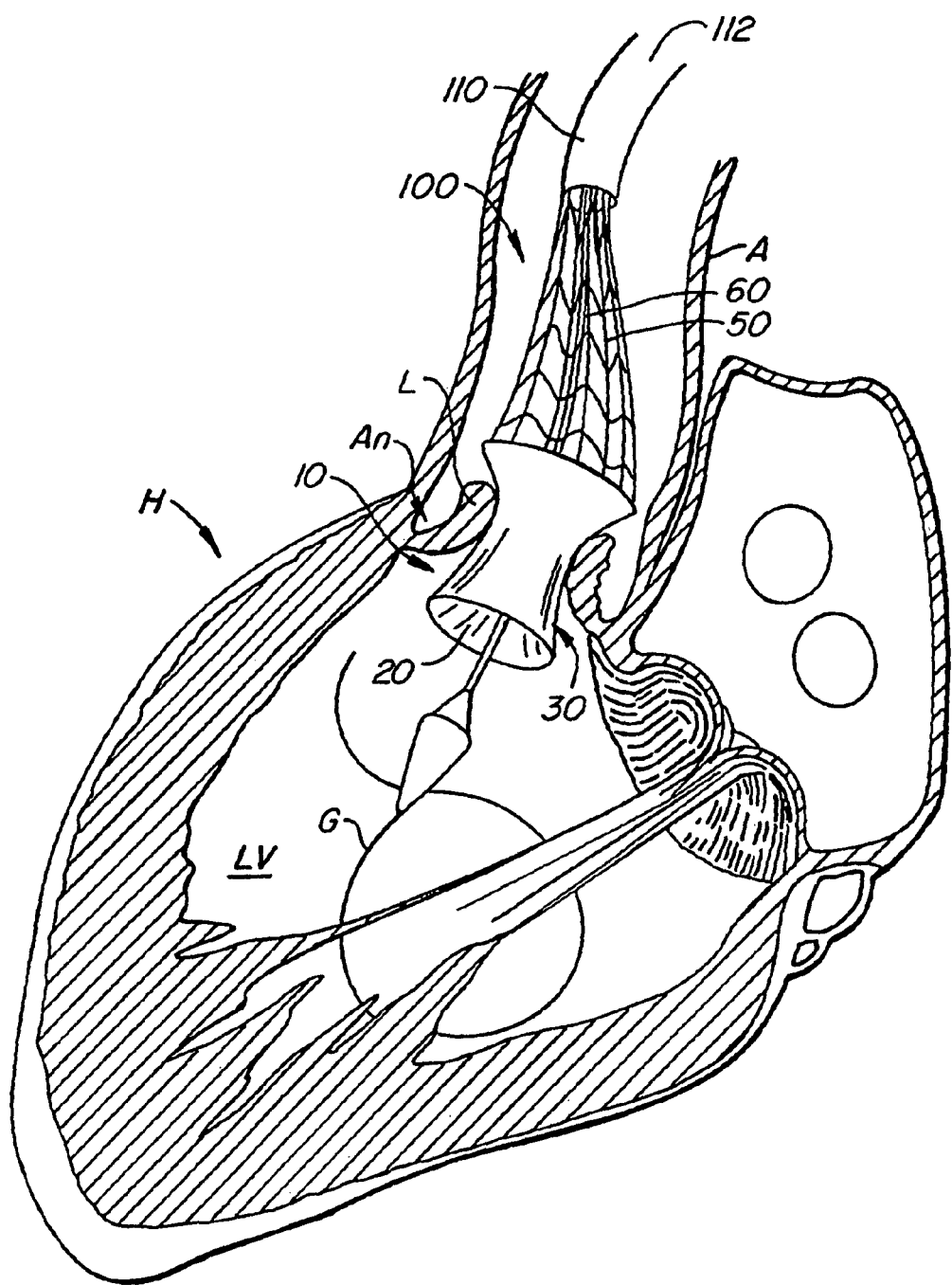
Figure 5E:
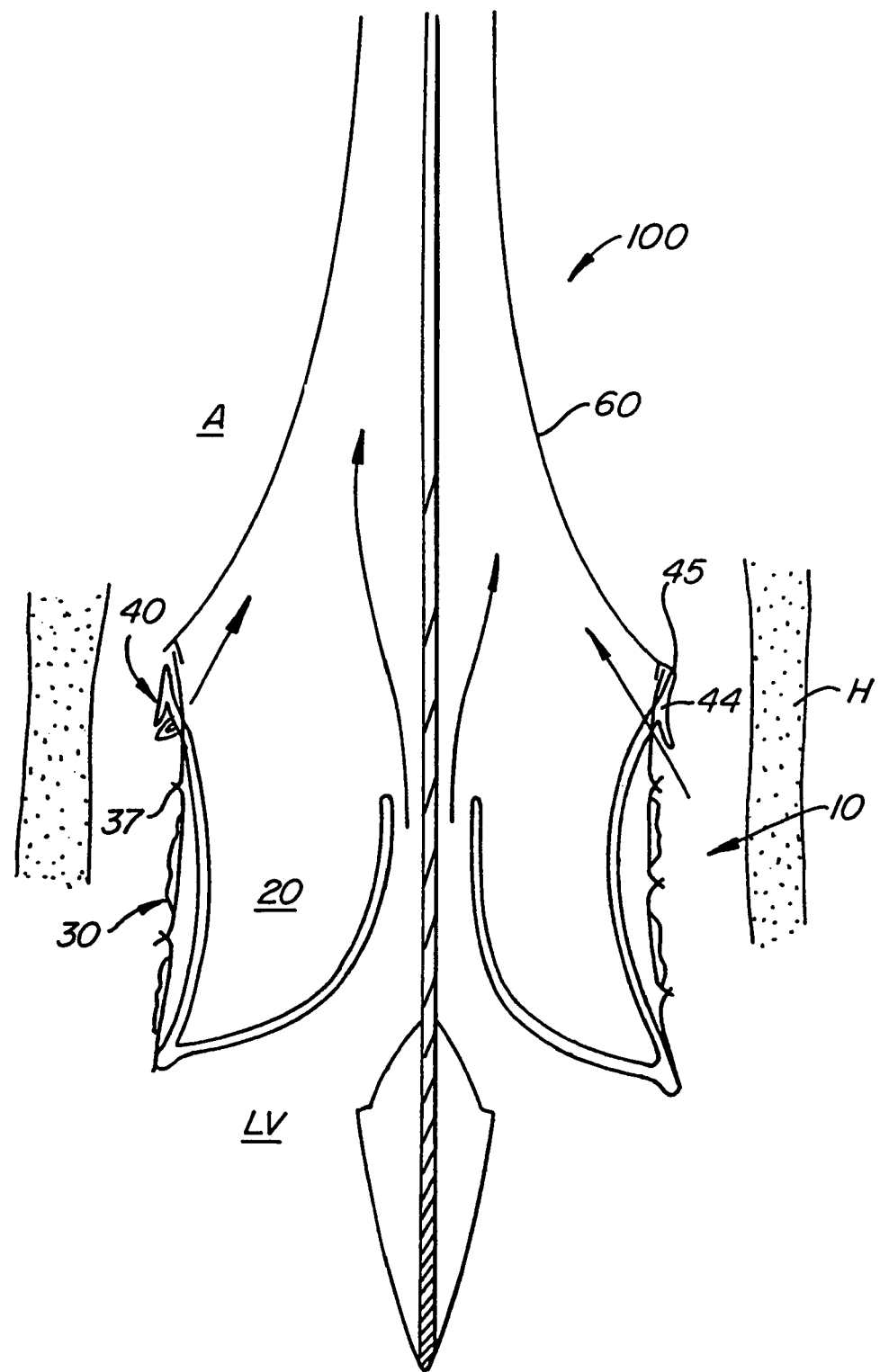

Once properly aligned, wires 50 are retracted relative to tubes 60 to impose foreshortening upon anchor 30 and expand apparatus 10 to the fully deployed configuration, as in FIG. 5D. Foreshortening increases the radial strength of anchor 30 to ensure prolonged patency of valve annulus An, as well as to provide a better seal for apparatus 10 that reduces paravalvular regurgitation. As seen in FIG. 5E, locks 40 maintain imposed foreshortening. Replacement valve 20 is properly seated within anchor 30, and normal blood flow between left ventricle LV and aorta A is thereafter regulated by apparatus 10. Deployment of apparatus 10 advantageously is fully reversible until locks 40 have been actuated.

Figure 5F:
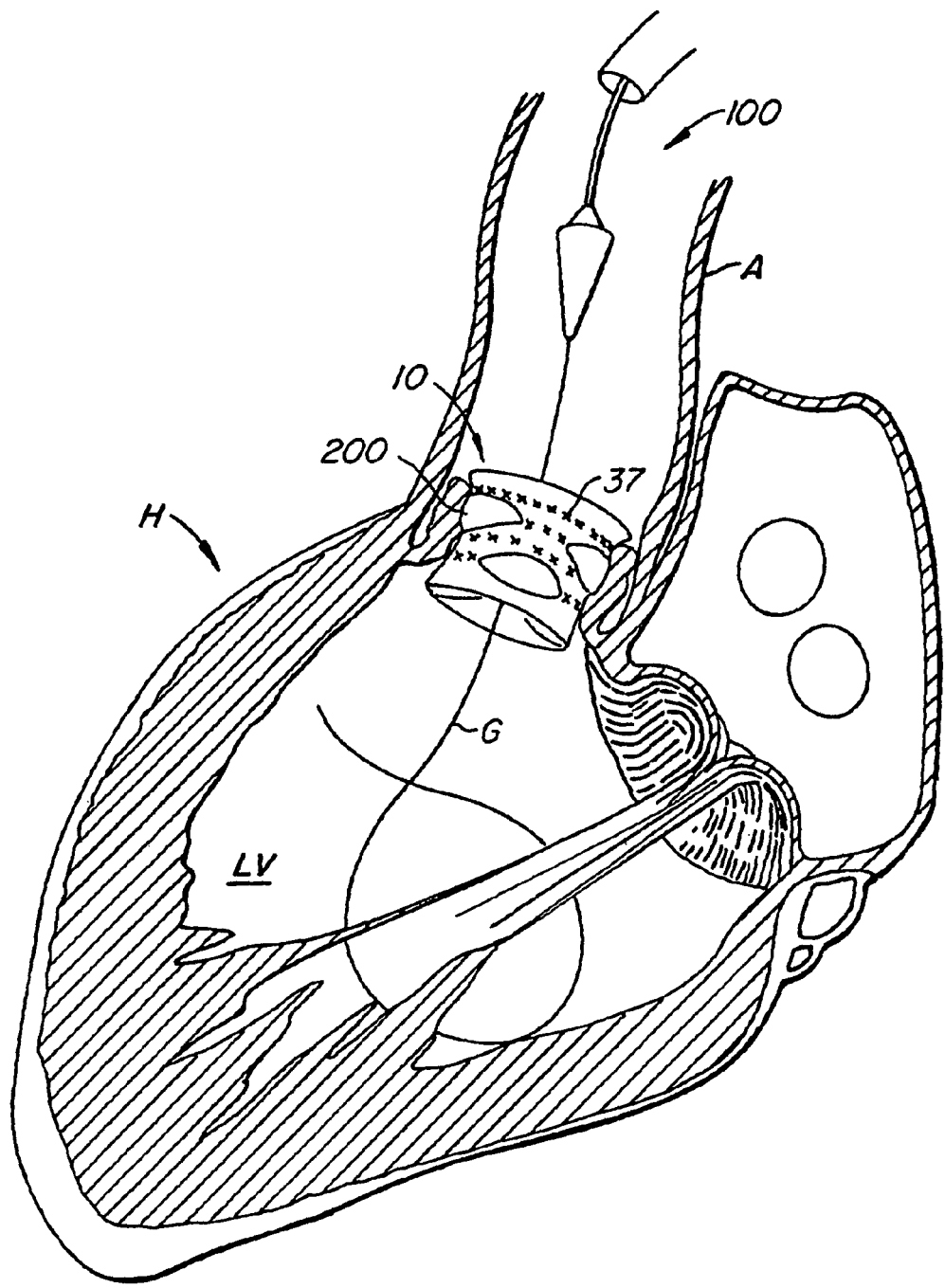

As seen in FIG. 5F, wires 50 are pulled from eyelets 45 of male elements 44 of locks 40, tubes 60 are decoupled from anchor 30, e.g. via wires 62, and delivery system 100 is removed from the patient, thereby completing deployment of apparatus 10. Optional barb elements 37 engage the patient's native valve leaflets, e.g. to preclude migration of the apparatus and/or reduce paravalvular regurgitation.

With reference now to FIG. 6, a method of endovascularly replacing a patient's diseased aortic valve with apparatus 10 is provided, wherein proper positioning of the apparatus is ensured via positive registration of a modified delivery system to the patient's native valve leaflets. In FIG. 6A, modified delivery system 100' delivers apparatus 10 to diseased aortic valve AV within sheath 110. As seen in FIGS. 6B and 6C, apparatus 10 is deployed from lumen 112 of sheath 110, for example, under fluoroscopic guidance, such that anchor 30 of apparatus 10 dynamically self-expands to a partially deployed configuration. As when deployed via delivery system 100, deployment of apparatus 10 via delivery system 100' is fully reversible until locks 40 have been actuated.

Figure 6A:
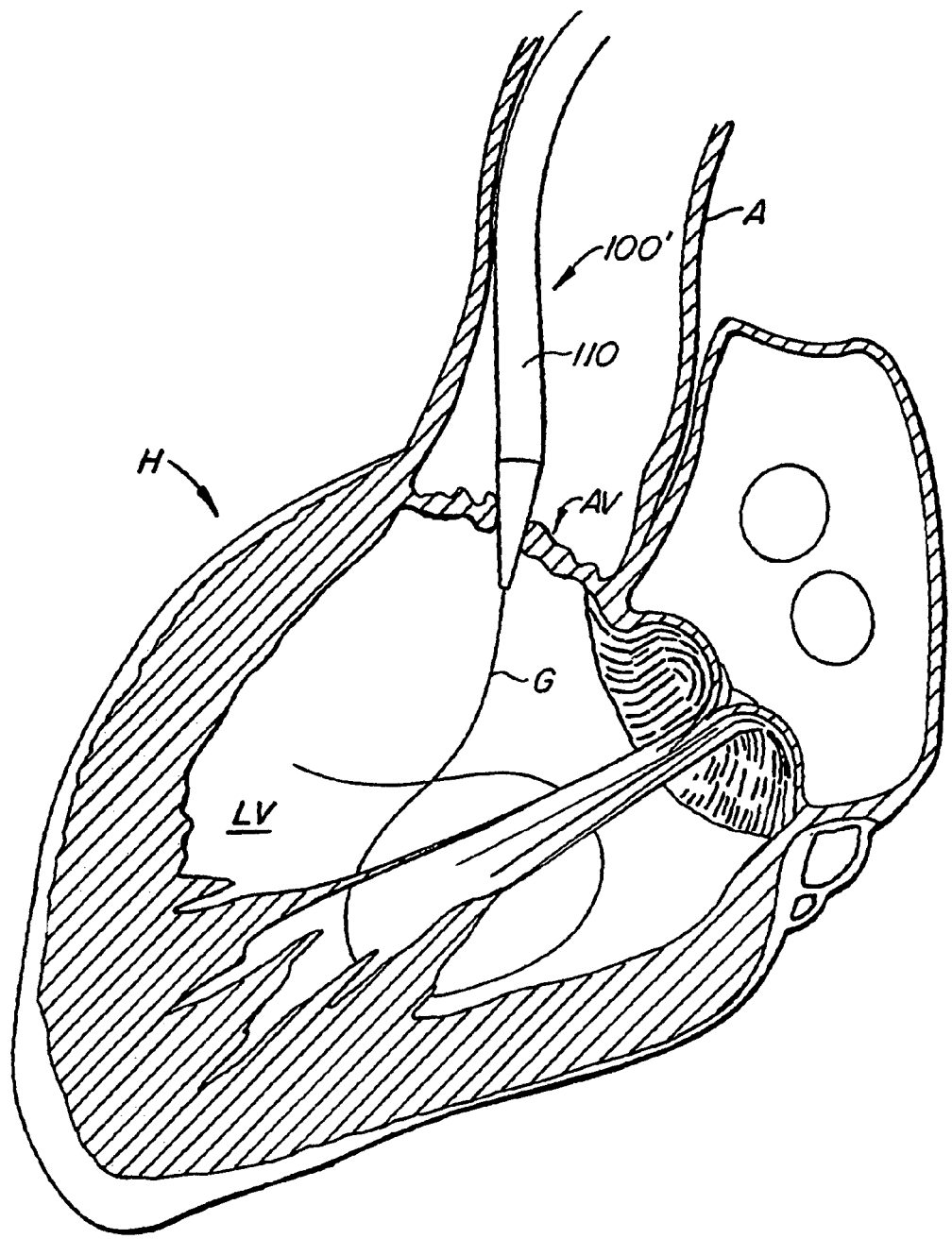
FIGS. 6A-F show the use of a replacement heart valve and anchor with a positive registration feature to replace an aortic valve.
Figure 6B:
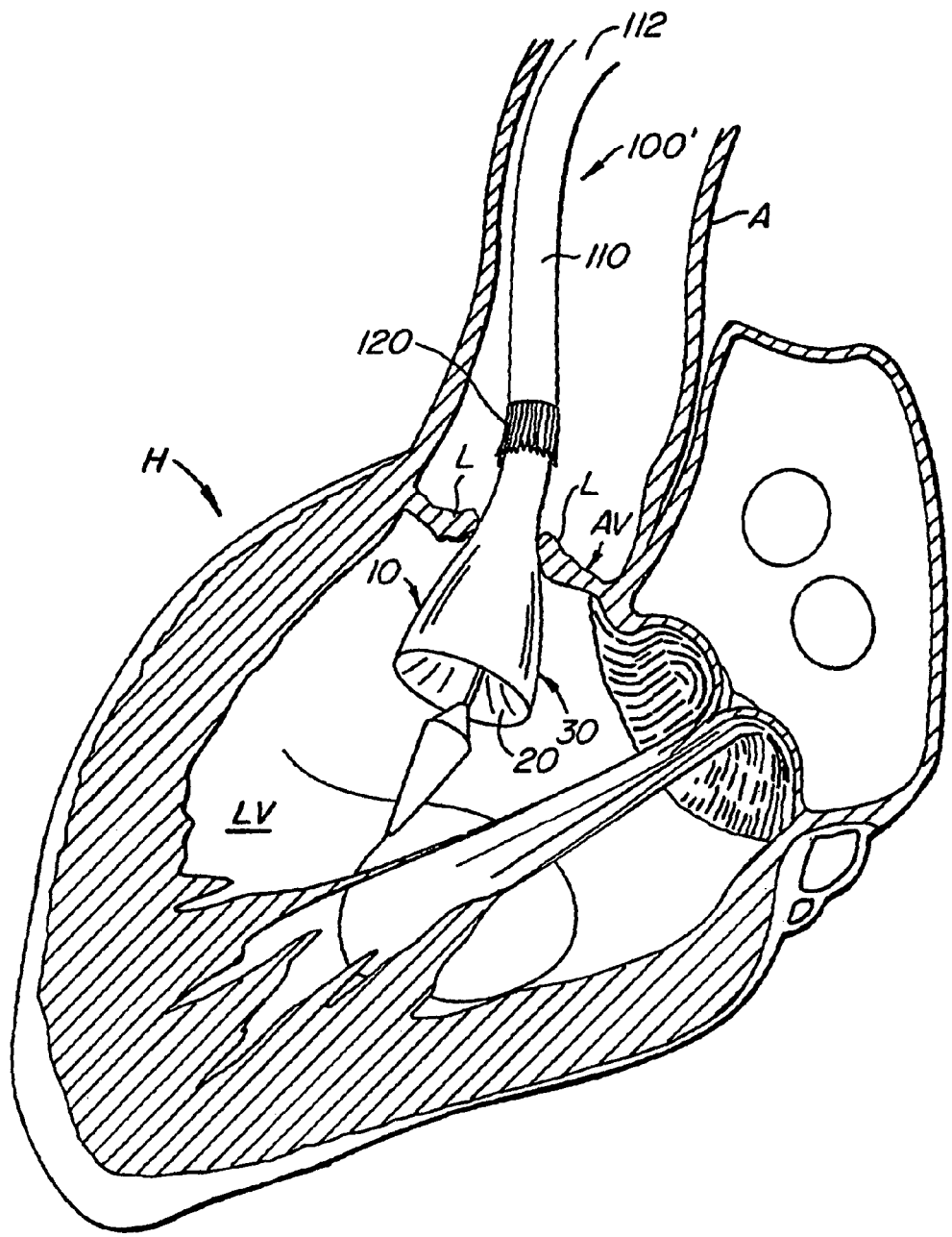
Figure 6C:
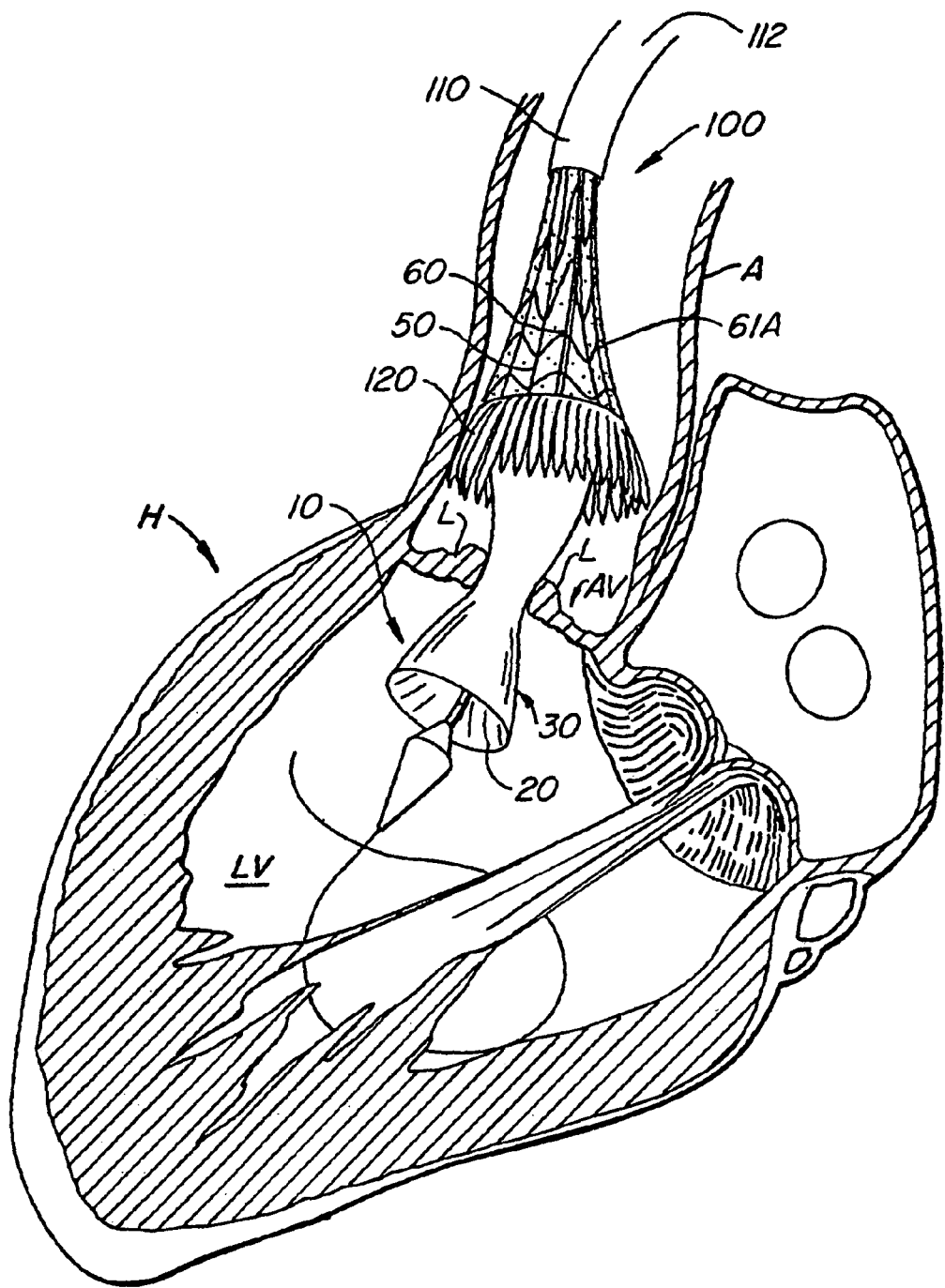

Delivery system 100' comprises leaflet engagement element 120, which preferably self-expands along with anchor 30. Engagement element 120 is disposed between tubes 60 of delivery system 100' and lip region 32 of anchor 30. Element 120 releasably engages the anchor. As seen in FIG. 6C, the element is initially deployed proximal of the patient's native valve leaflets L. Apparatus 10 and element 120 then may be advanced/dynamically repositioned until engagement element positively registers against the leaflets, thereby ensuring proper positioning of apparatus 10. Also delivery system 100' includes filter structure 61A (e.g., filter membrane or braid) as part of push tubes 60 to act as an embolic protection element. Emboli can be generated during manipulation and placement of anchor from either diseased native leaflet or surrounding aortic tissue and can cause blockage. Arrows 61B in FIG. 6E show blood flow through filter structure 61A where blood is allowed to flow but emboli is trapped in the delivery system and removed with it at the end of the procedure.

Figure 6D:
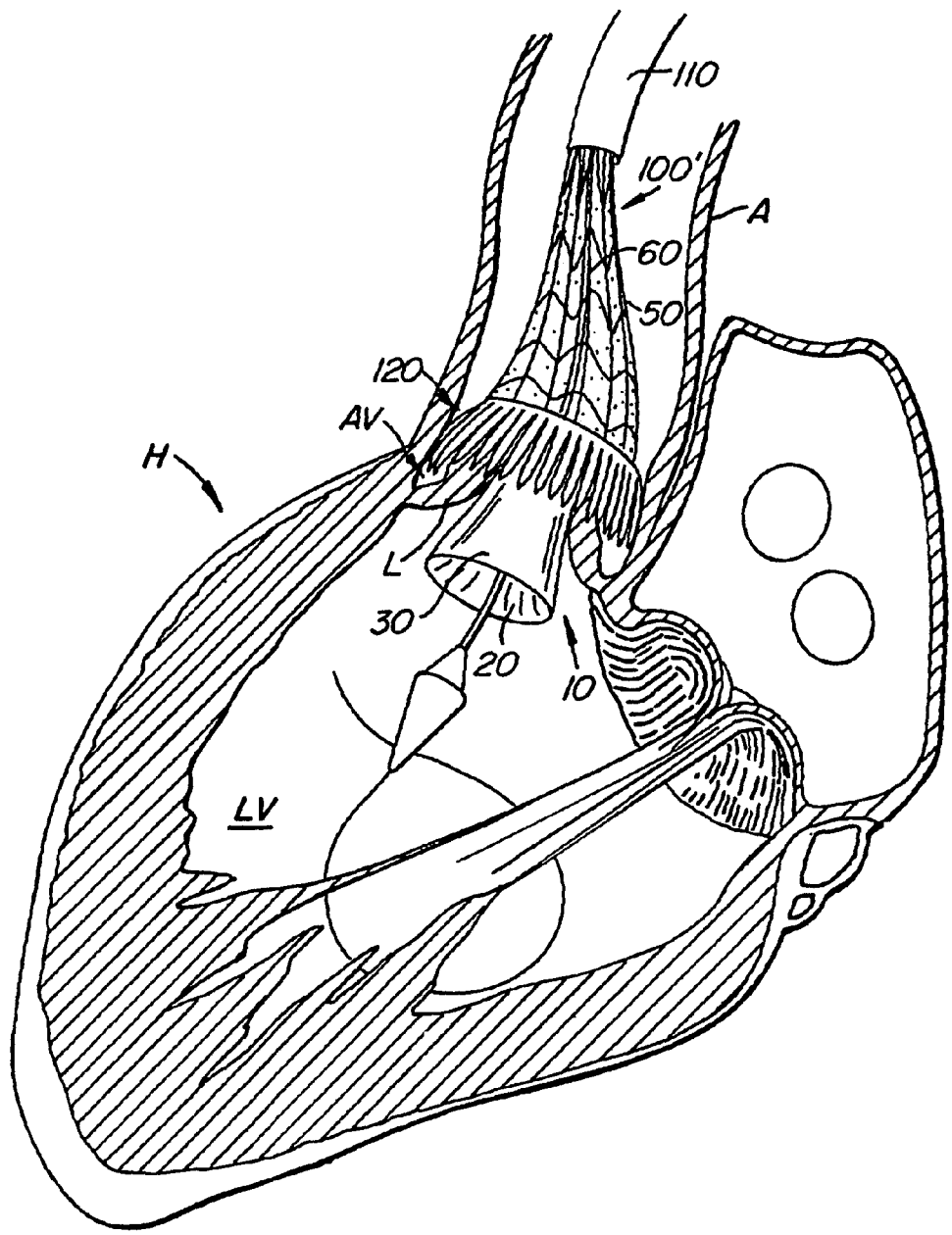
Figure 6E:
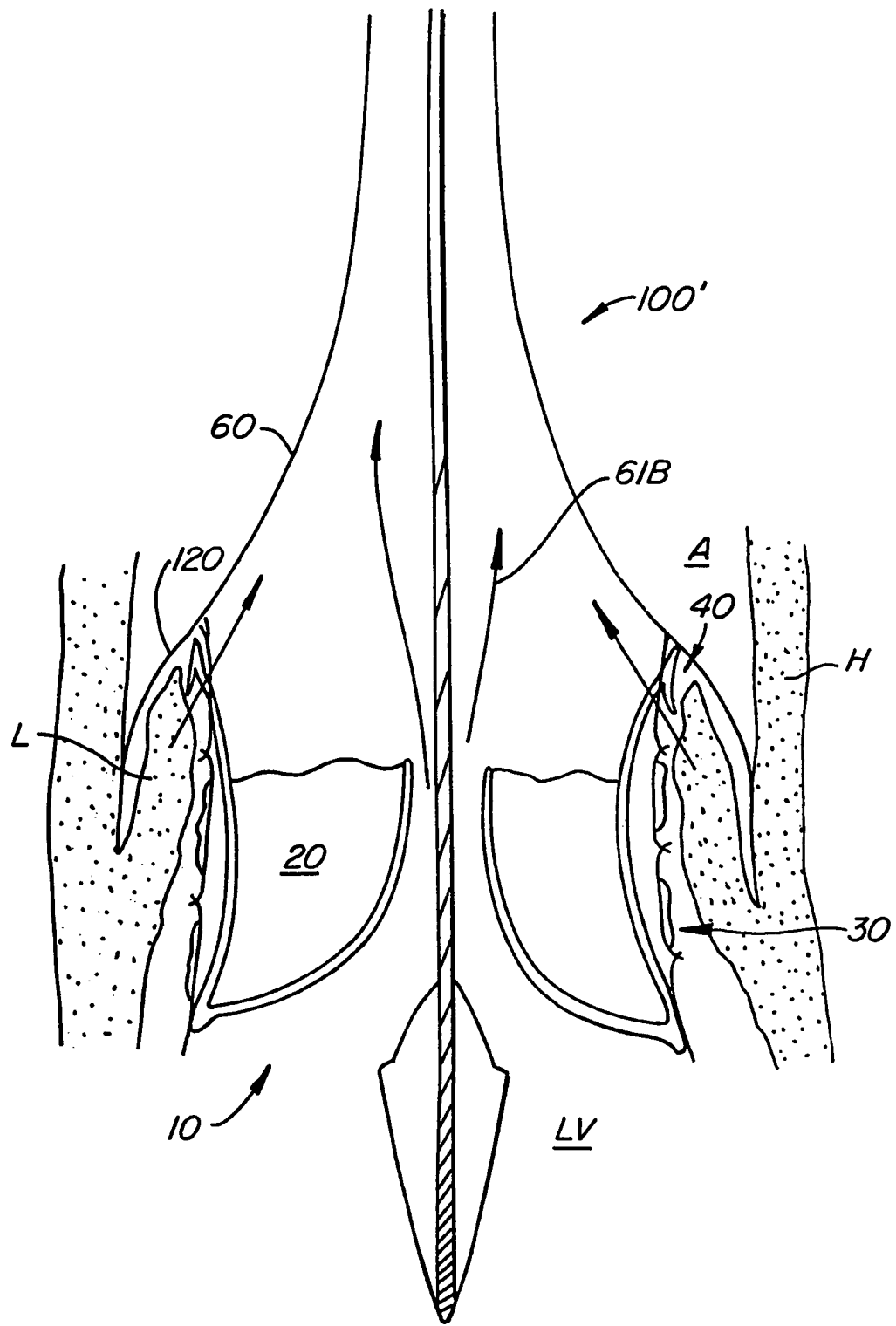
Figure 6F:
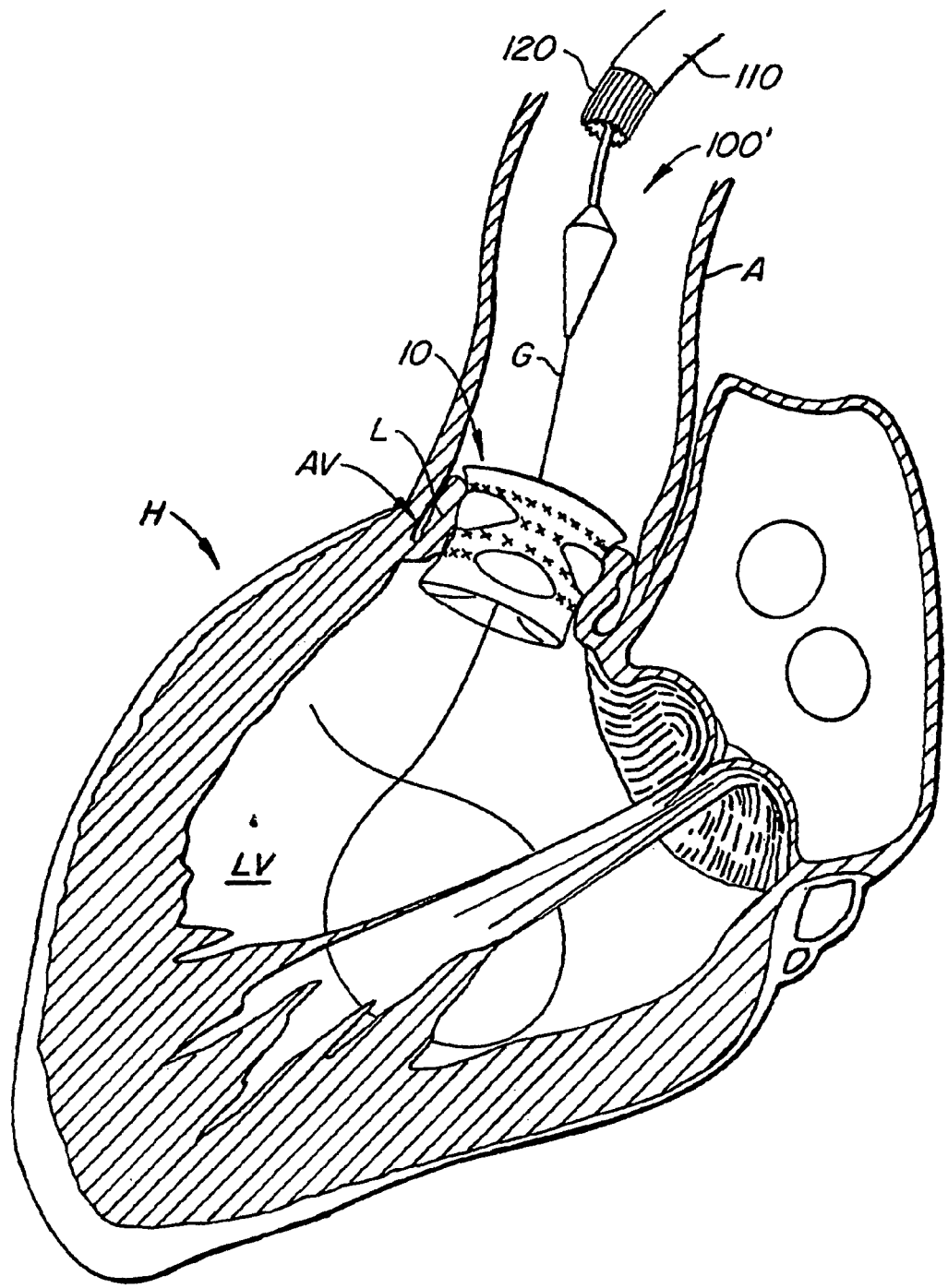

Alternatively, foreshortening may be imposed upon anchor 30 while element 120 is disposed proximal of the leaflets, as in FIG. 6D. Upon positive registration of element 120 against leaflets L, element 120 precludes further distal migration of apparatus 10 during additional foreshortening, thereby reducing a risk of improperly positioning the apparatus. FIG. 6E details engagement of element 120 against the native leaflets. As seen in FIG. 6F, once apparatus 10 is fully deployed, element 120, wires 50 and tubes 60 are decoupled from the apparatus, and delivery system 100' is removed from the patient, thereby completing the procedure.

Figure 7:
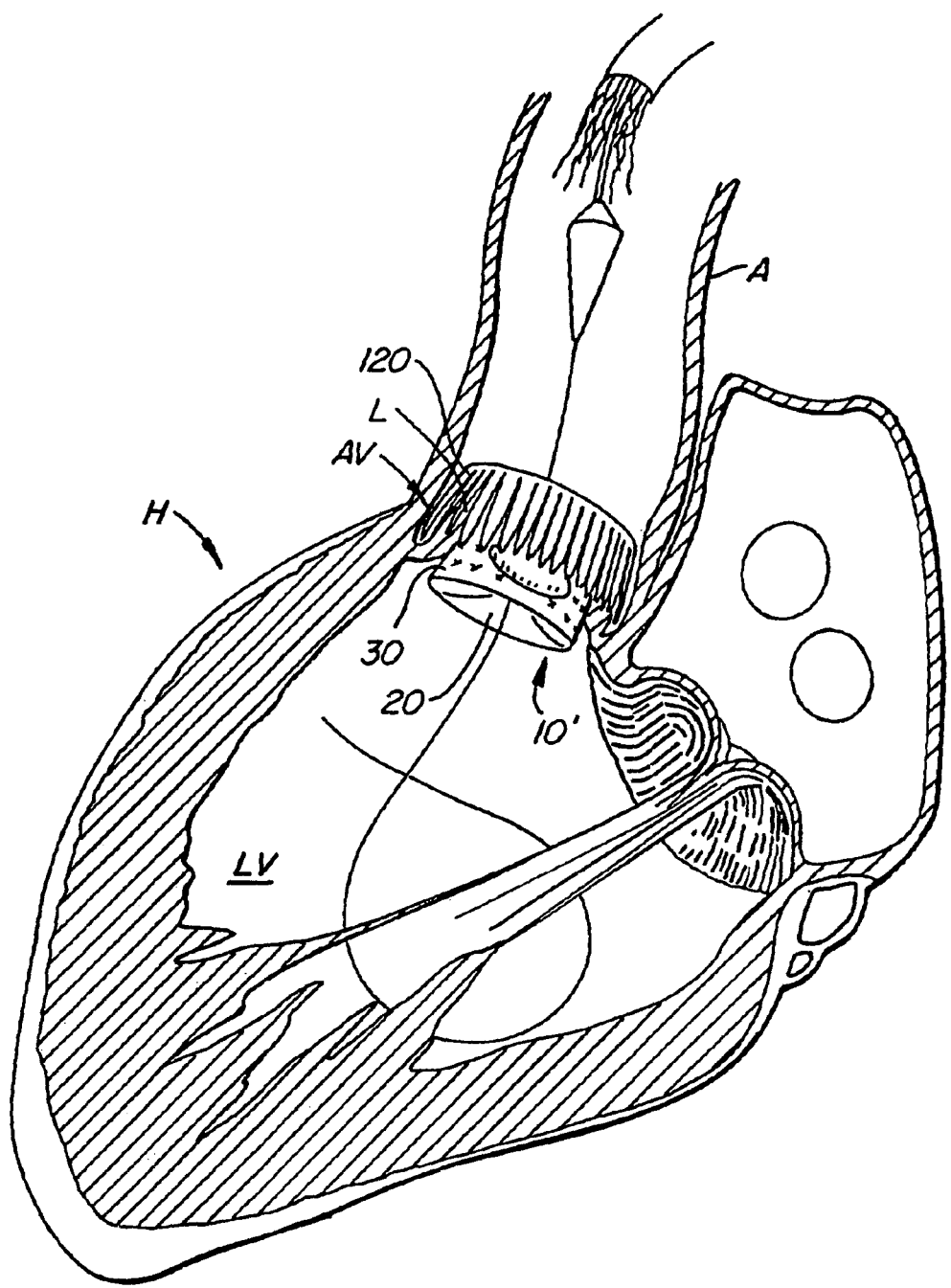
FIG. 7 shows the use of a replacement heart valve and anchor with an alternative positive registration feature to replace an aortic valve.

With reference to FIG. 7, an alternative embodiment of the apparatus of FIG. 6 is described, wherein leaflet engagement element 120 is coupled to anchor 30 of apparatus 10', rather than to delivery system 100. Engagement element 120 remains implanted in the patient post-deployment of apparatus 10'. Leaflets L are sandwiched between lip region 32 of anchor 30 and element 120 in the fully deployed configuration. In this manner, element 120 positively registers apparatus 10' relative to the leaflets and precludes distal migration of the apparatus over time.

Figures 8A, 8B:
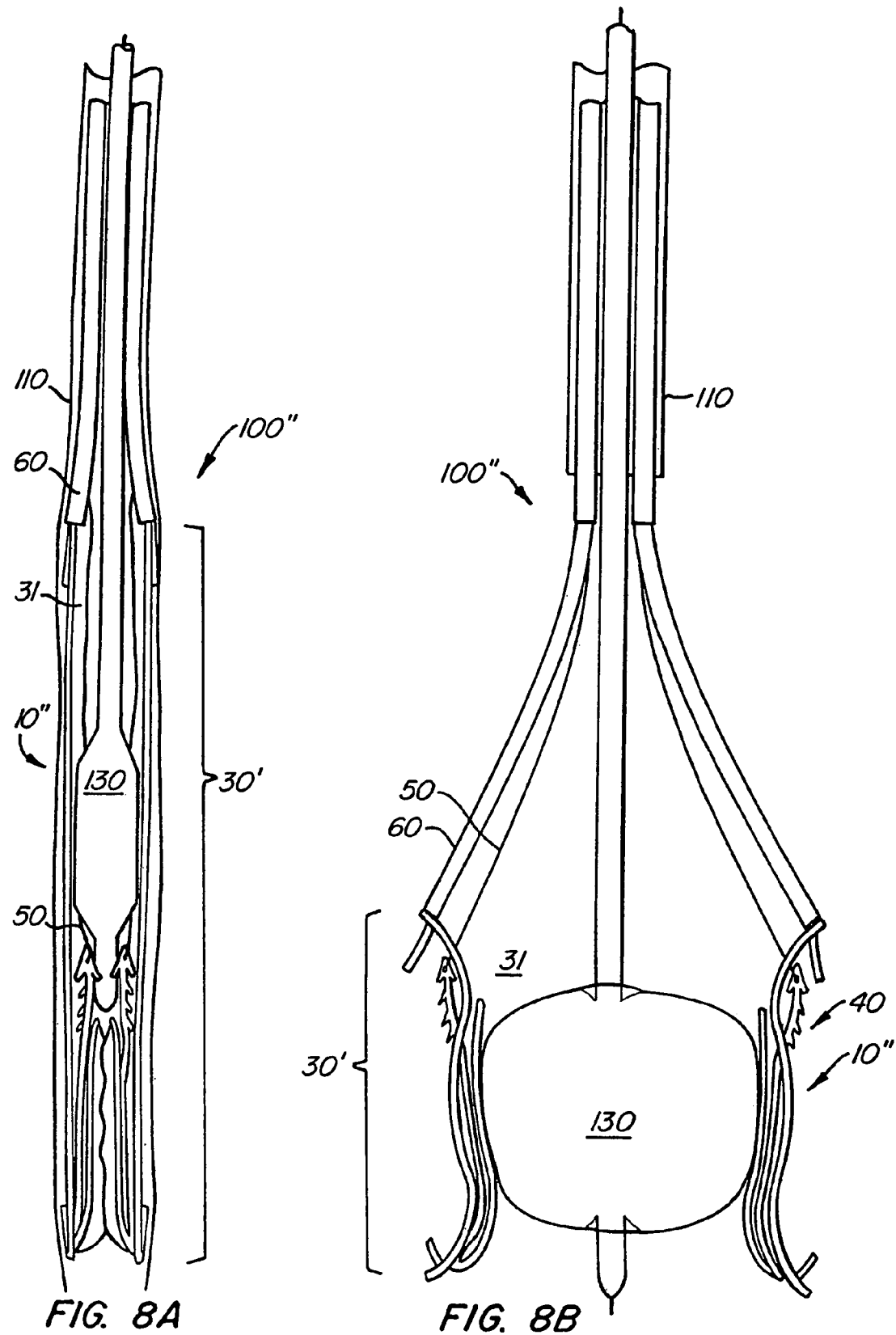
FIGS. 8A-C show another embodiment of a replacement heart valve and anchor according to the invention.
Figure 8C:
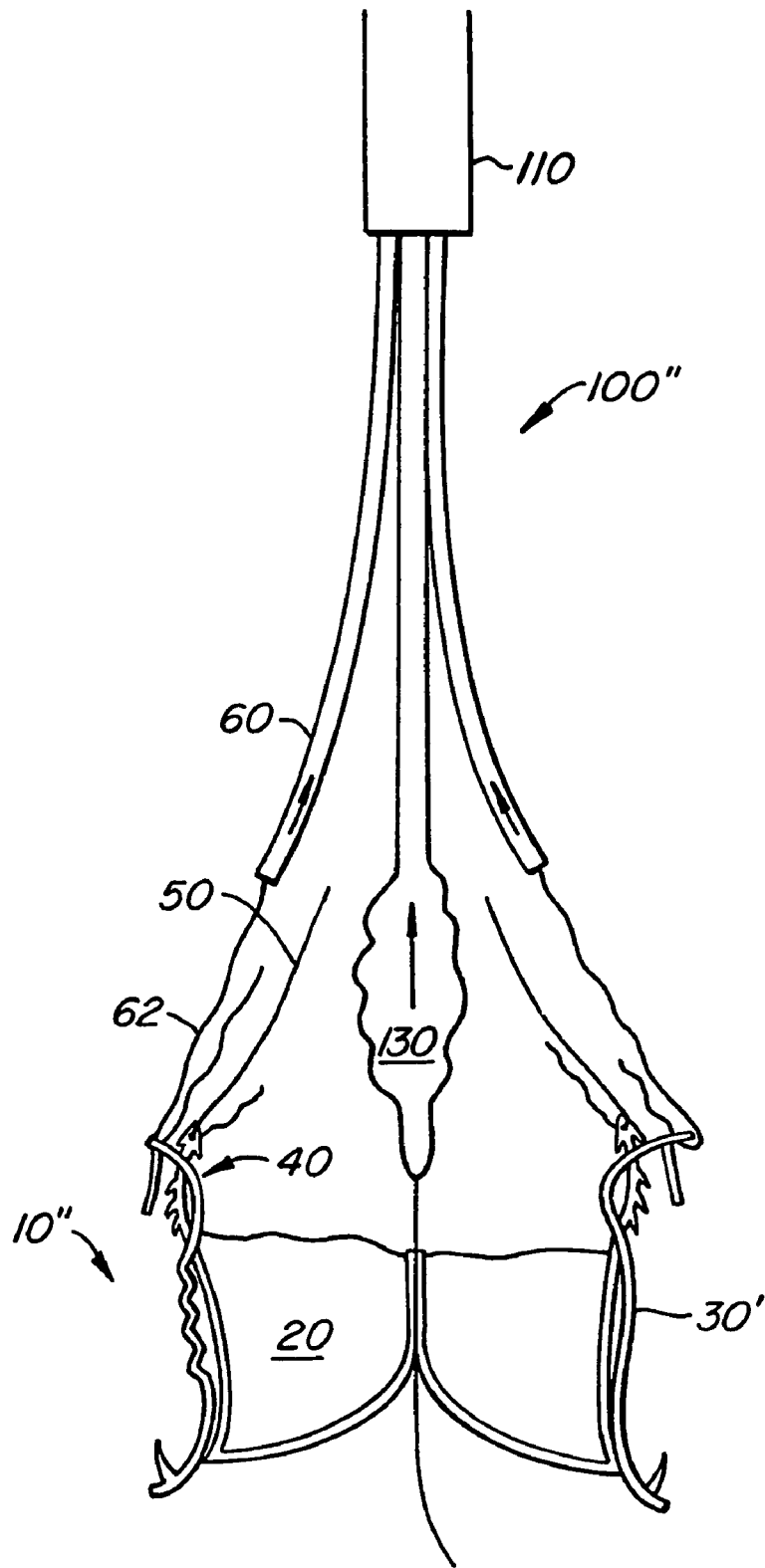

Referring now to FIG. 8, an alternative delivery system adapted for use with a balloon expandable embodiment of the present invention is described. In FIG. 8A, apparatus 10″ comprises anchor 30' that may be fabricated from balloon-expandable materials. Delivery system 100″ comprises inflatable member 130 disposed in a deflated configuration within lumen 31 of anchor 30'. In FIG. 8B, optional outer sheath 110 is retracted, and inflatable member 130 is inflated to expand anchor 30' to the fully deployed configuration. As inflatable member 130 is being deflated, as in earlier embodiments, wires 50 and 62 and tubes 60 may be used to assist deployment of anchor 30' and actuation of locks 40, as well as to provide reversibility and retrievability of apparatus 10″ prior to actuation of locks 40. Next, wires 50 and 62 and tubes 60 are removed from apparatus 10″, and delivery system 100″ is removed, as seen in FIG. 8C.

As an alternative delivery method, anchor 30' may be partially deployed via partial expansion of inflatable member 130. The inflatable member would then be advanced within replacement valve 20 prior to inflation of inflatable member 130 and full deployment of apparatus 10″. Inflation pressures used will range from about 3 to 6 atm, or more preferably from about 4 to 5 atm, though higher and lower atm pressures may also be used (e.g., greater than 3 atm, more preferably greater than 4 atm, more preferably greater than 5 atm, or more preferably greater than 6 atm). Advantageously, separation of inflatable member 130 from replacement valve 20, until partial deployment of apparatus 10″ at a treatment site, is expected to reduce a delivery profile of the apparatus, as compared to previously known apparatus. This profile reduction may facilitate retrograde delivery and deployment of apparatus 10″, even when anchor 30' is balloon-expandable.

Although anchor 30' has illustratively been described as fabricated from balloon-expandable materials, it should be understood that anchor 30' alternatively may be fabricated from self-expanding materials whose expansion optionally may be balloon-assisted. In such a configuration, anchor 30' would expand to a partially deployed configuration upon removal of outer sheath 110. If required, inflatable member 130 then would be advanced within replacement valve 20 prior to inflation. Inflatable member 130 would assist full deployment of apparatus 10″, for example, when the radial force required to overcome resistance from impinging tissue were too great to be overcome simply by manipulation of wires 50 and tubes 60. Advantageously, optional placement of inflatable member 130 within replacement valve 20, only after dynamic self-expansion of apparatus 10″ to the partially deployed configuration at a treatment site, is expected to reduce a delivery profile of the apparatus, as compared to previously known apparatus. This reduction may facilitate retrograde delivery and deployment of apparatus 10″.

Figure 10:
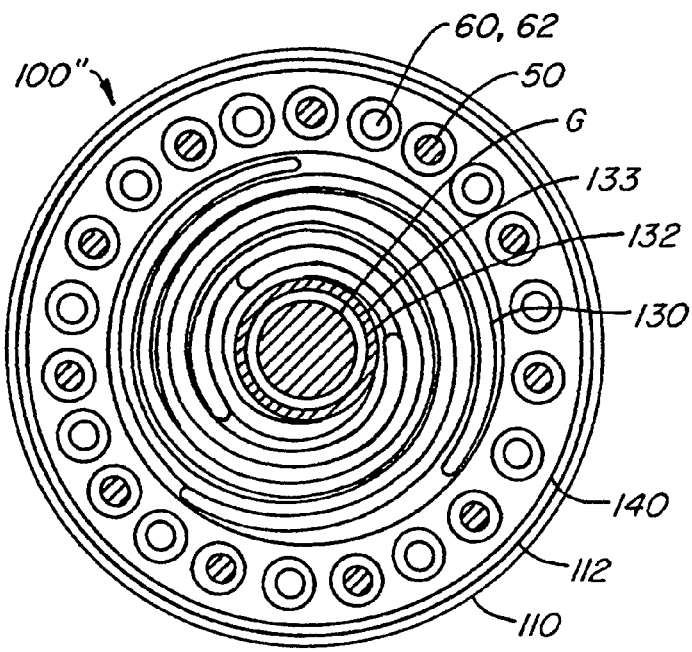
FIG. 10 is a cross-sectional drawing of the delivery system used with the method and apparatus of FIGS. 8 and 9.

With reference to FIGS. 9 and 10, methods and apparatus for a balloon-assisted embodiment of the present invention are described in greater detail. FIGS. 9 and 10 illustratively show apparatus 10' of FIG. 7 used in combination with delivery system 100″ of FIG. 8. FIG. 10 illustrates a sectional view of delivery system 100″. Inner shaft 132 of inflatable member 130 preferably is about 4 Fr in diameter, and comprises lumen 133 configured for passage of guidewire G, having a diameter of about 0.035″, therethrough. Push tubes 60 and pull wires 50 pass through guidetube 140, which preferably has a diameter of about 15 Fr or smaller. Guide tube 140 is disposed within lumen 112 of outer sheath 110, which preferably has a diameter of about 17 Fr or smaller.

Figure 9A:
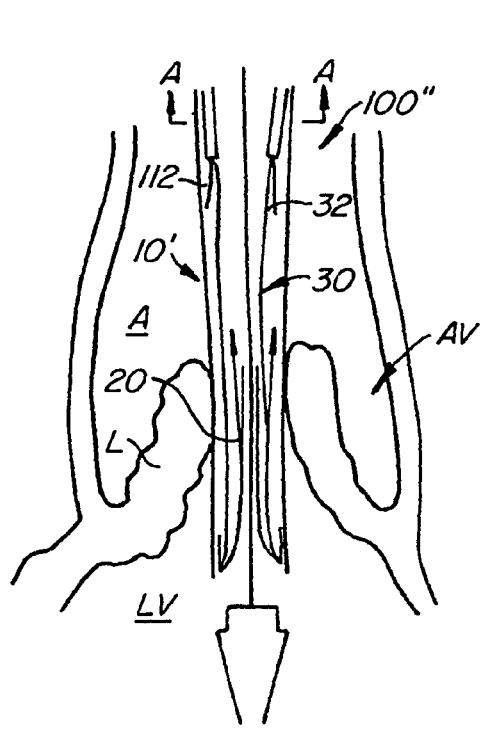
FIGS. 9A-H show delivery and deployment of the replacement heart valve and anchor of FIG. 8.
Figure 9B:
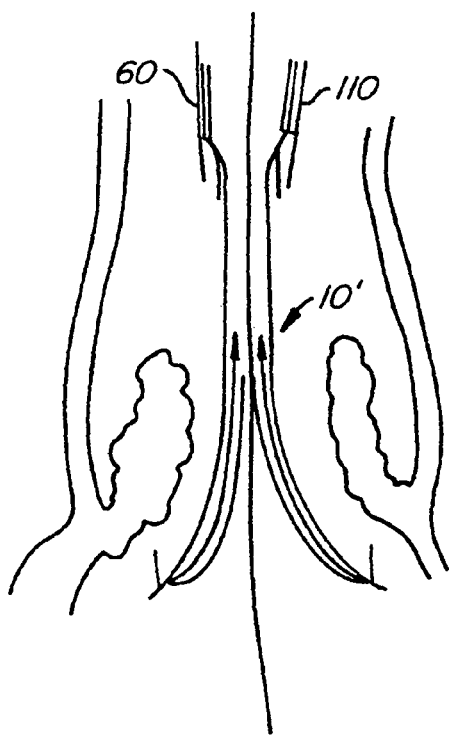

In FIG. 9A, apparatus 10' is delivered to diseased aortic valve AV within lumen 112 of sheath 110. In FIG. 9B, sheath 110 is retracted relative to apparatus 10' to dynamically self-expand the apparatus to the partially deployed configuration. Also retracted and removed is nosecone 102 which is attached to a pre-slit lumen (not shown) that facilitates its removal prior to loading and advancing of a regular angioplasty balloon catheter over guidewire and inside delivery system 110.

Figure 9C:
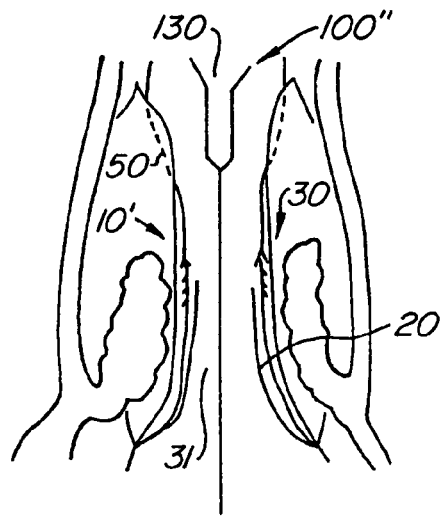

In FIG. 9C, pull wires 50 and push tubes 60 are manipulated from external to the patient to foreshorten anchor 30 and sufficiently expand lumen 31 of the anchor to facilitate advancement of inflatable member 130 within replacement valve 20. Also shown is the tip of an angioplasty catheter 130 being advanced through delivery system 110.

Figure 9D:
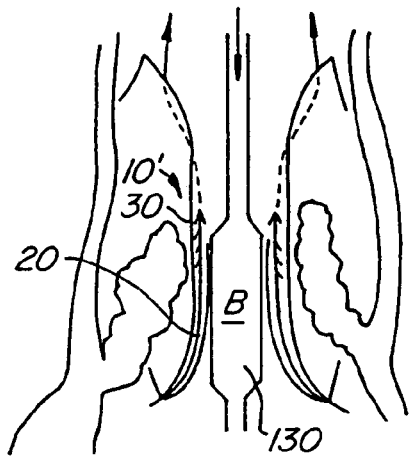
Figure 9E:
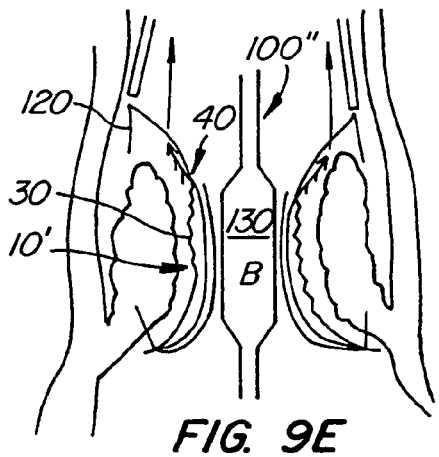
Figure 9F:
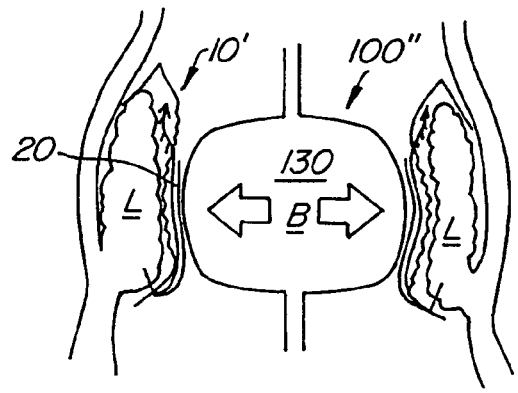
Figure 9G:
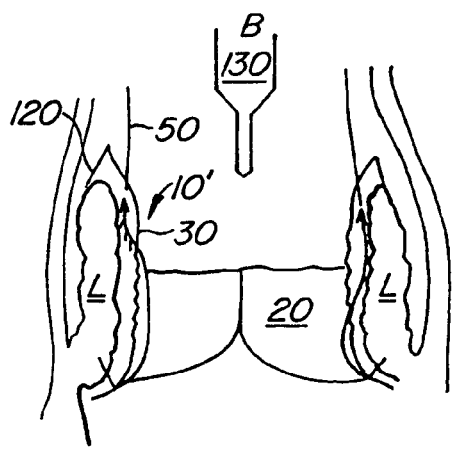
Figure 9H:
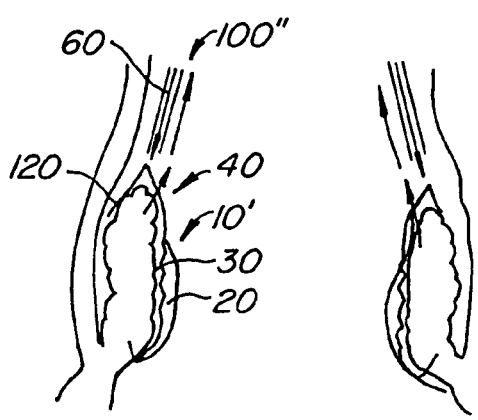

The angioplasty balloon catheter or inflatable member 130 then is advanced within the replacement valve, as in FIG. 9D, and additional foreshortening is imposed upon anchor 30 to actuate locks 40, as in FIG. 9E. The inflatable member is inflated to further displace the patient's native valve leaflets L and ensure adequate blood flow through, and long-term patency of, replacement valve 20, as in FIG. 9F. Inflatable member 130 then is deflated and removed from the patient, as in FIG. 9G. A different size angioplasty balloon catheter could be used to repeat the same step if deemed necessary by the user. Push tubes 60 optionally may be used to further set leaflet engagement element 120, or optional barbs B along posts 38, more deeply within leaflets L, as in FIG. 9H. Then, delivery system 100" is removed from the patient, thereby completing percutaneous heart valve replacement.

As will be apparent to those of skill in the art, the order of imposed foreshortening and balloon expansion described in FIGS. 9 and 10 is only provided for the sake of illustration. The actual order may vary according to the needs of a given patient and/or the preferences of a given medical practitioner. Furthermore, balloon-assist may not be required in all instances, and the inflatable member may act merely as a safety precaution employed selectively in challenging clinical cases.

Figure 11A:
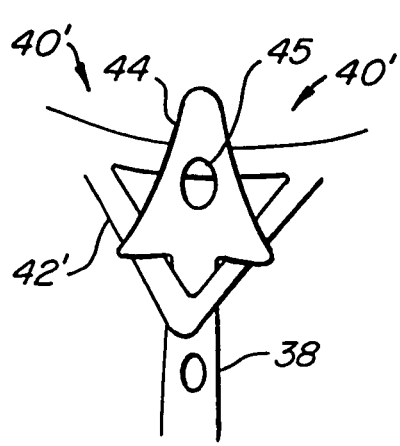
FIGS. 11A-C show alternative locks for use with replacement heart valves and anchors of this invention.
Figure 11B:
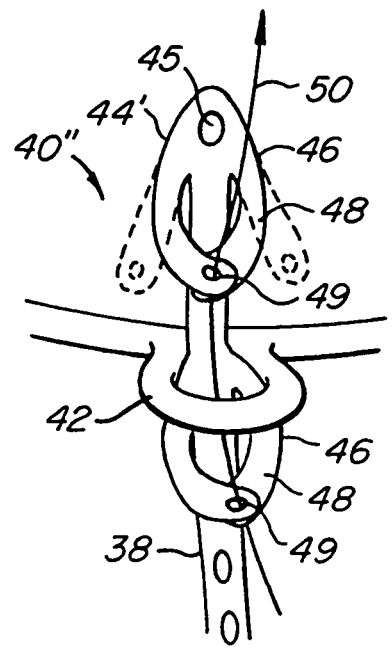

Referring now to FIG. 11, alternative locks for use with apparatus of the present invention are described. In FIG. 11A, lock 40' comprises male interlocking element 44 as described previously. However, female interlocking element 42' illustratively comprises a triangular shape, as compared to the round shape of interlocking element 42 described previously. The triangular shape of female interlocking element 42' may facilitate mating of male interlocking element 44 with the female interlocking element without necessitating deformation of the male interlocking element.

in FIG. 11B, lock 40" comprises alternative male interlocking element 44' having multiple in-line arrowheads 46 along posts 38. Each arrowhead comprises resiliently deformable appendages 48 to facilitate passage through female interlocking element 42. Appendages 48 optionally comprise eyelets 49, such that control wire 50 or a secondary wire may pass therethrough to constrain the appendages in the deformed configuration. To actuate lock 40", one or more arrowheads 46 of male interlocking element 44' are drawn through female interlocking element 42, and the wire is removed from eyelets 49, thereby causing appendages 48 to resiliently expand and actuate lock 40".

Advantageously, providing multiple arrowheads 46 along posts 38 yields a ratchet that facilitates in-vivo determination of a degree of foreshortening imposed upon apparatus of the present invention. Furthermore, optionally constraining appendages 48 of arrowheads 46 via eyelets 49 prevents actuation of lock 40" (and thus deployment of apparatus of the present invention) even after male element 44' has been advanced through female element 42. Only after a medical practitioner has removed the wire constraining appendages 48 is lock 40" fully engaged and deployment no longer reversible.

Figure 11C:
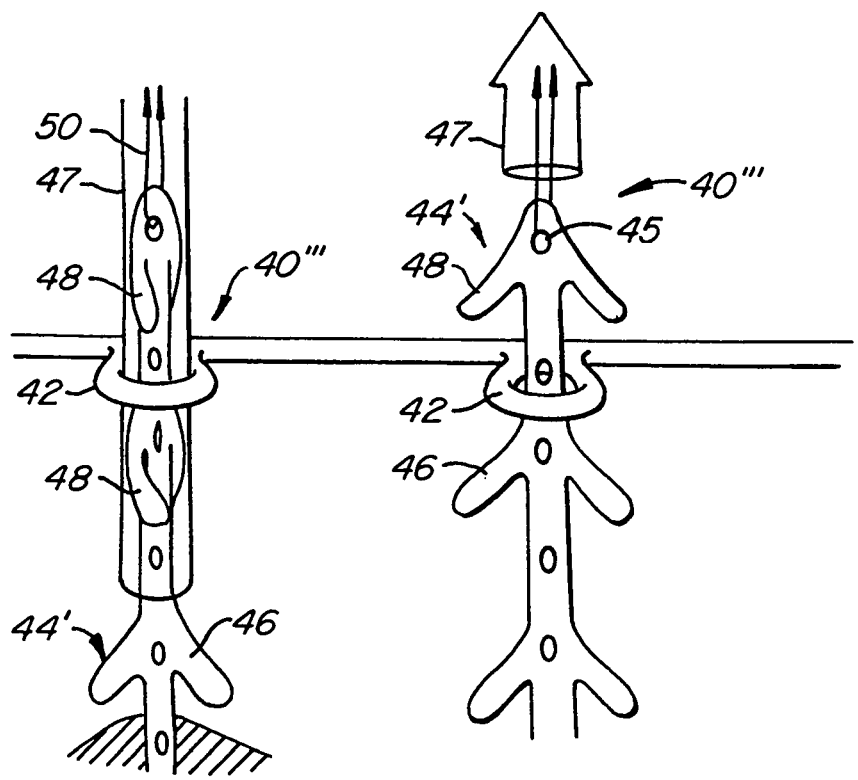

Lock 40'''of FIG. 11C is similar to lock 40" of FIG. 1B, except that optional eyelets 49 on appendages 48 have been replaced by optional overtube 47. Overtube 47 serves a similar function to eyelets 49 by constraining appendages 48 to prevent locking until a medical practitioner has determined that apparatus of the present invention has been foreshortened and positioned adequately at a treatment site. Overtube 47 is then removed, which causes the appendages to resiliently expand, thereby fully actuating lock 40'''.

With reference to FIG. 12, an alternative locking mechanism is described that is configured to engage the patient's aorta. Male interlocking elements 44" of locks 40"" comprise arrowheads 46' having sharpened appendages 48'. Upon expansion from the delivery configuration of FIG. 12A to the foreshortened configuration of FIG. 12B, apparatus 10 positions sharpened appendages 48' adjacent the patient's aorta A. Appendages 48' engage the aortic wall and reduce a risk of device migration over time.

Figure 13:
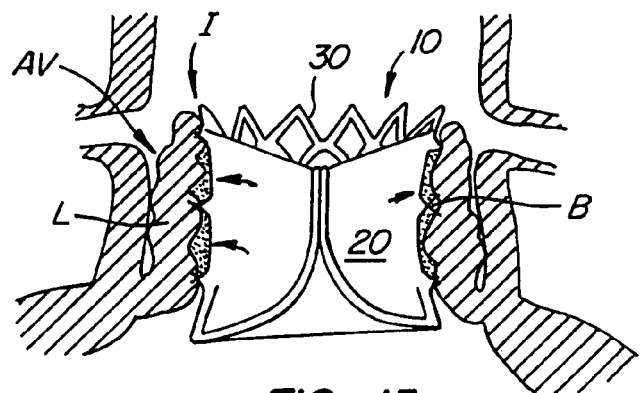
FIG. 13 demonstrates paravalvular leaking around a replacement heart valve and anchor.

With reference now to FIG. 13, a risk of paravalvular leakage or regurgitation around apparatus of the present invention is described. In FIG. 13, apparatus 10 has been implanted at the site of diseased aortic valve AV, for example, using techniques described hereinabove. The surface of native valve leaflets L is irregular, and interface I between leaflets L and anchor 30 may comprise gaps where blood B may seep through. Such leakage poses a risk of blood clot formation or insufficient blood flow.

Figure 14:
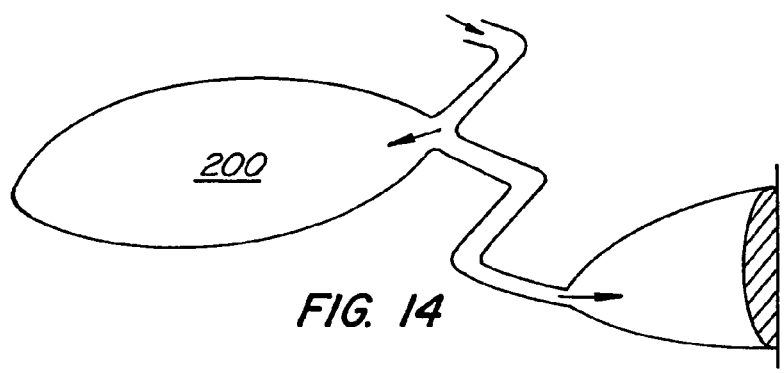
FIG. 14 shows a seal for use with a replacement heart valve and anchor of this invention.

Referring to FIG. 14, optional elements for reducing regurgitation or leakage are described. Compliant sacs 200 may be disposed about the exterior of anchor 30 to provide a more efficient seal along irregular interface I. Sacs 200 may be filled with an appropriate material, for example, water, blood, foam or a hydrogel. Alternative fill materials will be apparent.

Figure 15A:
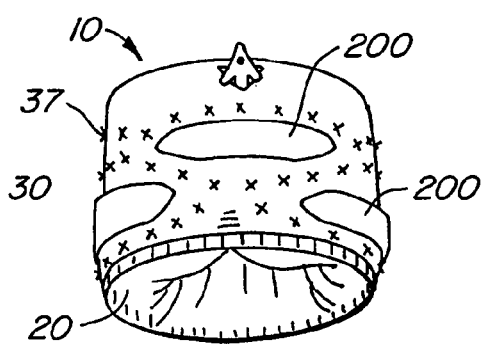
Figure 15B:
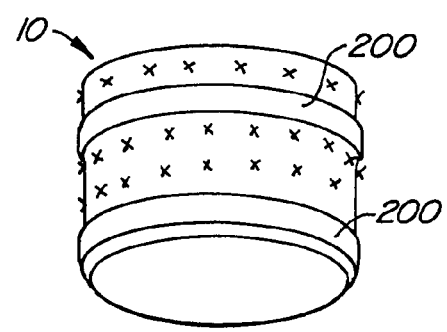
Figure 15C:
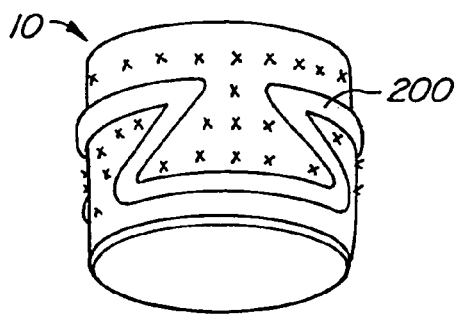
Figure 17A:
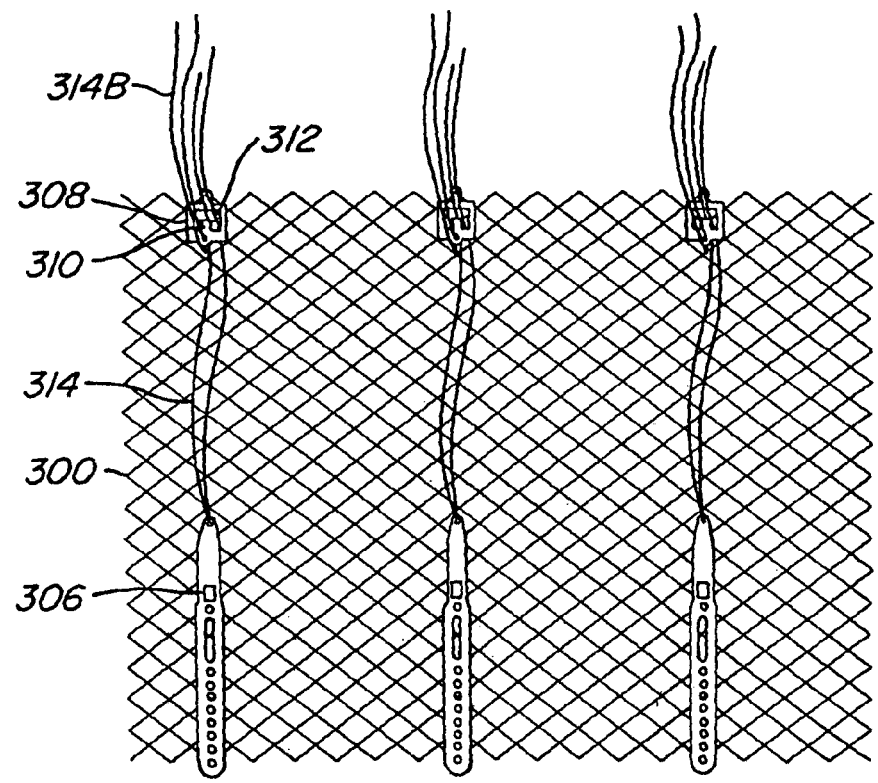
FIGS. 17A-B show an alternative anchor lock embodiment in an unlocked configuration.
Figure 18A:
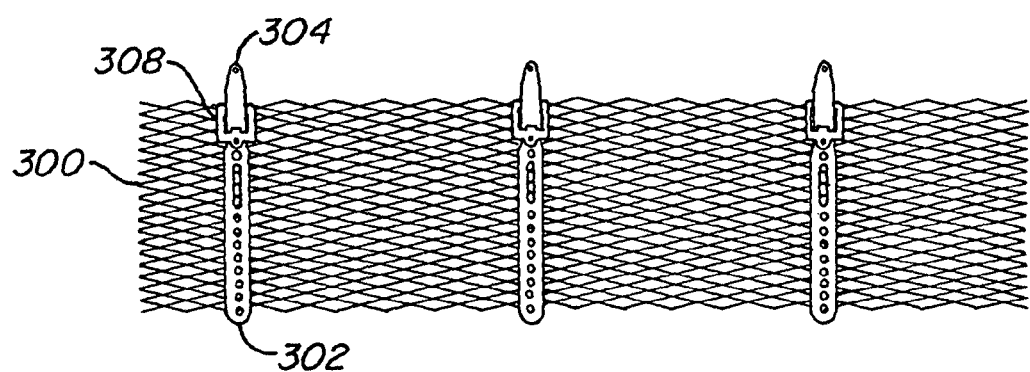
FIGS. 18A-B show the anchor lock of FIGS. 17A-B in a locked configuration.
Figure 17B:
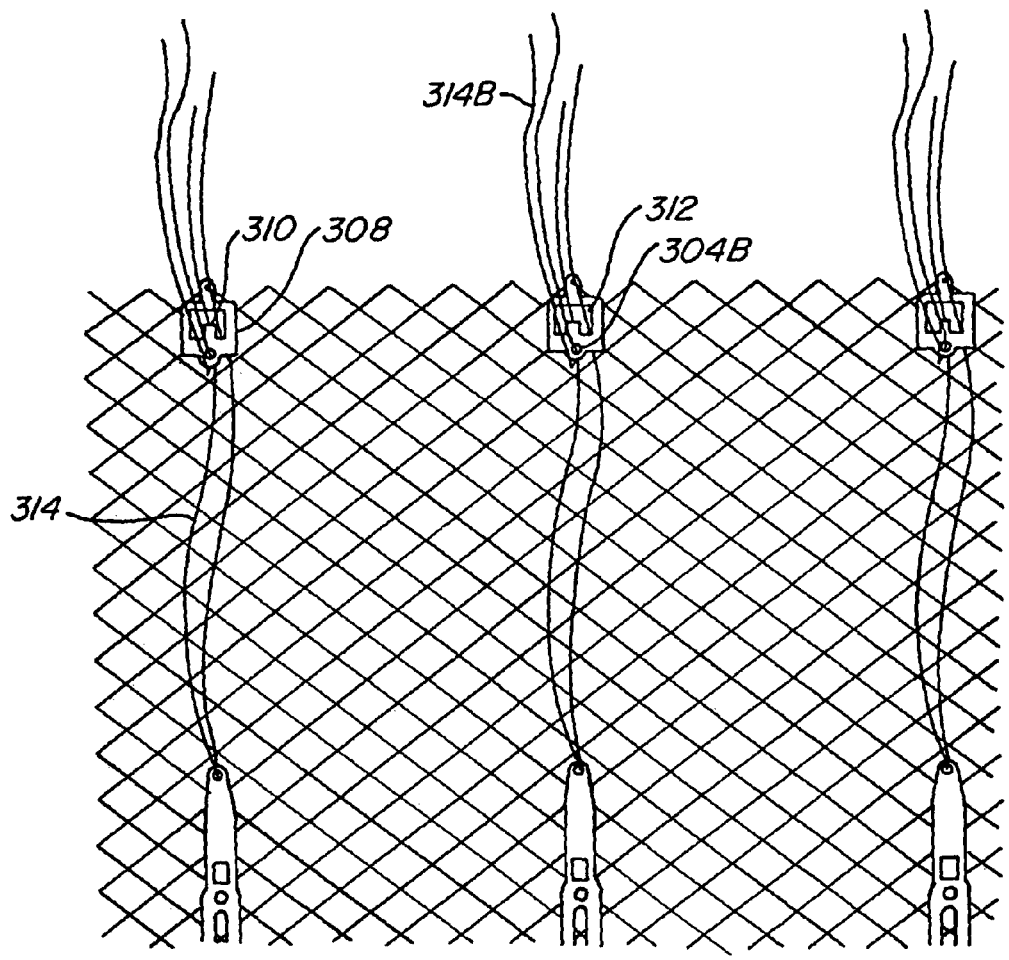
Figure 18B:
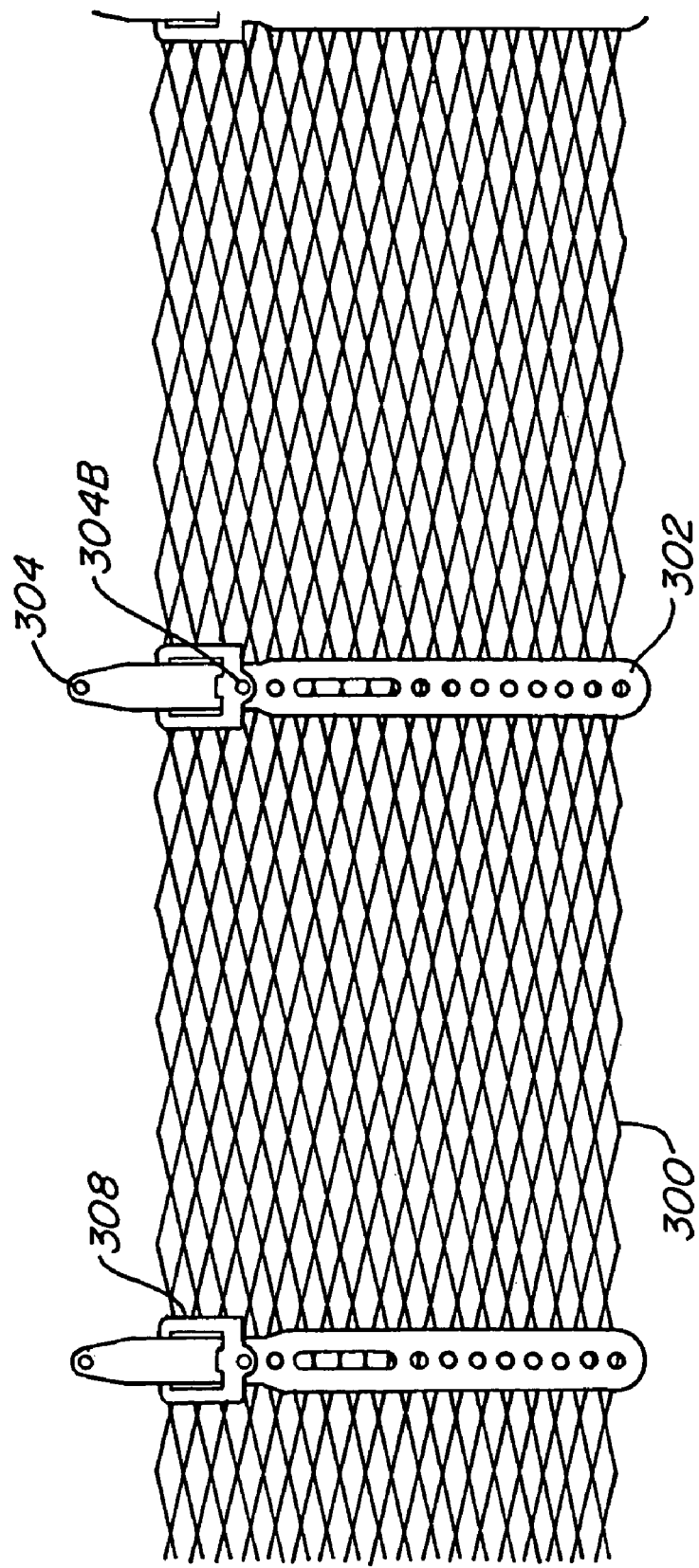

With reference to FIG. 15, illustrative arrangements for sacs 200 are provided. In FIG. 15A, sacs 200 are provided as discrete sacs at different positions along the height of anchor 30. In FIG. 15B, the sacs are provided as continuous cylinders at various heights. In FIG. 15C, a single sac is provided with a cylindrical shape that spans multiple heights. The sacs of FIG. 15D are discrete, smaller and provided in larger quantities. FIG. 15E provides a spiral sac. Alternative sac configurations will be apparent to those of skill in the art.

With reference to FIG. 16, exemplary techniques for fabricating sacs 200 are provided. In FIG. 16A, sacs 20 comprise 'fish-scale' slots 202 that may be back-filled, for example, with ambient blood passing through replacement valve 20. In FIG. 16B, the sacs comprise pores 204 that may be used to fill the sacs. In FIG. 16C, the sacs open to lumen 31 of anchor 30 and are filled by blood washing past the sacs as the blood moves through apparatus 10.

FIGS. 17A-B and 18A-B show yet another alternative embodiment of the anchor lock. Anchor 300 has a plurality of male interlocking elements 302 having eyelets 304 formed therein. Male interlocking elements are connected to braided structure 300 by inter-weaving elements 302 (and 308) or alternatively suturing, soldering, welding, or connecting with adhesive. Valve commissures 24 are connected to male interlocking elements 302 along their length. Replacement valve 20 annular base 22 is connected to the distal end 34 of anchor 300 (or 30) as is illustrated in figures 1A and 1B. Male interlocking elements 302 also include holes 306 that mate with tabs 310 extending into holes 312 in female interlocking elements 308. To lock, control wires 314 passing through eyelets 304 and holes 312 are pulled proximally with respect to the proximal end of braided anchor 300 to draw the male interlocking elements through holes 312 so that tabs 310 engage holes 306 in male interlocking elements 302. Also shown is release wires 314B that passes through eyelet 304B in female interlocking element 308. If needed, during the procedure, the user may pull on release wires 314B reversing orientation of tabs 310 releasing the anchor and allowing for repositioning of the device or it's removal from the patient. Only when final positioning as desired by the operating physician, would release wire 314B and control wire 314 are cut and removed from the patient with the delivery system.

Figure 19:
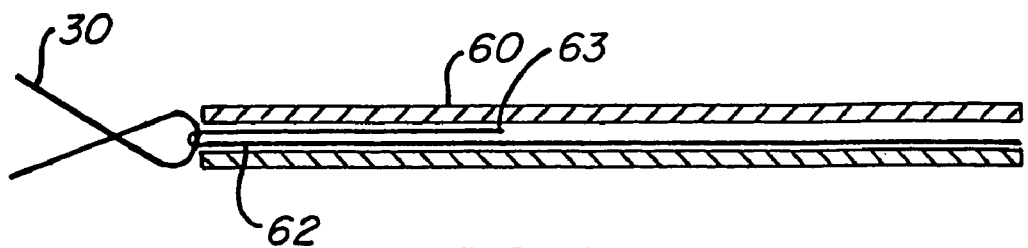
FIG. 19 shows an alternative anchor deployment tool attachment and release mechanism for use with the invention.
Figure 20:
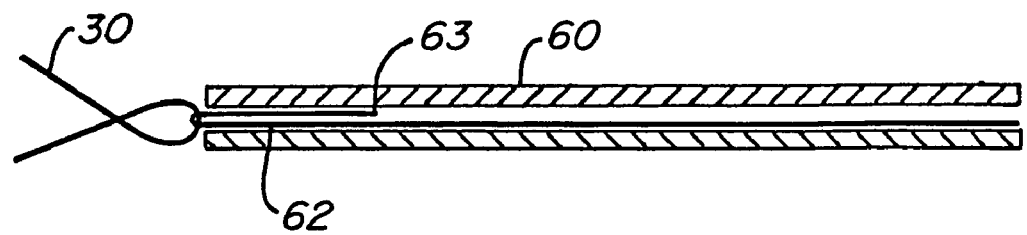
FIG. 20 shows the attachment and release mechanism of FIG. 19 in the process of being released.
Figure 21:
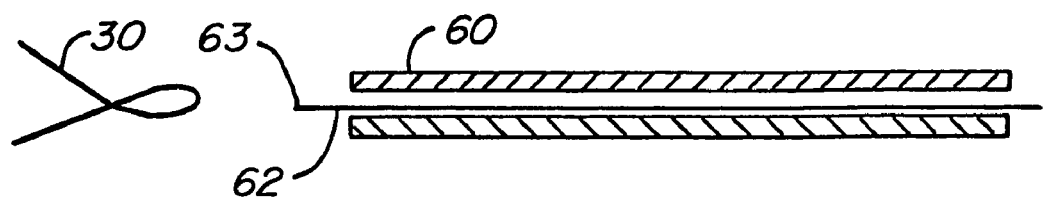
FIG. 21 shows the attachment and release mechanism of FIGS. 19 and 20 in a released condition.

FIGS. 19-21 show an alternative way of releasing the connection between the anchor and its actuating tubes and control wires. Control wires 62 extend through tubes 60 from outside the patient, loop through the proximal region of anchor 30 and extend partially back into tube 60. The doubled up portion of control wire 62 creates a force fit within tube 60 that maintains the control wire's position with respect to tube 60 when all control wires 62 are pulled proximally to place a proximally directed force on anchor 30. When a single control wire 62 is pulled proximally, however, the frictional fit between that control wire and the tube in which it is disposed is overcome, enabling the end 63 of control wire 62 to pull free of the tube, as shown in FIG. 21, thereby releasing anchor 30.

Figure 22:
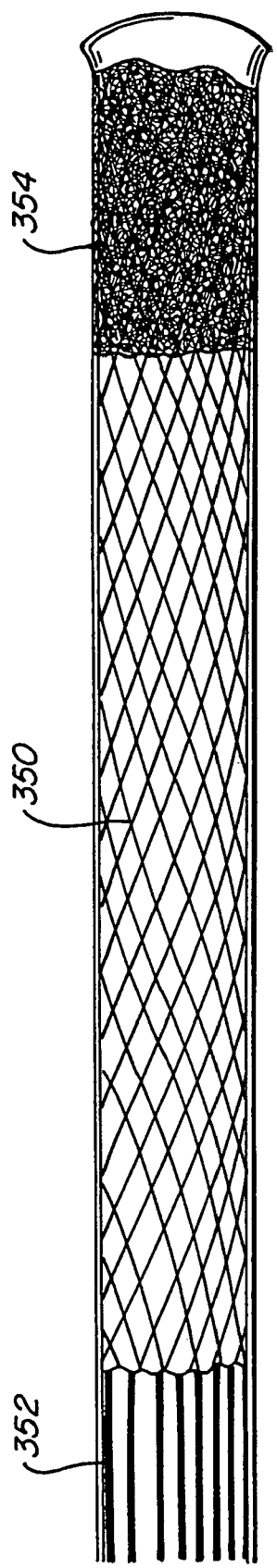
FIG. 22 shows an alternative embodiment of a replacement heart valve and anchor and a deployment tool according to the invention in an undeployed configuration.
Figure 23:
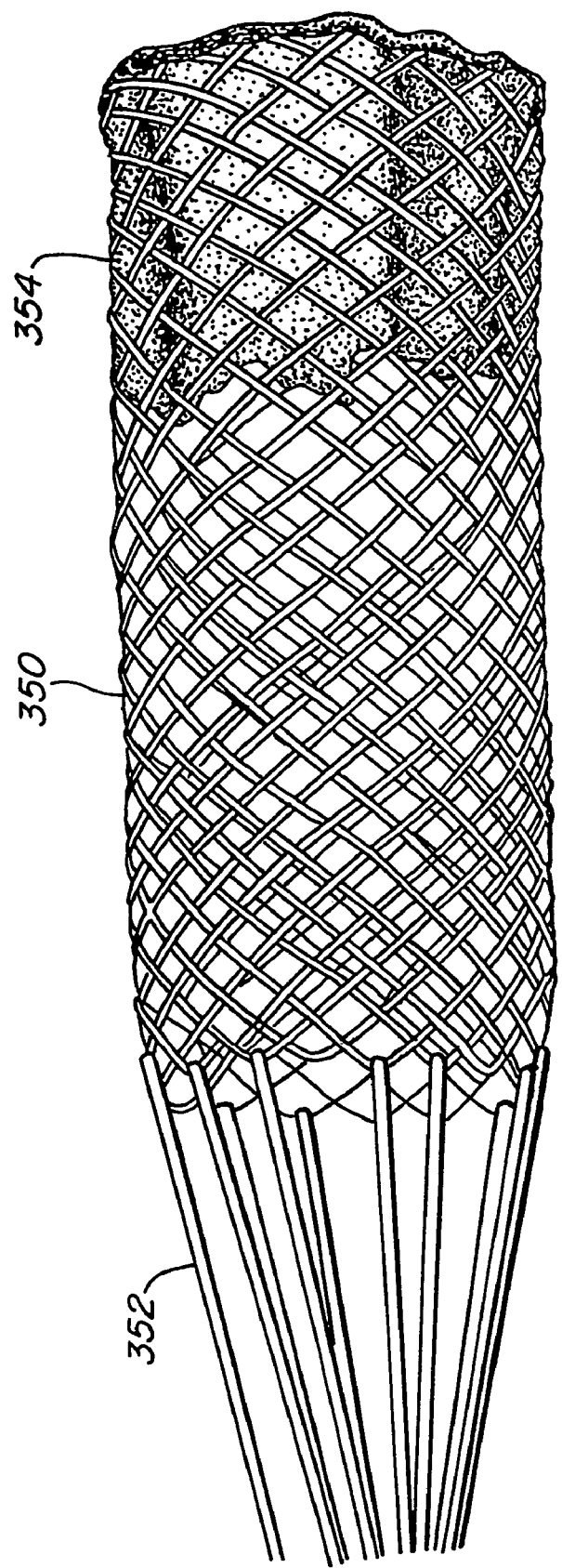
FIG. 23 shows the replacement heart valve and anchor of FIG. 22 in a partially deployed configuration.
Figure 24:
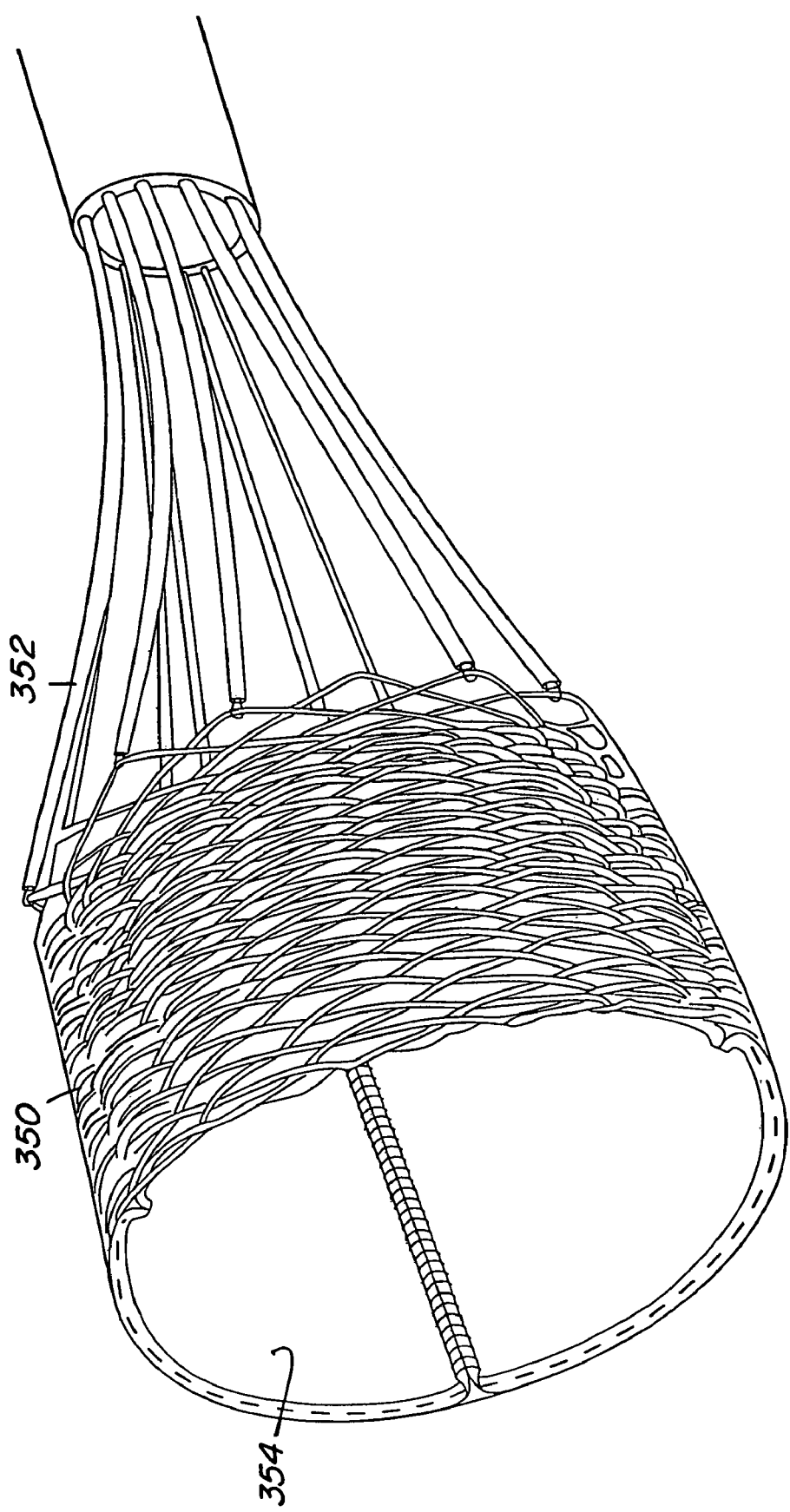
FIG. 24 shows the replacement heart valve and anchor of FIGS. 22 and 23 in a more fully deployed configuration but with the deployment tool still attached.

FIGS. 22-24 show an alternative embodiment of the anchor. Anchor 350 is made of a metal braid, such as Nitinol or stainless steel. A replacement valve 354 is disposed within anchor 350. Anchor 350 is actuated in substantially the same way as anchor 30 of FIGS. 1-4 through the application of proximally and distally directed forces from control wires (not shown) and tubes 352.

Figure 25:
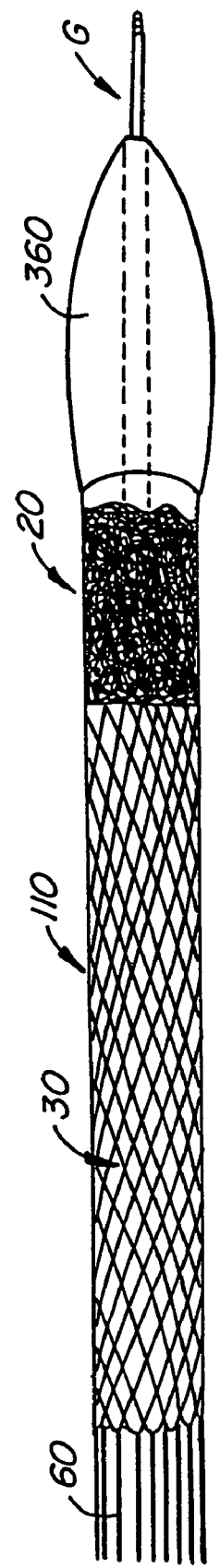
FIG. 25 shows yet another embodiment of the delivery and deployment apparatus of the invention in use with a replacement heart valve and anchor.
Figure 26:
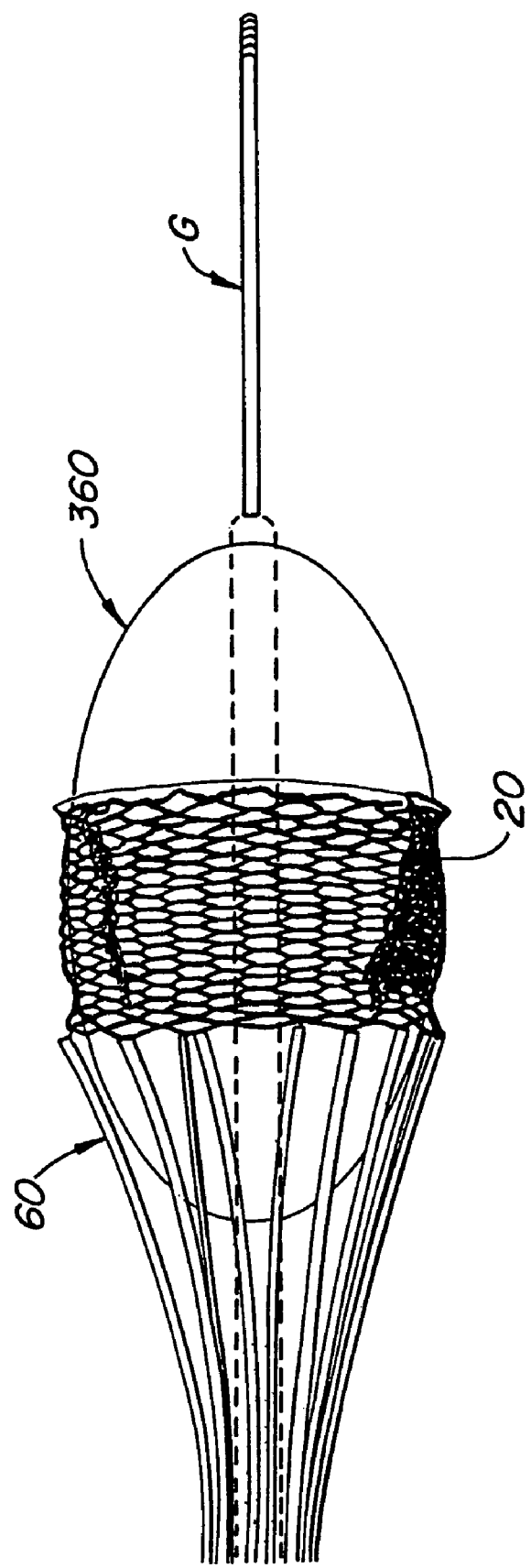
FIG. 26 shows the delivery and deployment apparatus of FIG. 25 in the process of deploying a replacement heart valve and anchor.
Figure 27:
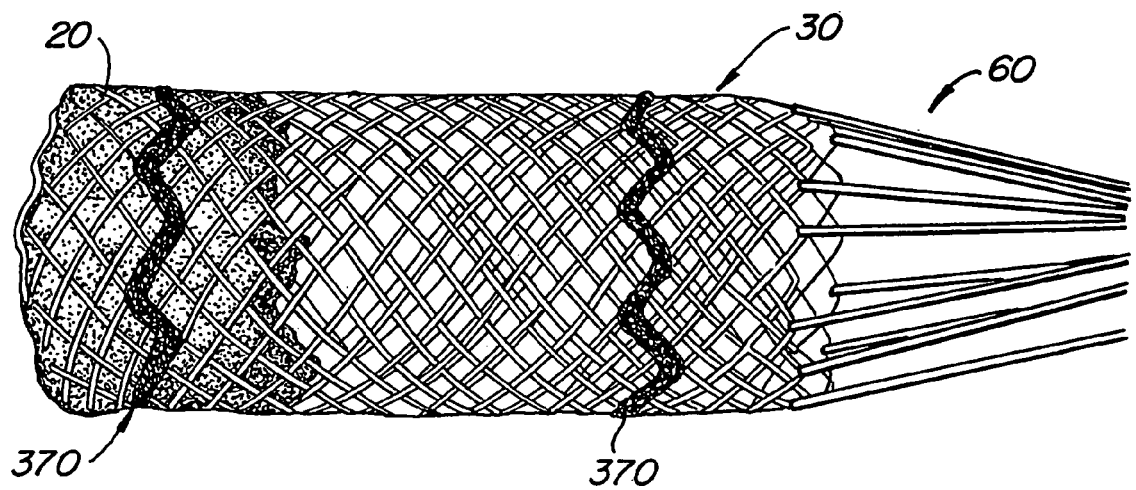
FIG. 27 show an embodiment of the invention employing seals at the interface of the replacement heart valve and anchor and the patient's tissue.
Figure 28:
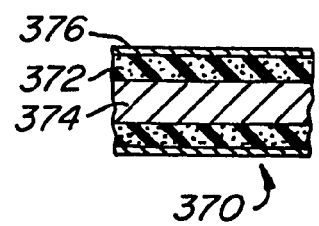
FIG. 28 is a longitudinal cross-sectional view of the seal shown in FIG. 27 in compressed form.
Figure 29:
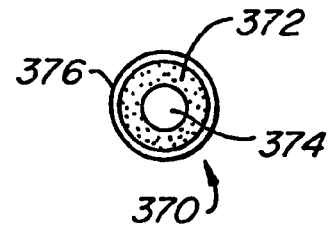
FIG. 29 is a transverse cross-sectional view of the seal shown in FIG. 28.

FIGS. 25 and 26 show yet another embodiment of the delivery and deployment apparatus of the invention. As an alternative to the balloon expansion method described with respect to FIG. 8, in this embodiment the nosecone (e.g., element 102 of FIG. 5) is replaced by an angioplasty balloon catheter 360. Thus, angioplasty balloon catheter 360 precedes sheath 110 on guidewire G. When anchor 30 and valve 20 are expanded through the operation of tubes 60 and the control wires (not shown) as described above, balloon catheter 360 is retracted proximally within the expanded anchor and valve and expanded further as described above with respect to FIG. 8.

Figure 30:
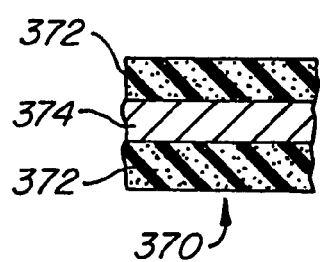
FIG. 30 is a longitudinal cross-sectional view of the seal shown in FIG. 27 in expanded form.
Figure 31:
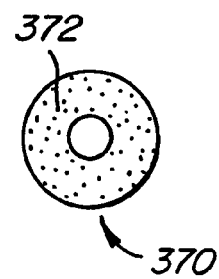
FIG. 31 is a transverse cross-sectional view of the seal shown in FIG. 30.

FIGS. 27-31 show seals 370 that expand over time to seal the interface between the anchor and valve and the patient's tissue. Seals 370 are preferably formed from Nitinol wire surrounded by an expandable foam. As shown in cross-section in FIGS. 28 and 29, at the time of deployment, the foam 372 is compressed about the wire 374 and held in the compressed form by a time-released coating 376. After deployment, coating 376 dissolves in vivo to allow foam 372 to expand, as shown in FIGS. 30 and 31.

Figure 32:
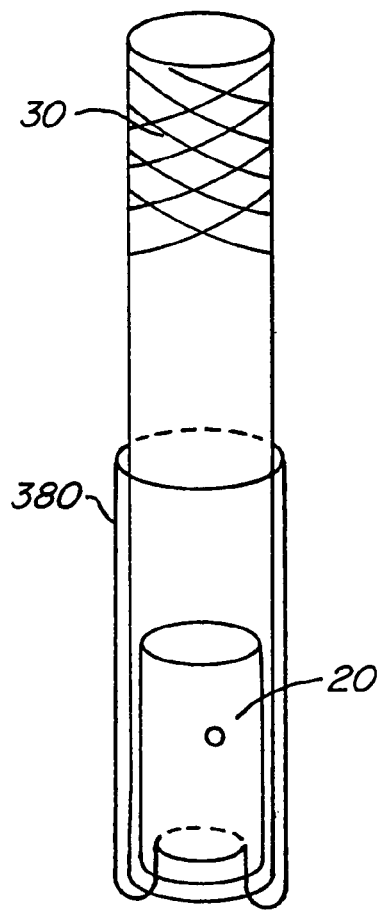
FIG. 32 shows yet another embodiment of the replacement heart valve and anchor of this invention in an undeployed configuration.
Figure 33:
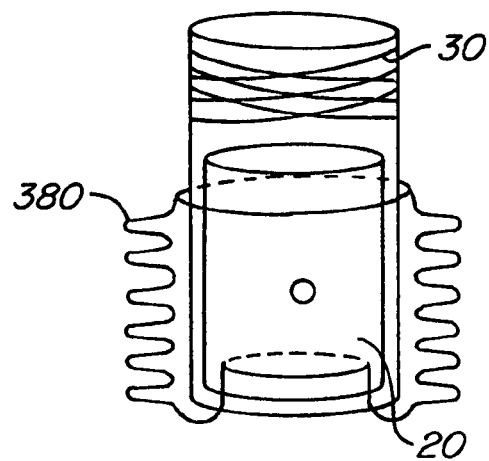
FIG. 33 shows the replacement heart valve and anchor of FIG. 32 in a deployed configuration.
Figure 34:
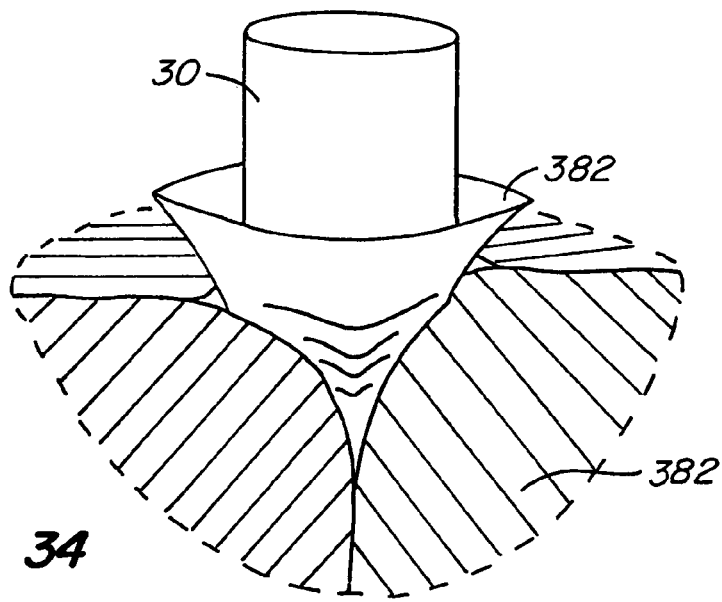
FIG. 34 shows the replacement heart valve and anchor of FIGS. 32 and 33 deployed in a patient's heart valve.

FIGS. 32-34 show another way to seal the replacement valve against leakage. A fabric seal 380 extends from the distal end of valve 20 and back proximally over anchor 30 during delivery. When deployed, as shown in FIGS. 33 and 34, fabric seal 380 bunches up to create fabric flaps and pockets that extend into spaces formed by the native valve leaflets 382, particularly when the pockets are filled with blood in response to backflow blood pressure. This arrangement creates a seal around the replacement valve.

FIGS. 35A-H show another embodiment of a replacement heart valve apparatus in accordance with the present invention. Apparatus 450 comprises replacement valve 460 (see FIGS. 37B and 38C) disposed within and coupled to anchor 470. Replacement valve 460 is preferably biologic, e.g. porcine, but alternatively may be synthetic. Anchor 470 preferably is fabricated from self-expanding materials, such as a stainless steel wire mesh or a nickel-titanium alloy ("Nitinol"), and comprises lip region 472, skirt region 474, and body regions 476a, 476b and 476c. Replacement valve 460 preferably is coupled to skirt region 474, but alternatively may be coupled to other regions of the anchor. As described hereinbelow, lip region 472 and skirt region 474 are configured to expand and engage/capture a patient's native valve leaflets, thereby providing positive registration, reducing paravalvular regurgitation, reducing device migration, etc.

Figures 35A, 35B:
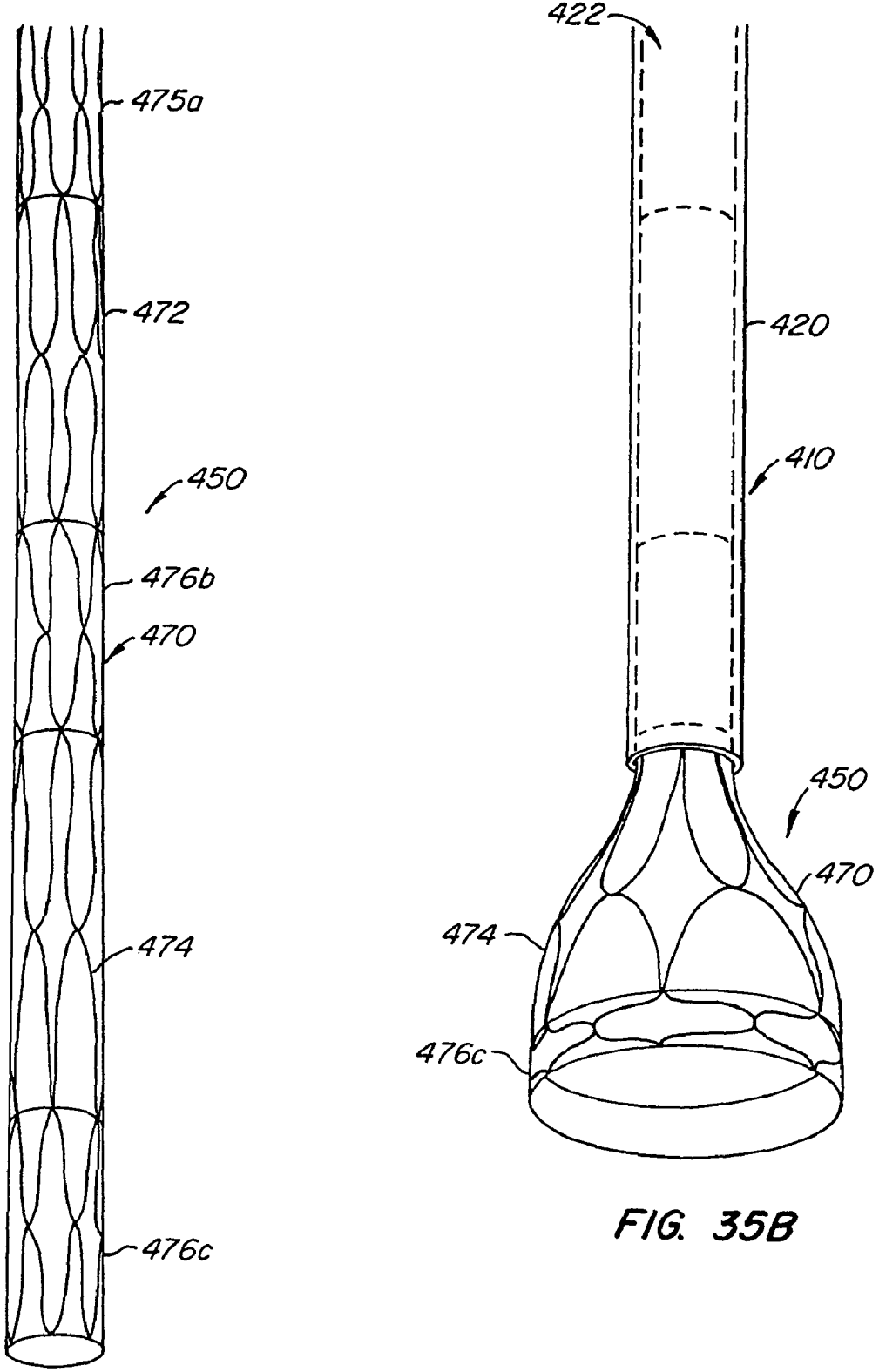
FIGS. 35A-H show yet another embodiment of a replacement heart valve, anchor and deployment system according to this invention.

As seen in FIG. 35A, apparatus 450 is collapsible to a delivery configuration, wherein the apparatus may be delivered via delivery system 410. Delivery system 410 comprises sheath 420 having lumen 422, as well as wires 424a and 424b seen in FIGS. 35D-35G. Wires 424a are configured to expand skirt region 474 of anchor 470, as well as replacement valve 460 coupled thereto, while wires 424b are configured to expand lip region 472.

Figures 35C, 35D:
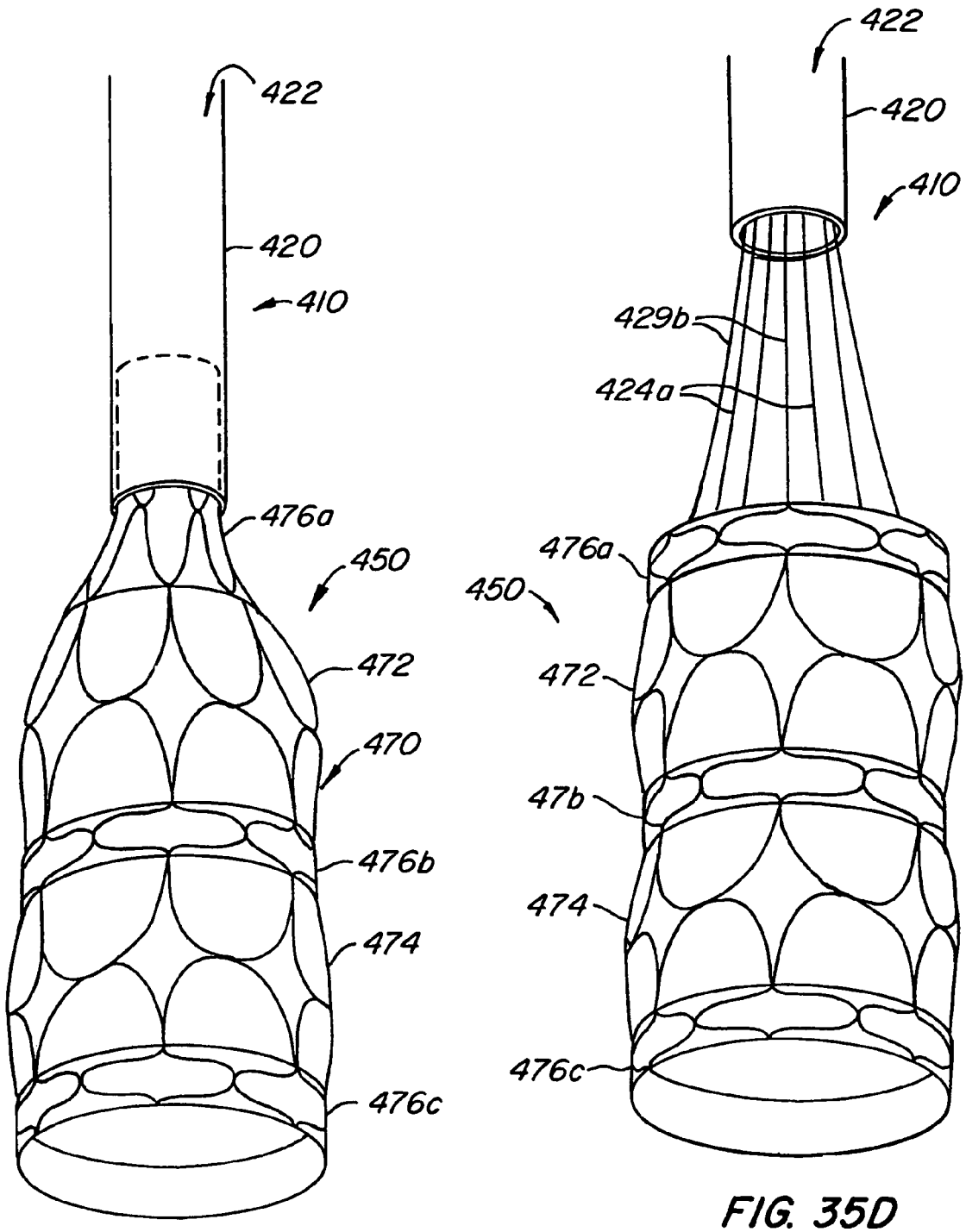
Figure 35E:
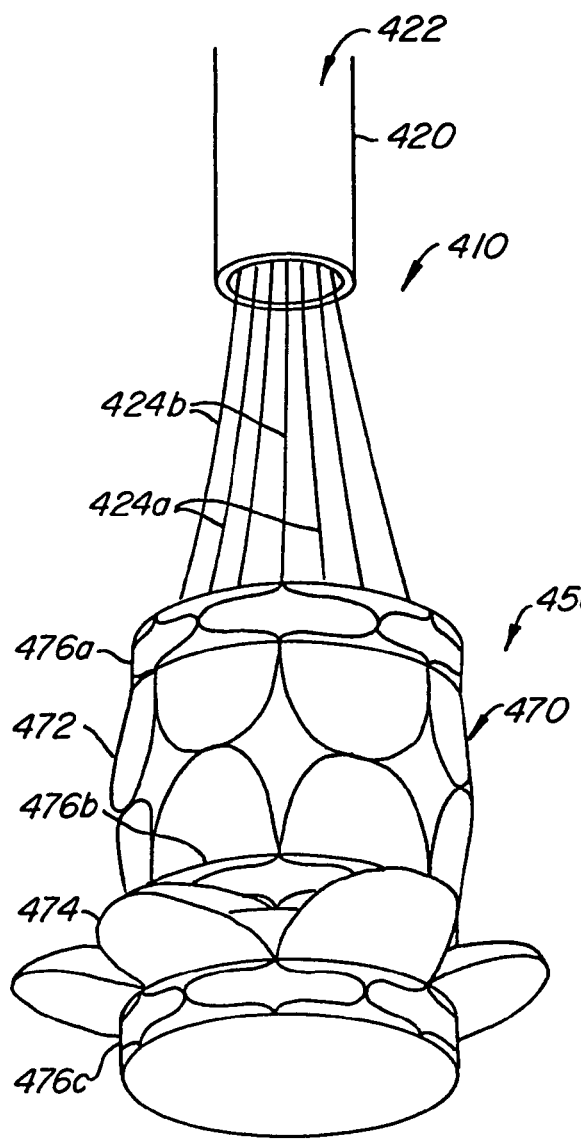
Figure 35F:
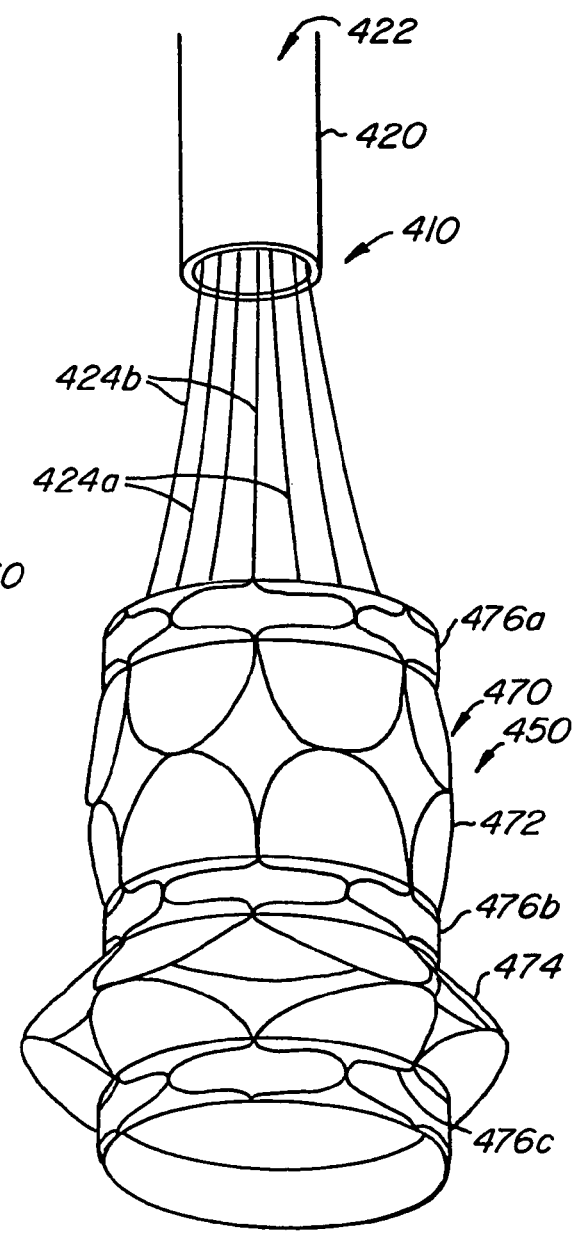

As seen in FIG. 35B, apparatus 450 may be delivered and deployed from lumen 422 of catheter 420 while the apparatus is disposed in the collapsed delivery configuration. As seen in FIGS. 35B-35D, catheter 420 is retracted relative to apparatus 450, which causes anchor 470 to dynamically self-expand to a partially deployed configuration. Wires 424a are then retracted to expand skirt region 474, as seen in FIGS. 35E and 35F. Preferably, such expansion may be maintained via locking features described hereinafter.

Figure 35G:
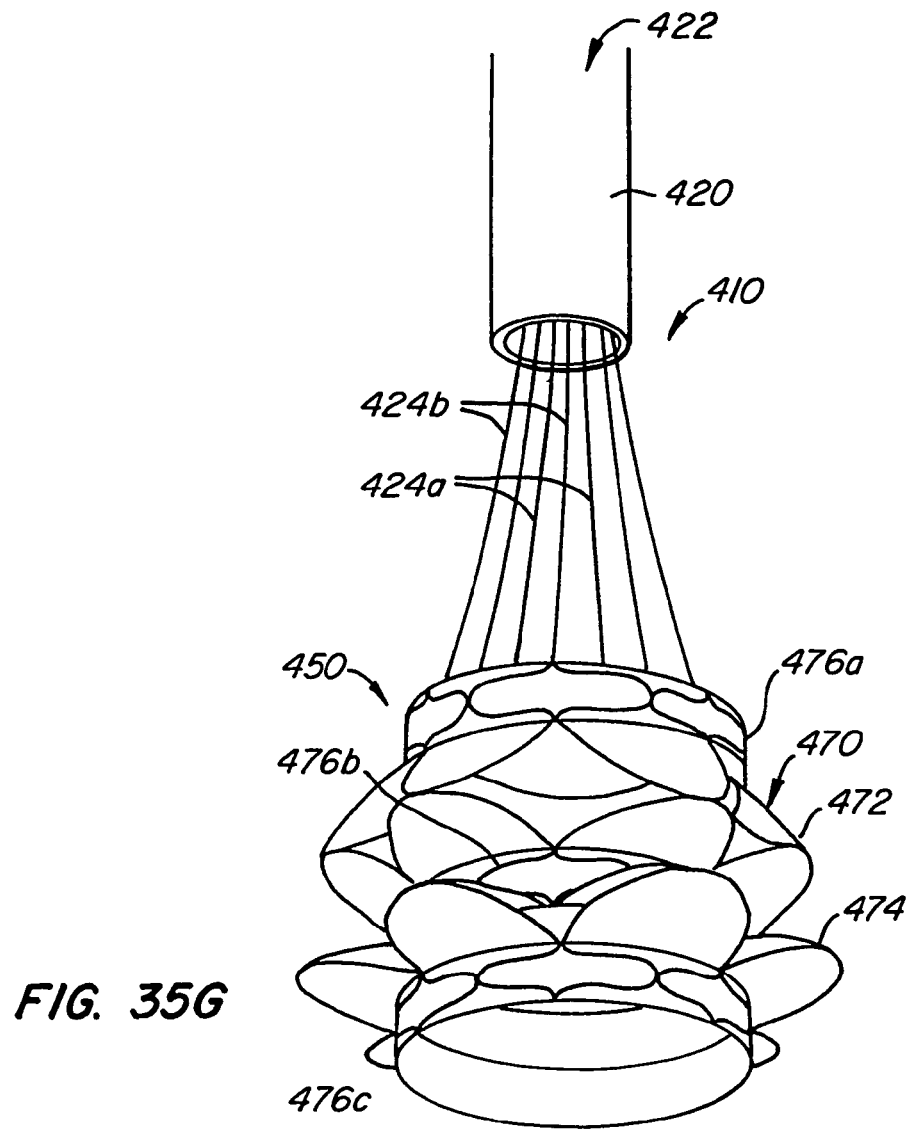
Figure 35H:
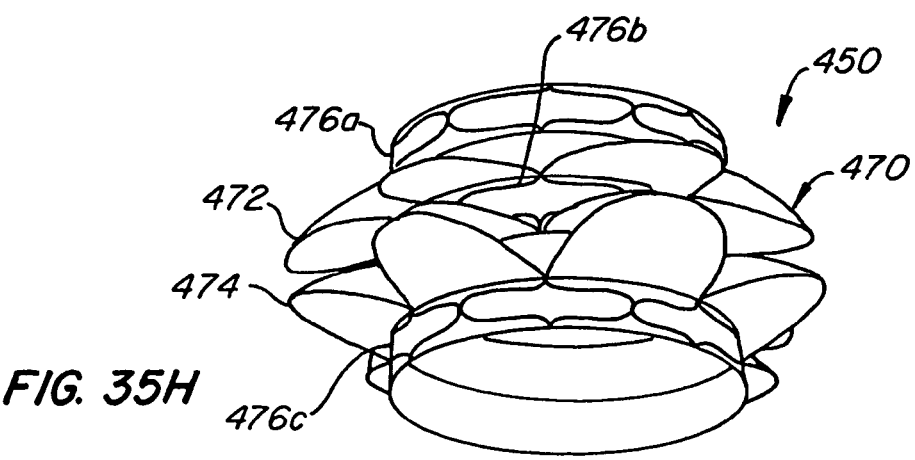

In FIG. 35G, wires 424b are retracted to expand lip region 472 and fully deploy apparatus 450. As with skirt region 474, expansion of lip region 472 preferably may be maintained via locking features. After both lip region 472 and skirt region 474 have been expanded, wires 424 may be removed from apparatus 450, thereby separating delivery system 410 from the apparatus. Delivery system 410 then may be removed, as seen in FIG. 35H.

As will be apparent to those of skill in the art, lip region 472 optionally may be expanded prior to expansion of skirt region 474. As yet another alternative, lip region 472 and skirt region 474 optionally may be expanded simultaneously, in parallel, in a step-wise fashion or sequentially. Advantageously, delivery of apparatus 450 is fully reversible until lip region 472 or skirt region 474 has been locked in the expanded configuration.

Figures 36A, 36B:
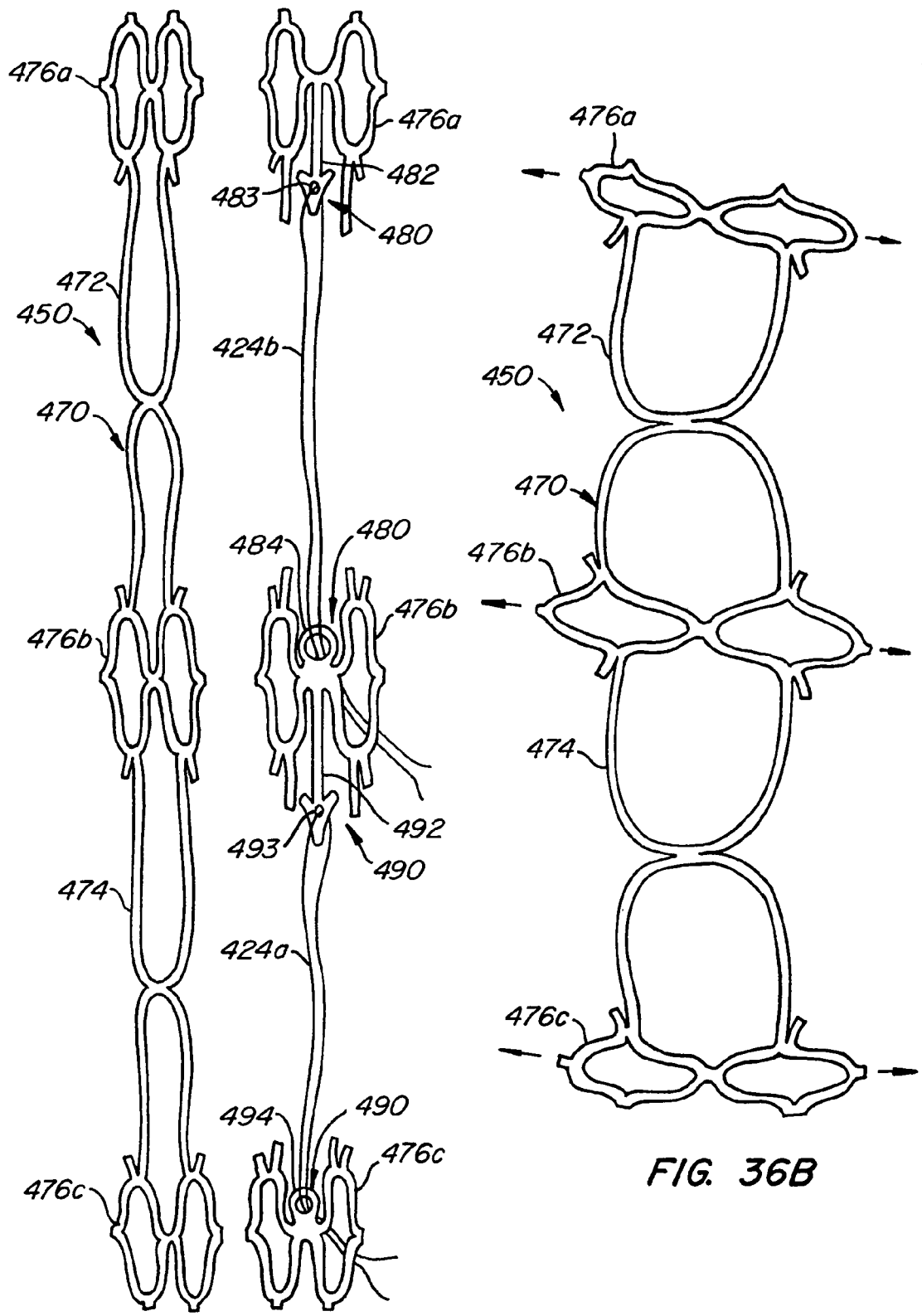
FIGS. 36A-E show more detail of the anchor of the embodiment shown in FIGS. 35A-H.

With reference now to FIGS. 36A-E, individual cells of anchor 470 of apparatus 450 are described to detail deployment and expansion of the apparatus. In FIG. 36A, individual cells of lip region 472, skirt region 474 and body regions 476a, 476b and 476c are shown in the collapsed delivery configuration, as they would appear while disposed within lumen 422 of sheath 420 of delivery system 410 of FIG. 35. A portion of the cells forming body regions 476, for example, every 'nth' row of cells, comprises locking features.

Body region 476a comprises male interlocking element 482 of lip lock 480, while body region 476b comprises female interlocking element 484 of lip lock 480. Male element 482 comprises eyelet 483. Wire 424b passes from female interlocking element 484 through eyelet 483 and back through female interlocking element 484, such that there is a double strand of wire 424b that passes through lumen 422 of catheter 420 for manipulation by a medical practitioner external to the patient. Body region 476b further comprises male interlocking element 492 of skirt lock 490, while body region 476c comprises female interlocking element 494 of the skirt lock. Wire 424a passes from female interlocking element 494 through eyelet 493 of male interlocking element 492, and back through female interlocking element 494. Lip lock 480 is configured to maintain expansion of lip region 472, while skirt lock 490 is configured to maintain expansion of skirt region 474.

Figure 36C:
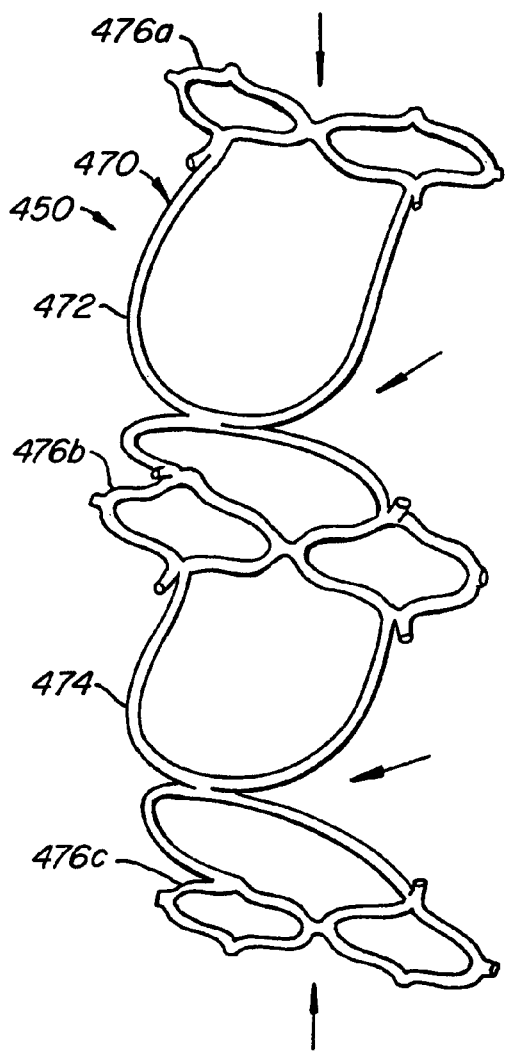
Figure 36D:
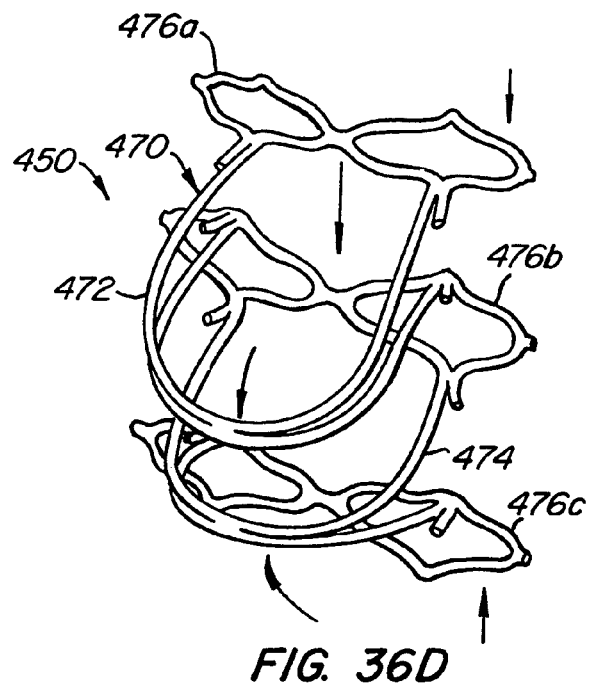
Figure 36E:
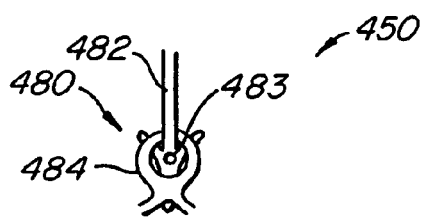

In FIG. 36B, anchor 470 is shown in the partially deployed configuration, e.g., after deployment from lumen 422 of sheath 420. Body regions 476, as well as lip region 472 and skirt region 474, self-expand to the partially deployed configuration. Full deployment is then achieved by retracting wires 424 relative to anchor 470, and expanding lip region 472 and skirt region 474 outward, as seen in FIGS. 36C and 36D. As seen in FIG. 36E, expansion continues until the male elements engage the female interlocking elements of lip lock 480 and skirt lock 490, thereby maintaining such expansion (lip lock 480 shown in FIG. 36E). Advantageously, deployment of apparatus 450 is fully reversible until lip lock 480 and/or skirt lock 490 has been actuated.

Figure 37A:
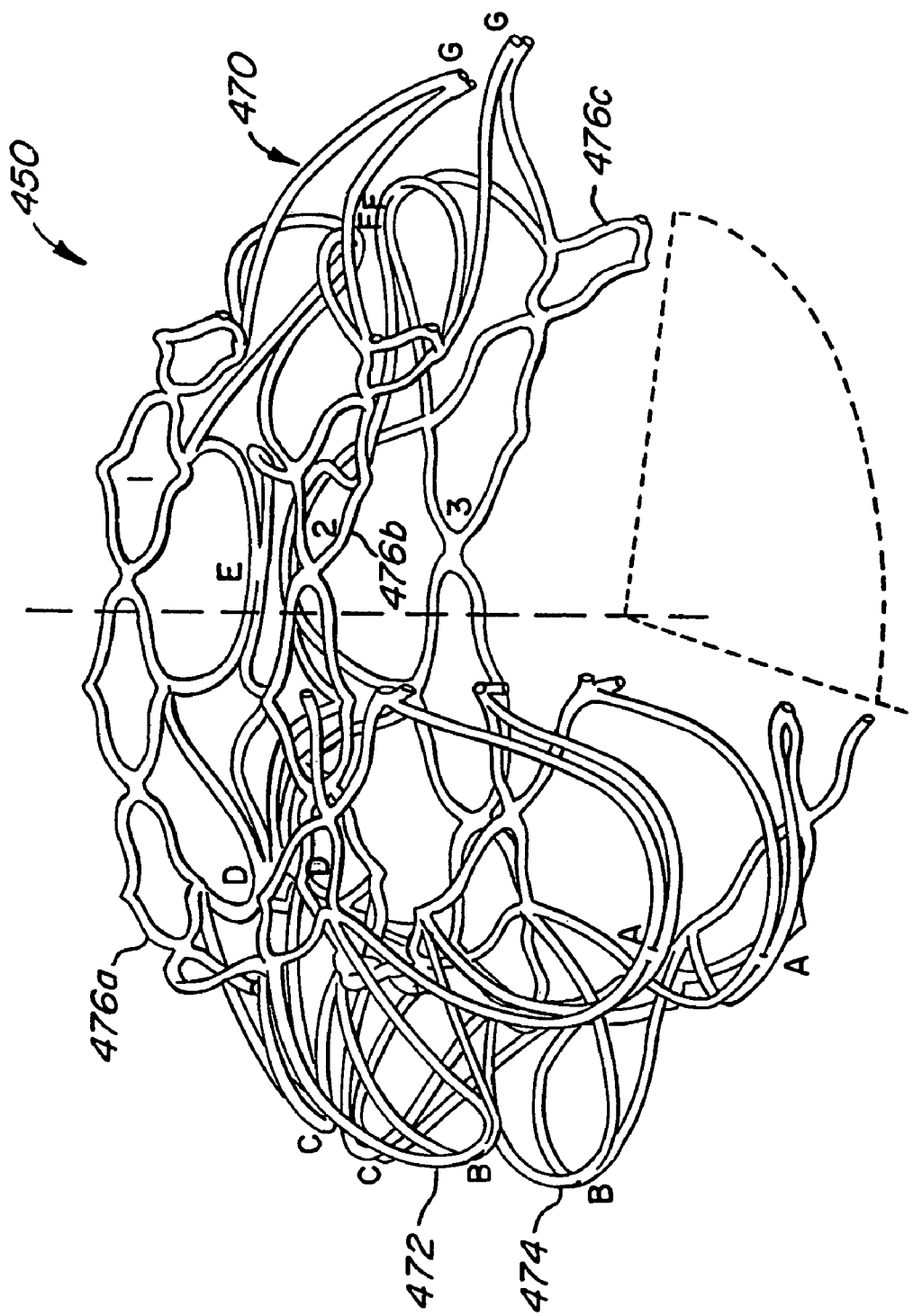
FIGS. 37A-B show other embodiments of the replacement heart valve and anchor of the invention.
Figure 37B:
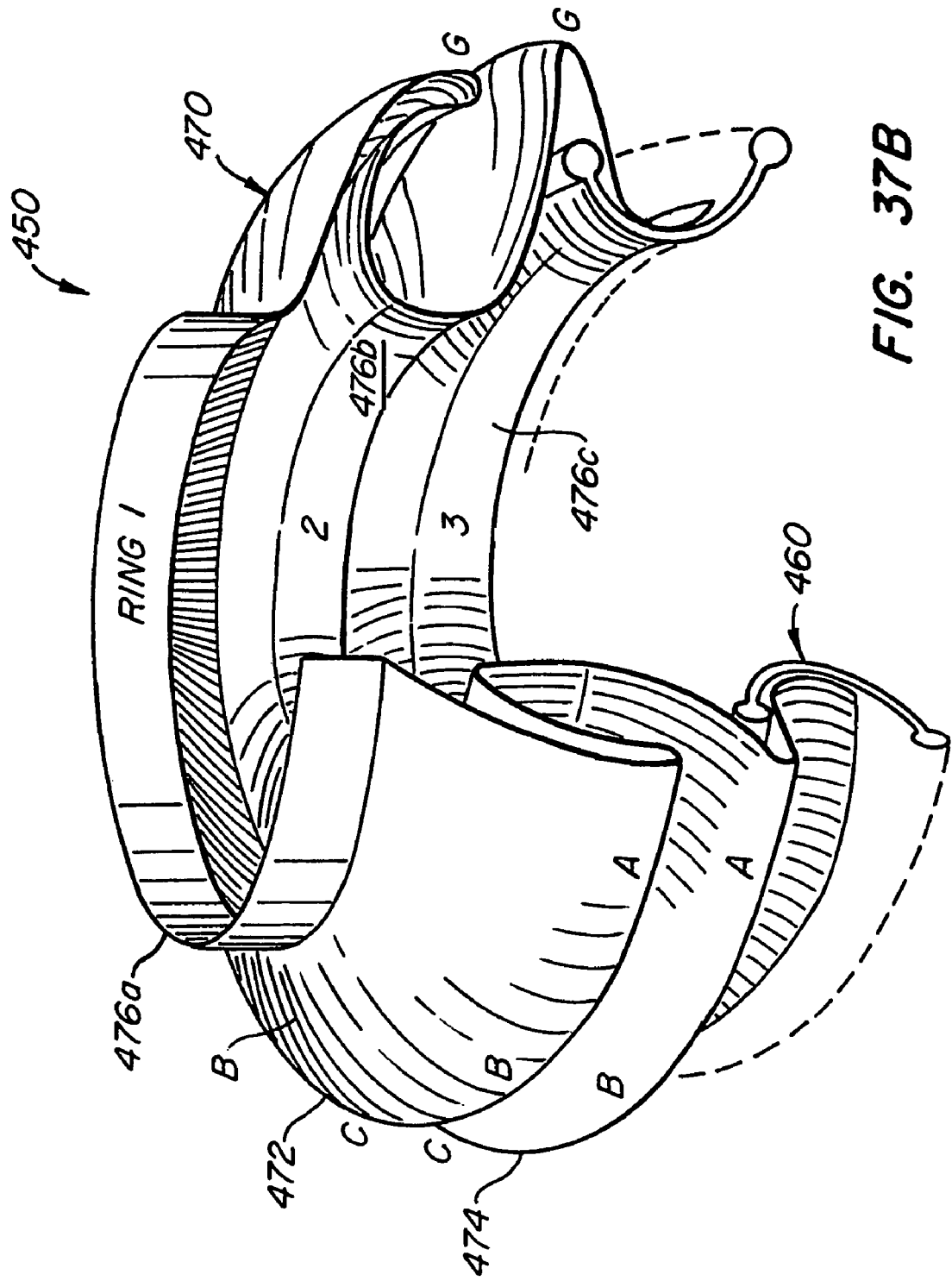

With reference to FIGS. 37A-B, isometric views, partially in section, further illustrate apparatus 450 in the fully deployed and expanded configuration. FIG. 37A illustrates the wireframe structure of anchor 470, while FIG. 37B illustrates an embodiment of anchor 470 covered in a biocompatible material B. Placement of replacement valve 460 within apparatus 450 may be seen in FIG. 37B. The patient's native valve is captured between lip region 472 and skirt region 474 of anchor 470 in the fully deployed configuration (see FIG. 38B).

Figure 38A:
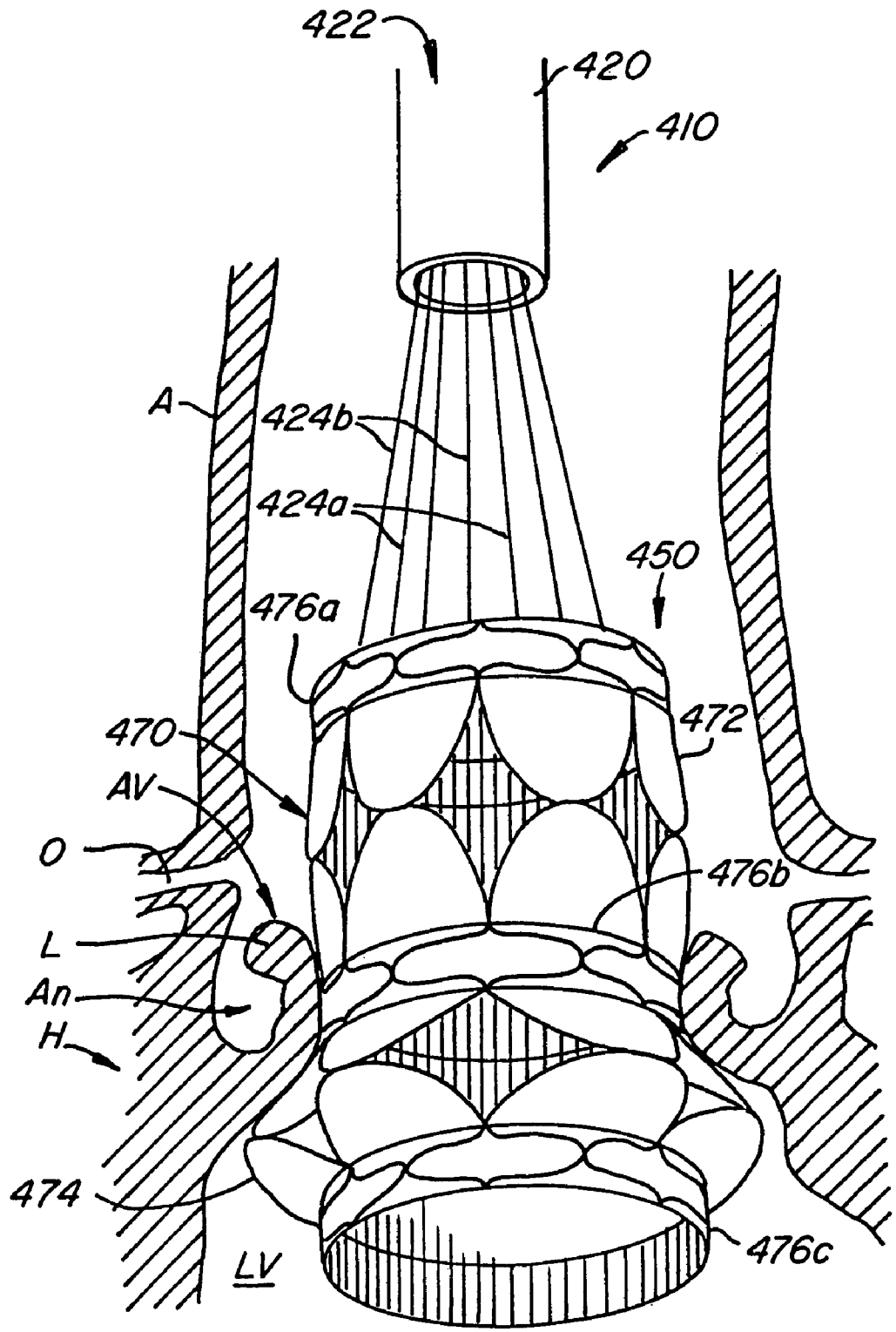
FIGS. 38A-C illustrate a method for endovascularly replacing a patient's diseased heart valve.
Figure 38B:
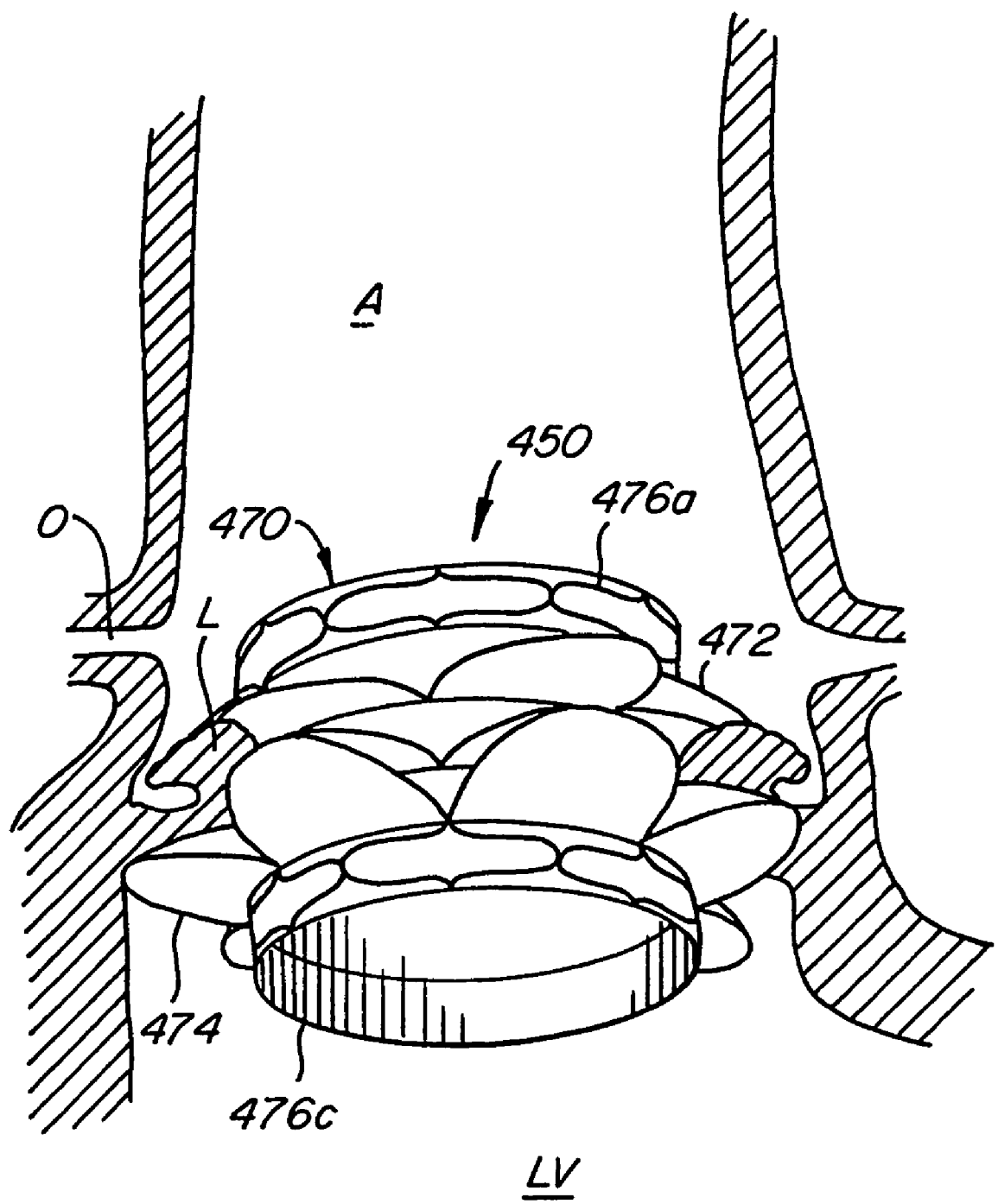
Figure 38C:
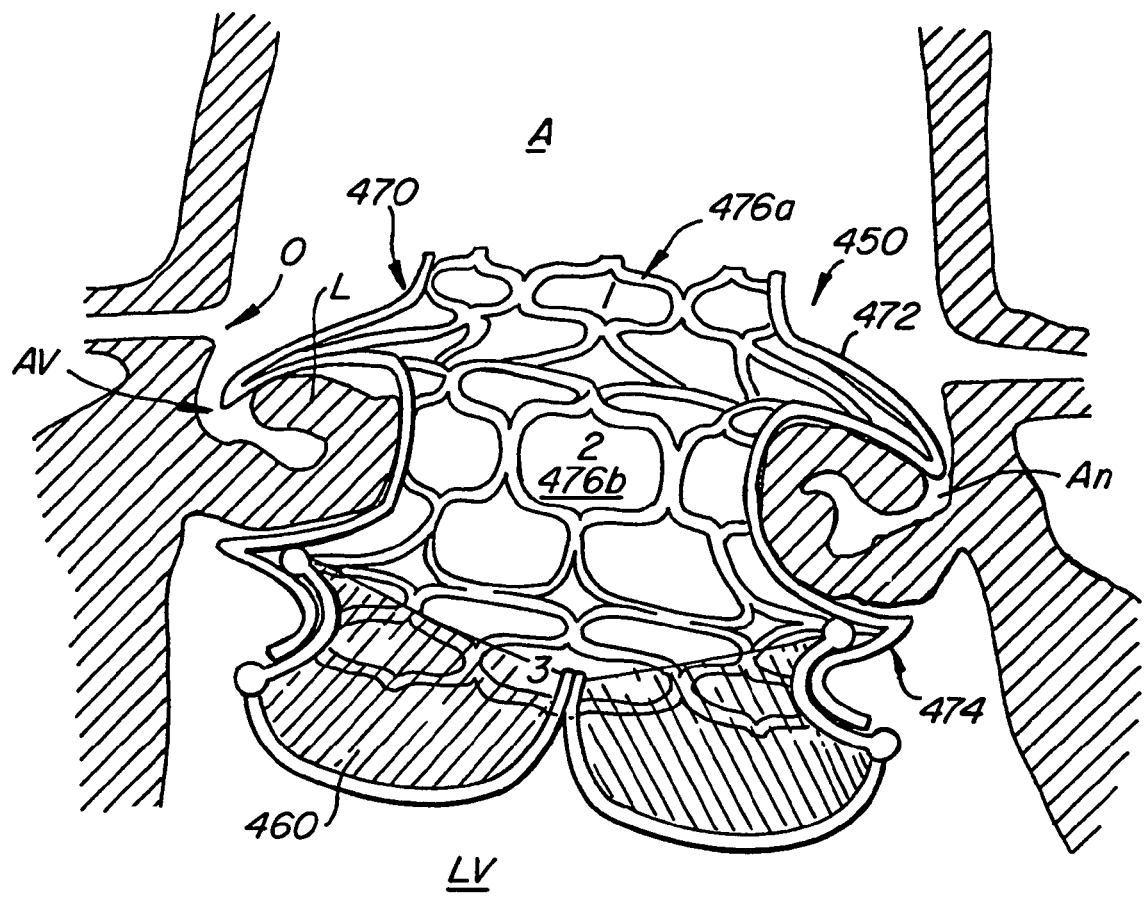

Referring to FIGS. 38A-C, in conjunction with FIGS. 35 and 36, a method for endovascularly replacing a patient's diseased aortic valve with apparatus 450 is described. Delivery system 410, having apparatus 450 disposed therein, is endovascularly advanced, preferably in a retrograde fashion, through a patient's aorta A to the patient's diseased aortic valve AV. Sheath 420 is positioned such that its distal end is disposed within left ventricle LV of the patient's heart H. As described with respect to FIG. 35, apparatus 450 is deployed from lumen 422 of sheath 420, for example, under fluoroscopic guidance, such that skirt section 474 is disposed within left ventricle LV, body section 476b is disposed across the patient's native valve leaflets L, and lip section 472 is disposed within the patient's aorta A. Advantageously, apparatus 450 may be dynamically repositioned to obtain proper alignment with the anatomical landmarks. Furthermore, apparatus 450 may be retracted within lumen 422 of sheath 420 via wires 424, even after anchor 470 has dynamically expanded to the partially deployed configuration, for example, to abort the procedure or to reposition sheath 420.

Once properly positioned, wires 424a are retracted to expand skirt region 474 of anchor 470 within left ventricle LV. Skirt region 474 is locked in the expanded configuration via skirt lock 490, as previously described with respect to FIG. 36. In FIG. 38A, skirt region 474 is maneuvered such that it engages the patient's valve annulus An and/or native valve leaflets L, thereby providing positive registration of apparatus 450 relative to the anatomical landmarks.

Wires 424b are then actuated external to the patient in order to expand lip region 472, as previously described in FIG. 35. Lip region 472 is locked in the expanded configuration via lip lock 480. Advantageously, deployment of apparatus 450 is fully reversible until lip lock 480 and/or skirt lock 490 has been actuated. Wires 424 are pulled from eyelets 483 and 493, and delivery system 410 is removed from the patient. As will be apparent, the order of expansion of lip region 472 and skirt region 474 may be reversed, concurrent, etc.

As seen in FIG. 38B, lip region 472 engages the patient's native valve leaflets L, thereby providing additional positive registration and reducing a risk of lip region 472 blocking the patient's coronary ostia o. FIG. 38C illustrates the same in cross-sectional view, while also showing the position of replacement valve 460. The patient's native leaflets are engaged and/or captured between lip region 472 and skirt region 474. Advantageously, lip region 472 precludes distal migration of apparatus 450, while skirt region 474 precludes proximal migration. It is expected that lip region 472 and skirt region 474 also will reduce paravalvular regurgitation.

What is claimed is:

1. A replacement heart valve system comprising:
   an anchor having a collapsed endovascular delivery configuration and a foreshortened deployed configuration;
   a replacement valve support comprising a valve commissure support portion, the replacement valve support secured to the anchor in the anchor's delivery and deployed configurations, wherein the commissure support portion has a length that is substantially the same in the anchor's delivery and deployed configurations, wherein the anchor is adapted to foreshorten relative to the commissure support portion; and
   a replacement valve supported by the commissure support portion, wherein the commissure support portion maintains substantially the same orientation while the anchor is in the deployed configuration.

2. The system of claim 1 wherein the replacement valve support comprises a base portion and a commissure support portion, the base portion being adapted to be radially expandable.

3. The system of claim 1 wherein the replacement valve support comprises a base portion and a commissure support portion axially separated from the base portion.

4. The system of claim 1 wherein the replacement valve support comprises a base portion and a commissure support portion, the replacement valve support being secured to the anchor solely at the base portion.

5. The system of claim 4 where the replacement valve support is secured to the anchor at the base portion and at the commissure support portion.

6. The system of claim 1 further comprising an anchor lock adapted to lock the anchor in the deployed configuration.

7. The system of claim 1 wherein the replacement valve support comprises a plurality of commissure supports.

8. The system of claim 1 wherein the anchor comprises a braid.

9. The replacement heart valve system of claim 1 wherein the commissure support portion has a longitudinal axis that maintains a substantially parallel orientation relative to a longitudinal axis of the anchor when the anchor is in the deployed configuration.

10. A replacement heart valve system comprising:
    an anchor having a collapsed endovascular delivery configuration and a foreshortened deployed configuration;
    a replacement valve support comprising a valve commissure support portion, the replacement valve support secured to the anchor in the anchor's delivery and deployed configurations, wherein the commissure support portion has a length that is substantially the same in the anchor's delivery and deployed configurations, wherein the anchor is adapted to foreshorten relative to the commissure support portion; and
    a replacement valve supported by the commissure support portion, wherein the commissure support portion maintains substantially the same orientation while the anchor is in the deployed configuration, wherein the replacement valve support comprises an anchor actuator interface and wherein the system further comprises an anchor actuator which interfaces with the anchor actuator interface.

11. The system of claim 10 wherein the commissure support portion comprises the anchor actuator interface which interfaces with the anchor actuator.

12. The system of claim 11 wherein the anchor actuator interface comprises a first anchor actuator interface, the anchor further comprising a second anchor actuator interface which interfaces with a second anchor actuator.

13. The system of claim 12 wherein the first anchor actuator interface is adapted to actuate a distal portion of the anchor and the second anchor actuator interface is adapted to actuate a proximal portion of the anchor.

14. The system of claim 10 wherein the replacement valve support comprises a plurality of anchor actuator interfaces which each interface with an anchor actuator.

15. The system of claim 14 wherein the plurality of anchor actuator interfaces are adapted to actuate a distal portion of the anchor, the system further comprising a plurality of proximal anchor actuator interfaces adapted to actuate a proximal portion of the anchor.

16. A replacement heart valve system comprising:
an anchor having a collapsed endovascular delivery configuration and a foreshortened deployed configuration;
a replacement valve support comprising a valve commissure support portion, the replacement valve support secured to the anchor;
a replacement valve supported by the valve commissure support portion; and
an anchor lock comprising a first locking element and a second locking element, the lock adapted to lock the anchor in the foreshortened deployed configuration,
wherein the commissure support portion comprises the first locking element.

17. The system of claim 16 wherein the replacement valve support further comprises a base portion.

18. The system of claim 16 wherein the second locking element is secured to the anchor.

19. The system of claim 18 wherein the first and second locking elements are axially closer to one another when the anchor is in the foreshortened deployed configuration than when the anchor is in the delivery configuration.

20. The system of claim 16 wherein the anchor lock is adapted to lock the anchor in a plurality of expanded configurations.

21. A replacement heart valve comprising:
an anchor having a collapsed endovascular delivery configuration and an expanded deployed configuration;
a replacement valve support comprising a valve commissure support portion, the commissure support portion secured to the anchor in the anchor's delivery and deployed configurations and having a length that is substantially the same in the anchor's delivery and deployed configurations, wherein the commissure support portion comprises an anchor actuator interface which is configured and arranged to interface with an anchor actuator, wherein the anchor actuator interfaces with the anchor actuator interface such that the anchor actuator is adapted to apply an axially directed force to the commissure support portion to foreshorten the anchor; and
a replacement valve supported by the valve commissure support portion.

22. A replacement heart valve comprising:
an anchor having a collapsed endovascular delivery configuration and an expanded deployed configuration;
a replacement valve support comprising a valve commissure support portion, the commissure support portion secured to the anchor in the anchor's delivery and deployed configurations and having a length that is substantially the same in the anchor's delivery and deployed configurations, wherein the commissure support portion comprises an anchor actuator interface which is configured and arranged to interface with an anchor actuator; and
a replacement valve supported by the valve commissure support portion,
wherein the anchor actuator interfaces with the anchor actuator interface such that the anchor actuator is adapted apply a proximally directed force to the valve commissure support portion to foreshorten the anchor.

23. A replacement heart valve comprising:
an anchor having a collapsed endovascular delivery configuration and a foreshortened deployed configuration;
a replacement valve support comprising a valve commissure support portion, the commissure support portion secured to the anchor in the anchor's delivery and deployed configurations and having a length that is substantially the same in the anchor's delivery and deployed configurations, wherein the commissure support portion comprises an anchor actuator interface which is configured and arranged to interface with an anchor actuator;
a replacement valve supported by the valve commissure support portion; and
a lock adapted to lock the anchor in the foreshortened deployed configuration, wherein the commissure support portion comprises a first element of the lock.

* * * * *